US010941138B2

United States Patent
Almansa-Rosales et al.

(10) Patent No.: US 10,941,138 B2
(45) Date of Patent: *Mar. 9, 2021

(54) QUINOLINE AND ISOQUINOLINE DERIVATIVES FOR TREATING PAIN AND PAIN RELATED CONDITIONS

(71) Applicant: ESTEVE PHARMACEUTICALS, S.A., Barcelona (ES)

(72) Inventors: Carmen Almansa-Rosales, Barcelona (ES); Susana Yenes-Mínguez, Molins de Rei (ES); Marina Virgili-Bernado, Barcelona (ES); Monica Alonso-Xalma, Barcelona (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 16/470,568

(22) PCT Filed: Dec. 20, 2017

(86) PCT No.: PCT/EP2017/083717
§ 371 (c)(1),
(2) Date: Jun. 18, 2019

(87) PCT Pub. No.: WO2018/115064
PCT Pub. Date: Jun. 28, 2018

(65) Prior Publication Data
US 2020/0087291 A1    Mar. 19, 2020

(30) Foreign Application Priority Data
Dec. 20, 2016 (EP) .................................. 16382629

(51) Int. Cl.
*C07D 409/12* (2006.01)
*C07D 401/12* (2006.01)
*C07D 407/12* (2006.01)
*C07D 417/12* (2006.01)

(52) U.S. Cl.
CPC ......... *C07D 409/12* (2013.01); *C07D 401/12* (2013.01); *C07D 407/12* (2013.01); *C07D 417/12* (2013.01)

(58) Field of Classification Search
CPC .. C07D 409/12; C07D 401/12; C07D 407/12; C07D 417/12
See application file for complete search history.

(56) References Cited

U.S. PATENT DOCUMENTS 5,023,269 A    6/1991    Robertson et al.
2019/0345146 A1  11/2019   Almansa-Rosales et al.

FOREIGN PATENT DOCUMENTS

| EP | 0273658 | 7/1988 |
|---|---|---|
| WO | WO2002094262 | 11/2002 |
| WO | WO 2004/043931 | 5/2004 |
| WO | WO2008150528 | 12/2008 |
| WO | WO 2016/154027 | 9/2016 |

OTHER PUBLICATIONS

Boot, J.R., et al., "Benzothienyloxy phenylpropanamines, novel dual inhibitors of serotonin and norepinephrine reuptake", Bioorganic & Medicinal Chemistry Letters, 14, 2004, pp. 5395-5299.
International Search Report for PCT/EP2017/083717 dated Jan. 26, 2018.
Bymaster, F.P., "Duloxetine (Cymbalta), a dual inhibitor of serotonin and norepinephrine reuptake", Bioorganic & Medpirial Chemistry Letters, vol. 13, No. 24, Dec. 1, 2003. pp 4477-4480.
International Search Report for PCT/EP2017/083724 dated Jan. 26, 2018.
Chabot-Doré, Anne-Julie, et al., "Dual allosteric modulation of opioid antinociceptive potency by α2A-adrenoceptors", Neuropharmacology 99, 2015, pp. 285-300.
Davies, Anthony, et al., "Functional biology of the α2δ subunits of voltage-gated calcium channels". Trends in Pharmacological Sciences, vol. 28, No. 5, 2007, pp. 220-228.
Dolphin, Annette, C., "Calcium channel auxiliary α2δ and β subunits: trafficking and one step beyond", Nature Reviews Neuroscience AOP, Jul. 18, 2012, pp. 542-555.
Dolphin, Annette, C., "The α2δ subunits of voltage-gated calcium channels", Biochirnica et Biophysica Acta, 1828, 2013, pp. 1541-1549.
Fairbanks, Carolyn, A., "Pharmacological profiles of Alpha 2 adrenergic receptor agonists identified using genetically altered Mice and isobolographic analysis", Pharmacol. Ther., 123(2), Aug. 2009, pp. 224-238.
Frampton, James, E., "Pregabalin: A review of its use in adults with generalized anxiety disorder", CNS Drugs, 28, 2014, pp. 835-854.
Gilron, Ian, et al., "Combination pharmacotherapy for management of chronic pain: from bench to bedside", Lancet Neurol 12, 2013, pp. 1084-1095.
Goldberg, Daniel, S., et al., "Pain as a global public health priority", BMC Public Health, 11:770, 2011, pp. 1-5.

(Continued)

*Primary Examiner* — Timothy R Rozof
(74) *Attorney, Agent, or Firm* — Hueschen and Sage

(57) ABSTRACT

The present invention relates to new compounds of formula (I):

(I)

$$Z\diagdown O\diagup \overset{R_1}{\underset{}{\diagup}}\diagdown\diagup N\underset{\underset{R_3}{|}}{-}R_2$$

showing great affinity and activity towards the subunit α2δ of voltage-gated calcium channels (VGCC), especially the α2δ-1 subunit of voltage-gated calcium channels or dual activity towards subunit α2δ of voltage-gated calcium channels (VGCC), especially the α2δ-1 subunit of voltage-gated calcium channels, and the noradrenaline transporter (NET).

14 Claims, No Drawings

(56) References Cited

OTHER PUBLICATIONS

Hajós, Mihály, et al., "The selective norepinephrine reuptake inhibitor antidepressant reboxetine: pharmacological and clinical profile", CNS Drug Reviews, vol. 10, No. 1, 2004, pp. 23-44.
Hartrick, Crag, T., "Noradrenergic reuptake inhibition in the treatment of pain", Expert Opin Investig, Drugs, 21(12), 2012, pp. 1827-1834.
Hayashida, Ken-ichiro, et al., "Multiplicative interactions to enhance gabapentin to treat neuropathic pain", European Journal of Pharmacology, 598, 2008, pp. 21-26.
Hopkins, Andrew, L., "Network pharmacology: the next paradigm in drug discovery", Nature Chemical Biology, vol. 4, No. 11, Nov. 2008, pp. 682-690.
Kasper, S., et al., "Reboxetine: the first selective noradrenaline re-uptake inhibitor", Exp. Opin. Pharmacother., 1(4), 2000, pp. 771-782.
Lehár, Joseph, et al., "Synergistic drug combinations improve therapeutic selectivity", Nat Biotechnol., 27(7), Jul. 2009, pp. 659-666.
Mason, Stephen, T., "Noradrenaline in the in brain: progress in theories of behavioural function", Progress in Neurobiology, vol. 16, 1981, pp. 263-303.
Miranda, Hugo, F., "Isobolographic analysis in mice of the interaction of gabapentin and nortriptyline in relieving orofacial pain", Journal of Orofacial Pain, vol. 27, No. 4, 2013, pp. 361-366.
Miranda, Hugo, F., et al., "Antinociceptive synergism of gabapentin and nortriptyline in mice with partial sciatic nerve ligation", Pharmacology, 95, 2015, pp. 59-64.
Mochiucki, Daisuke, "Serotonin and noradrenaline reuptake inhibitors in animal models of pain", Hum Psychopharmacol Clin Exp, 19, 2004, pp. S15-S19.

Neumaier, Felix, et al., "Voltage-gated calcium channels: determinants of channel function and modulation by inorganic cations", Progress in Neurobiology, 129, 2015, pp. 1-36.
Nicolson, Stephen, E., MD, et al., "Comorbid pain, depression, and anxiety: multifaceted pathology allows for multifaceted treatment", Harv Rev Psychiatry, 17, 2009, pp. 407-420.
Ossipov, Michael, H., et al., "Central modulation of pain", J Clin Invest., 120(11), 2010, pp. 3779-3787.
Perret, Danielle, et al., "Targeting voltage-gated calcium channels for neuropathic pain management", Neurotherapeutics: The Journal of the American Society for Experimental NeuroTherapeutics, vol. 6, Oct. 2000, pp. 679-692.
Schröder et al., Erratum in: J Pharmacol. Exp. Ther. 2012; 342: 232.
Schröder, W., et al., "Synergistic interaction between the two mechanisms of action of tapentadol in analgesia", The Journal of Pharmacology and Experimental Therapeutics, vol. 337, No. 1, 2011, pp. 312-320.
Tanabe, Mitsuo, et al., "Pain relief by gabapentin and pregabalin via supraspinal mechanisms after peripheral nerve injury", Journal of Neuroscience Research, 86, 2008, pp. 3258-3264.
Turk, Dennis, C., et al., "Treatment of chronic non-cancer pain", Lancet, vol. 377, Jun. 25, 2011, pp. 2226-2235.
Vink, S., et al., "Targeting voltage-gated calcium channels: developments in peptide and small-molecule inhibitors for the treatment of neuropathic pain", British Journal of Pharmacology, 167, 2012, pp. 970-989.
Wang, Ruizhong, et al, "Descending facilitation maintains long-term spontaneous neuropathic pain", J Pain., 14(8), Aug. 2013, pp. 845-853.
Zamponi, Gerald, W. et al., "The physiology, pathology, and pharmacology of voltage-gated calcium channels and their future therapeutic potential", Pharmacol Rev, 67, Oct. 2015, pp. 821-870.
Zhang, C., et al., "Synergistic action by multi-targeting compounds produces a potent compound combination for human NSCLC both in vitro and in vivo", Cell Death and Disease, 5, 2014, e1138, pp. 1-12.

QUINOLINE AND ISOQUINOLINE DERIVATIVES FOR TREATING PAIN AND PAIN RELATED CONDITIONS

FIELD OF THE INVENTION

The present invention relates to new compounds that show great affinity and activity towards the subunit α2δ of voltage-gated calcium channels (VGCC), especially the α2δ-1 subunit of voltage-gated calcium channels or dual activity towards subunit α2δ of voltage-gated calcium channels (VGCC), especially the α2δ-1 subunit of voltage-gated calcium channels, and the noradrenaline transporter (NET). The invention is also related to the process for the preparation of said compounds as well as to compositions comprising them, and to their use as medicaments.

BACKGROUND OF THE INVENTION

The adequate management of pain represents an important challenge, since currently available treatments provide in many cases only modest improvements, leaving many patients unrelieved (Turk, D. C., Wilson, H. D., Cahana, A.; 2011; *Lancet* 377; 2226-2235). Pain affects a big portion of the population with an estimated prevalence of 20% and its incidence, particularly in the case of chronic pain, is increasing due to the population ageing. Additionally, pain is clearly correlated to comorbidities, such as depression, anxiety and insomnia, which leads to important productivity losses and socio-economical burden (Goldberg, D. S., McGee, S. J.; 2011; *BMC Public Health;* 11; 770). Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

Voltage-gated calcium channels (VGCC) are required for many key functions in the body. Different subtypes of voltage-gated calcium channels have been described (Zamponi et al.; Pharmacol. Rev.; 2015; 67; 821-870). The VGCC are assembled through interactions of different subunits, namely α1 ($Ca_v\alpha1$), β($Ca_v\beta$) α2δ ($Ca_v\alpha2\delta$) and γ ($Ca_v\gamma$). The α1 subunits are the key porous forming units of the channel complex, being responsible for $Ca^{2+}$ conduction and generation of $Ca^{2+}$ influx. The α2δ, β, and γ subunits are auxiliary, although they are very important for the regulation of the channel since they increase the expression of α1 subunits in the plasma membrane as well as modulate their function resulting in functional diversity in different cell types. Based on their physiological and pharmacological properties, VGCC can be subdivided into low voltage-activated T-type ($Ca_v3.1$, $Ca_v3.2$, and $Ca_v3.3$), and high voltage-activated L-($Ca_v1.1$ through $Ca_v1.4$), N—($Ca_v2.2$), P/Q-($Ca_v2.1$), and R—($Ca_v2.3$) types, depending on the channel forming $Ca_v\alpha$ subunits. All of these five subclasses are found in the central and peripheral nervous systems. Regulation of intracellular calcium through activation of these VGCC plays obligatory roles in: 1) neurotransmitter release, 2) membrane depolarization and hyperpolarization, 3) enzyme activation and inactivation, and 4) gene regulation (Perret and Luo; Neurotherapeutics; 2009; 6; 679-692; Zamponi et al., 2015; Neumaier et al.; Prog. Neurobiol.; 2015; 129; 1-36). A large body of data has clearly indicated that VGCC are implicated in mediating various disease states including pain processing. Drugs interacting with the different calcium channel subtypes and subunits have been developed. Current therapeutic agents include drugs targeting L-type $Ca_v1.2$ calcium channels, particularly 1,4-dihydropyridines, which are widely used in the treatment of hypertension. T-type ($Ca_v3$) channels are the target of ethosuximide, widely used in absence epilepsy. Ziconotide, a peptide blocker of N-type ($Ca_v2.2$) calcium channels, has been approved as a treatment of intractable pain.

The $Ca_v1$ and $Ca_v2$ subfamilies contain an auxiliary α2δ subunit which is the therapeutic target of the gabapentinoid drugs of value in certain epilepsies and chronic neuropathic pain (Perret and Luo, 2009; Vink and Alewood; British J. Pharmacol.; 2012; 167; 970-989). To date, there are four known α2δ subunits, each encoded by a unique gene and all possessing splice variants. Each α2δ protein is encoded by a single messenger RNA and is post-translationally cleaved and then linked by disulfide bonds. Four genes encoding α2δ subunits have now been cloned. α2δ-1 was initially cloned from skeletal muscle and shows a fairly ubiquitous distribution. The α2δ-2 and α2δ-3 subunits were subsequently cloned from brain. The most recently identified subunit, α2δ-4, is largely non-neuronal. The human α2δ-4 protein sequence shares 30, 32 and 61% identity with the human α2δ-1, α2δ-2 and α2δ-3 subunits, respectively. The gene structure of all α2δ subunits is similar. All α2δ subunits show several splice variants (Davies et al.; Trends Pharmacol. Sci.; 2007; 28; 220-228; Dolphin, A. C.; Nat. Rev. Neurosci.; 2012; 13; 542-555; Dolphin, A. C.; Biochim. Biophys. Acta; 2013; 1828; 1541-1549).

The $Ca_v\alpha2\delta$-1 subunit may play an important role in neuropathic pain development (Perret and Luo, 2009; Vink and Alewood, 2012). Biochemical data have indicated a significant $Ca_v\alpha2\delta$-1, but not $Ca_v\alpha2\delta$-2, subunit upregulation in the spinal dorsal horn, and DRG (dorsal root ganglia) after nerve injury that correlates with neuropathic pain development. In addition, blocking axonal transport of injury-induced DRG $Ca_v\alpha_2\delta$-1 subunit to the central presynaptic terminals diminishes tactile allodynia in nerve injured animals, suggesting that elevated DRG $Ca_v\alpha2\delta$-1 subunit contributes to neuropathic allodynia.

The $Ca_v\alpha2\delta$-1 subunit (and the $Ca_v\alpha2\delta$-2, but not $Ca_v\alpha2\delta$-3 and $Ca_v\alpha2\delta$-4, subunits) is the binding site for gabapentin which has anti-allodynic/hyperalgesic properties in patients and animal models. Because injury-induced $Ca_v\alpha2\delta$-1 expression correlates with neuropathic pain, development and maintenance, and various calcium channels are known to contribute to spinal synaptic neurotransmission and DRG neuron excitability, injury-induced $Ca_v\alpha2\delta$-1 subunit upregulation may contribute to the initiation and maintenance of neuropathic pain by altering the properties and/or distribution of VGCC in the subpopulation of DRG neurons and their central terminals, therefore modulating excitability and/or synaptic neuroplasticity in the dorsal horn. Intrathecal antisense oligonucleotides against the $Ca_v\alpha2\delta$-1 subunit can block nerve injury-induced $Ca_v\alpha2\delta$-1 upregulation and prevent the onset of allodynia and reserve established allodynia.

As above mentioned, the α2δ subunits of VGCC form the binding site for gabapentin and pregabalin which are structural derivatives of the inhibitory neurotransmitter GABA although they do not bind to GABAA, GABAB, or benzodiazepine receptors, or alter GABA regulation in animal brain preparations. The binding of gabapentin and pregabalin to the $Ca_v\alpha2\delta$-1 subunit results in a reduction in the calcium-dependent release of multiple neurotransmitters, leading to efficacy and tolerability for neuropathic pain management. Gabapentinoids may also reduce excitability by inhibiting synaptogenesis (Perret and Luo, 2009; Vink and Alewood, 2012, Zamponi et al., 2015).

Thus, the present invention relates to compounds with inhibitory effect towards α2δ subunits of voltage-gated calcium channels, preferably towards α2δ-1 subunit of voltage-gated calcium channels.

It is also known that Noradrenaline (NA), also called norepinephrine, functions in the human brain and body as a hormone and neurotransmitter. Noradrenaline exerts many effects and mediates a number of functions in living organisms. The effects of noradrenaline are mediated by two distinct super-families of receptors, named alpha- and beta-adrenoceptors. They are further divided into subgroups exhibiting specific roles in modulating behavior and cognition of animals. The release of the neurotransmitter noradrenaline throughout the mammalian brain is important for modulating attention, arousal, and cognition during many behaviors (Mason, S. T.; Prog. Neurobiol.; 1981; 16; 263-303).

The noradrenaline transporter (NET, SLC6A2) is a monoamine transporter mostly expressed in the peripheral and central nervous systems. NET recycles primarily NA, but also serotonin and dopamine, from synaptic spaces into presynaptic neurons. NET is a target of drugs treating a variety of mood and behavioral disorders, such as depression, anxiety, and attention-deficit/hyperactivity disorder (ADHD). Many of these drugs inhibit the uptake of NA into the presynaptic cells through NET. These drugs therefore increase the availability of NA for binding to postsynaptic receptors that regulate adrenergic neurotransmission. NET inhibitors can be specific. For example, the ADHD drug atomoxetine is a NA reuptake inhibitor (NRI) that is highly selective for NET. Reboxetine was the first NRI of a new antidepressant class (Kasper et al.; Expert Opin. Pharmacother.; 2000; 1; 771-782). Some NET inhibitors also bind multiple targets, increasing their efficacy as well as their potential patient population.

Endogenous, descending noradrenergic fibers impose analgesic control over spinal afferent circuitry mediating the transmission of pain signals (Ossipov et al.; J. Clin. Invest.; 2010; 120; 3779-3787). Alterations in multiple aspects of noradrenergic pain processing have been reported, especially in neuropathic pain states (Ossipov et a., 2010; Wang et al.; J. Pain; 2013; 14; 845-853). Numerous studies have demonstrated that activation of spinal α2-adrenergic receptors exerts a strong antinociceptive effect. Spinal clonidine blocked thermal and capsaicin-induced pain in healthy human volunteers (Ossipov et a., 2010). Noradrenergic reuptake inhibitors have been used for the treatment of chronic pain for decades: most notably the tricyclic antidepressants, amitriptyline, and nortriptyline. Once released from the presynaptic neuron, NA typically has a short-lived effect, as much of it is rapidly transported back into the nerve terminal. In blocking the reuptake of NA back into the presynaptic neurons, more neurotransmitter remains for a longer period of time and is therefore available for interaction with pre- and postsynaptic $\alpha_2$-adrenergic receptors (AR). Tricyclic antidepressants and other NA reuptake inhibitors enhance the antinociceptive effect of opioids by increasing the availability of spinal NA. The $\alpha_2$A-AR subtype is necessary for spinal adrenergic analgesia and synergy with opioids for most agonist combinations in both animal and humans (Chabot-Doré et al.; Neuropharmacology; 2015; 99; 285-300). A selective upregulation of spinal NET in a rat model of neuropathic pain with concurrent downregulation of serotonin transporters has been shown (Fairbanks et al.; Pharmacol. Ther.; 2009; 123; 224-238). Inhibitors of NA reuptake such as nisoxetine, nortriptyline and maprotiline and dual inhibitors of the noradrenaline and serotonin reuptake such as imipramine and milnacipran produce potent anti-nociceptive effects in the formalin model of tonic pain. Neuropathic pain resulting from the chronic constriction injury of the sciatic nerve was prevented by the dual uptake inhibitor, venlafaxine. In the spinal nerve ligation model, amitriptyline, a non-selective serotonin and noradrenaline reuptake blocker, the preferential noradrenaline reuptake inhibitor, desipramine and the selective serotonin and noradrenaline reuptake inhibitors, milnacipran and duloxetine, produce a decrease in pain sensitivity whereas the selective serotonin reuptake inhibitor, fluoxetine, is ineffective (Mochizucki, D.; Psychopharmacol.; 2004; Supplm. 1; S15-S19; Hartrick, C. T.; Expert Opin. Investig. Drugs; 2012; 21; 1827-1834). A number of nonselective investigational agents focused on noradrenergic mechanisms with the potential for additive or even synergistic interaction between multiple mechanisms of action is being developed (Hartrick, 2012).

Polypharmacology is a phenomenon in which a drug binds multiple rather than a single target with significant affinity. The effect of polypharmacology on therapy can be positive (effective therapy) and/or negative (side effects). Positive and/or negative effects can be caused by binding to the same or different subsets of targets; binding to some targets may have no effect. Multi-component drugs or multi-targeting drugs can overcome toxicity and other side effects associated with high doses of single drugs by countering biological compensation, allowing reduced dosage of each compound or accessing context-specific multitarget mechanisms. Because multitarget mechanisms require their targets to be available for coordinated action, one would expect synergies to occur in a narrower range of cellular phenotypes given differential expression of the drug targets than would the activities of single agents. In fact, it has been experimentally demonstrated that synergistic drug combinations are generally more specific to particular cellular contexts than are single agent activities, such selectivity is achieved through differential expression of the drugs' targets in cell types associated with therapeutic, but not toxic, effects (Lehar et al.; Nat. Biotechnol.; 2009; 27; 659-666).

In the case of chronic pain, which is a multifactorial disease, multi-targeting drugs may produce concerted pharmacological intervention of multiple targets and signaling pathways that drive pain. Because they actually make use of biological complexity, multi-targeting (or multi-component drugs) approaches are among the most promising avenues toward treating multifactorial diseases such as pain (Gilron et al.; Lancet Neurol.; 2013; 12(11); 1084-1095). In fact, positive synergistic interaction for several compounds, including analgesics, has been described (Schröder et al; J. Pharmacol. Exp. Ther.; 2011; 337; 312-320; Zhang et al.; Cell Death Dis.; 2014; 5; e1138; Gilron et al., 2013).

Given the significant differences in pharmacokinetics, metabolism and bioavailability, reformulation of drug combinations (multi-component drugs) is challenging. Further, two drugs that are generally safe when dosed individually cannot be assumed to be safe in combination. In addition to the possibility of adverse drug-drug interactions, if the theory of network pharmacology indicates that an effect on phenotype may derive from hitting multiple targets, then that combined phenotypic perturbation may be efficacious or deleterious. The major challenge to both drug combination strategies is the regulatory requirement for each individual drug to be shown to be safe as an individual agent and in combination (Hopkins, A. L.; Nat. Chem. Biol.; 2008; 4; 682-690).

An alternative strategy for multitarget therapy is to design a single compound with selective polypharmacology (multi-targeting drug). It has been shown that many approved drugs act on multiple targets. Dosing with a single compound may have advantages over a drug combination in terms of equitable pharmacokinetics and biodistribution. Indeed, troughs in drug exposure due to incompatible pharmacokinetics between components of a combination therapy may create a low-dose window of opportunity where a reduced selection pressure can lead to drug resistance. In terms of drug registration, approval of a single compound acting on multiple targets faces significantly lower regulatory barriers than approval of a combination of new drugs (Hopkins, 2008).

Thus, in a preferred embodiment, the compounds of the present invention having affinity for α2δ subunits of voltage-gated calcium channels, preferably towards the α2δ-1 subunit of voltage-gated calcium channels, additionally have inhibitory effect towards the noradrenaline transporter (NET) and are, thus, more effective to treat chronic pain.

There are two potentially important interactions between NET and α2δ-1 inhibition: 1) synergism in analgesia, thus reducing the risk of specific side effects; and 2) inhibition of pain-related affective comorbidities such as anxiety and/or depressive like behaviors (Nicolson et al.; Harv. Rev. Psychiatry; 2009; 17; 407-420).

1) Preclinical research has demonstrated that gabapentinoids attenuated pain-related behaviors through supraspinal activation of the descending noradrenergic system (Tanabe et al.; J. Neuroosci. Res.; 2008; Hayashida, K.; Eur. J. Pharmacol.; 2008; 598; 21-26). In consequence, the α2δ-1-related analgesia mediated by NA-induced activation of spinal α$_2$-adrenergic receptors can be potentiated by the inhibition of the NET. Some evidence from combination studies in preclinical models of neuropathic pain exist. Oral duloxetine with gabapentin was additive to reduce hypersensitivity induced by nerve injury in rats (Hayashida; 2008). The combination of gabapentin and nortriptyline was synergic in mice submitted to orofacial pain and to the peripheral nerve injury model (Miranda, H. F. et al.; J. Orofac. Pain; 2013; 27; 361-366; Pharmacology; 2015; 95; 59-64).

2) Drug modulation of NET and α2δ-1 has been shown to produce antidepressant and anti-anxiety effects respectively (Frampton, J. E.; CNS Drugs; 2014; 28; 835-854; Hajós, M. et al.; CNS Drug Rev.; 2004; 10; 23-44). In consequence, a dual drug that inhibited the NET and α2δ-1 subunit of VGCC may also stabilize pain-related mood impairments by acting directly on both physical pain and the possible mood alterations.

SUMMARY OF THE INVENTION

The present invention discloses novel compounds with great affinity to the α2δ subunit of voltage-gated calcium channels, more specifically to the α2δ-1 subunit, and which in preferred embodiments also have inhibitory effect towards noradrenaline transporter (NET), thus resulting in a dual activity for treating pain and pain related disorders.

The main object of the present invention is related to compounds of general formula (I):

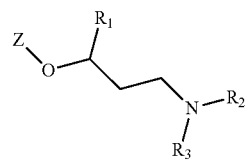

wherein:
Z is one of the following moieties:

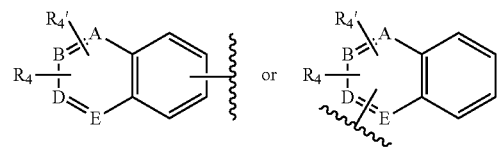

where
R$_4$ and R$_{4'}$ independently represent a hydrogen atom; a branched or unbranched C$_{1-6}$ alkyl radical; a —CN; or a —C(O)NRR' where R and R' independently represent a hydrogen atom or a branched or unbranched C$_{1-6}$ alkyl radical;

A, B, D and E independently from one another represent —N— or —C—; with the proviso that at least one of A, B, D or E is —N—;

R$_1$ is selected from an optionally substituted 5 to 9 membered heteroaryl group having at least one heteroatom selected from the group of N, O or S; or from an optionally substituted 5 to 9 membered heterocycloalkyl group having at least one heteroatom selected from the group of N, O or S;

R$_2$ and R$_3$ independently represent a hydrogen atom; a branched or unbranched C$_{1-6}$ alkyl radical or a benzyl radical;

or a pharmaceutically acceptable salt, isomer, prodrug or solvate thereof.

It is also an object of the invention different processes for the preparation of compounds of formula (I).

Another object of the invention refers to the use of such compounds of general formula (I) for the treatment and/or prophylaxis of α2δ-1 mediated disorders and more preferably for the treatment and/or prophylaxis of disorders mediated by the α2δ-1 subunit of voltage-gated calcium channels and/or noradrenaline transporter (NET). The compounds of the present invention are particularly suited for the treatment of pain, specially neuropathic pain, and pain related or pain derived conditions.

It is also an object of the invention pharmaceutical compositions comprising one or more compounds of general formula (I) with at least one pharmaceutically acceptable excipient. The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

DETAILED DESCRIPTION OF THE INVENTION

The invention first relates to compounds of general formula (I)

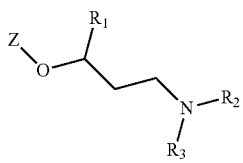
(I)

wherein:
Z is one of the following moieties:

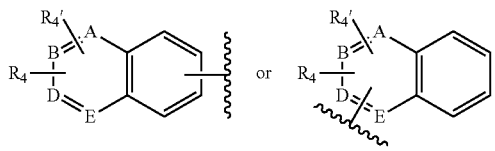

where
R$_4$ and R$_{4'}$ independently represent a hydrogen atom; a branched or unbranched C$_{1-6}$ alkyl radical; a —CN; or a —C(O)NRR' where R and R' independently represent a hydrogen atom or a branched or unbranched C$_{1-6}$ alkyl radical;

A, B, D and E independently from one another represent —N—; or —C—;

with the proviso that at least one of A, B, D or E is —N—;

R$_1$ is selected from an optionally substituted 5 to 9 membered heteroaryl group having at least one heteroatom selected from the group of N, O or S; or from an optionally substituted 5 to 9 membered heterocycloalkyl group having at least one heteroatom selected from the group of N, O or S;

R$_2$ and R$_3$ independently represent a hydrogen atom; a branched or unbranched C$_{1-6}$ alkyl radical or a benzyl radical;

or a pharmaceutically acceptable salt, isomer, prodrug or solvate thereof.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}$C- or $^{14}$C-enriched carbon, or the replacement of at least one nitrogen by $^{15}$N-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

"Halogen" or "halo" as referred in the present invention represent fluorine, chlorine, bromine or iodine. When the term "halo" is combined with other substituents, such as for instance "C$_{1-6}$ haloalkyl" or "C$_{1-6}$ haloalkoxy" it means that the alkyl or alkoxy radical can respectively contain at least one halogen atom.

A leaving group is a group that in a heterolytic bond cleavage keeps the electron pair of the bond. Suitable leaving groups are well known in the art and include Cl, Br, I and —O—SO$_2$R, wherein R is F, C$_{1-4}$-alkyl, C$_{1-4}$-haloalkyl, or optionally substituted phenyl. The preferred leaving groups are Cl, Br, I, tosylate, mesylate, nosylate, triflate, nonaflate and fluorosulphonate.

"C$_{1-6}$ alkyl", as referred to in the present invention, are saturated aliphatic radicals. They may be linear or branched and are optionally substituted. C$_{1-6}$-alkyl as expressed in the present invention means an alkyl radical of 1, 2, 3, 4, 5 or 6 carbon atoms. Preferred alkyl radicals according to the present invention include but are not restricted to methyl, ethyl, propyl, n-propyl, isopropyl, butyl, n-butyl, tert-butyl, isobutyl, sec-butyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl, 1-methylpentyl. The most preferred alkyl radical are C$_{1-4}$ alkyl, such as methyl, ethyl, propyl, n-propyl, isopropyl, butyl, n-butyl, tert-butyl, isobutyl, sec-butyl, 1-methylpropyl, 2-methylpropyl or 1,1-dimethylethyl. Alkyl radicals, as defined in the present invention, are optionally mono- or polysubstituted by substitutents independently selected from a halogen, C$_{1-6}$-alkoxy, C$_{1-6}$-alkyl, C$_{1-6}$-haloalkoxy, C$_{1-6}$-haloalkyl, trihaloalkyl or a hydroxyl group.

"C$_{3-6}$ Cycloalkyl" as referred to in the present invention, is understood as meaning saturated and unsaturated (but not aromatic), cyclic hydrocarbons having from 3 to 6 carbon atoms which can optionally be unsubstituted, mono- or polysubstituted. Examples for cycloalkyl radical preferably include but are not restricted to cyclopropyl, cyclobutyl, cyclopentyl, cyclohexyl. Cycloalkyl radicals, as defined in the present invention, are optionally mono- or polysubstituted by substitutents independently selected from a halogen, C$_{1-6}$-alkyl, C$_{1-6}$-alkoxy, C$_{1-6}$-haloalkoxy, C$_{1-6}$-haloalkyl, trihaloalkyl or a hydroxyl group.

A cycloalkylalkyl group/radical C$_{1-6}$, as defined in the present invention, comprises a linear or branched, optionally at least mono-substituted alkyl chain of 1 to 6 atoms which is bonded to a cycloalklyl group, as defined above. The cycloalkylalkyl radical is bonded to the molecule through the alkyl chain. A preferred cycloalkylalkyl group/radical is a cyclopropylmethyl group or a cyclopentylpropyl group, wherein the alkyl chain is optionally branched or substituted. Preferred substituents for cycloalkylalkyl group/radical, according to the present invention, are independently selected from a halogen, C$_{1-6}$-alkyl, C$_{1-6}$-alkoxy, C$_{1-6}$-haloalkoxy, C$_{1-6}$-haloalkyl, trihaloalkyl or a hydroxyl group.

"Heterocycloalkyl" as referred to in the present invention, are understood as meaning saturated and unsaturated (but not aromatic), generally 5 or 6 membered cyclic hydrocarbons which can optionally be unsubstituted, mono- or polysubstituted and which have at least one heteroatom in their structure selected from N, O or S. Examples for heterocycloalkyl radical preferably include but are not restricted to pyrroline, pyrrolidine, pyrazoline, aziridine, azetidine, tetrahydropyrrole, oxirane, oxetane, dioxetane, tetrahydropyran, tetrahydrofuran, dioxane, dioxolane, oxazolidine, piperidine, piperazine, morpholine, azepane or diazepane. Heterocycloalkyl radicals, as defined in the present invention, are optionally mono- or polysubstituted by substitutents independently selected from a halogen, C$_{1-6}$-alkyl, C$_{1-6}$-alkoxy, C$_{1-6}$-haloalkoxy, C$_{1-6}$-haloalkyl, trihaloalkyl or a hydroxyl group. More preferably heterocycloalkyl in the context of the present invention are 5 or 6-membered ring systems optionally at least monosubstituted.

A heterocycloalkylalkyl group/radical $C_{1-6}$, as defined in the present invention, comprises a linear or branched, optionally at least mono-substituted alkyl chain of 1 to 6 atoms which is bonded to a cycloalklyl group, as defined above. The heterocycloalkylalkyl radical is bonded to the molecule through the alkyl chain. A preferred heterocycloalkylalkyl group/radical is a piperidinethyl group or a piperazinylmethyl group, wherein the alkyl chain is optionally branched or substituted. Preferred substituents for cycloalkylalkyl group/radical, according to the present invention, are independently selected from a halogen, $C_{1-6}$-alkyl, $C_{1-6}$-alkoxy, $C_{1-6}$-haloalkoxy, $C_{1-6}$-haloalkyl, trihaloalkyl or a hydroxyl group.

"Aryl" as referred to in the present invention, is understood as meaning ring systems with at least one aromatic ring but without heteroatoms even in only one of the rings. These aryl radicals may optionally be mono- or polysubstituted by substitutents independently selected from a halogen, $C_{1-6}$-alkyl, $C_{1-6}$-alkoxy, $C_{1-6}$-haloalkoxy, $C_{1-6}$-haloalkyl, nitro or a hydroxyl group. Preferred examples of aryl radicals include but are not restricted to phenyl, naphthyl, fluoranthenyl, fluorenyl, tetralinyl, indanyl or anthracenyl radicals, which may optionally be mono- or polysubstituted, if not defined otherwise. More preferably aryl in the context of the present invention are 5 or 6-membered ring systems optionally at least monosubstituted.

An arylalkyl radical $C_{1-6}$, as defined in the present invention, comprises a linear or branched, optionally at least mono-substituted alkyl chain of 1 to 6 carbon atoms which is bonded to an aryl group, as defined above. The arylalkyl radical is bonded to the molecule through the alkyl chain. A preferred arylalkyl radical is a benzyl group or a phenetyl group, wherein the alkyl chain is optionally branched or substituted. Preferred substituents for arylalkyl radicals, according to the present invention, are independently selected from a halogen, $C_{1-6}$-alkyl, $C_{1-6}$-alkoxy, $C_{1-6}$-haloalkoxy, $C_{1-6}$-haloalkyl, trihaloalkyl or a hydroxyl group.

"Heteroaryl" as referred to in the present invention, is understood as meaning heterocyclic ring systems which have at least one aromatic ring and may optionally contain one or more heteroatoms from the group consisting of N, O or S and may optionally be mono- or polysubstituted by substituents independently selected from a halogen, $C_{1-6}$-alkyl, $C_{1-6}$-alkoxy, $C_{1-6}$-haloalkoxy, $C_{1-6}$-haloalkyl trihaloalkyl or a hydroxyl group. Preferred examples of heteroaryls include but are not restricted to furan, benzofuran, pyrrole, pyridine, pyrimidine, pyridazine, pyrazine, thiophene, quinoline, isoquinoline, phthalazine, triazole, pyrazole, thiazole, isoxazole, indole, benzotriazole, benzodioxolane, benzodioxane, benzimidazole, carbazole and quinazoline. More preferably heteroaryl in the context of the present invention are 5 or 6-membered ring systems optionally at least monosubstituted.

Heteroarylalkyl group/radical $C_{1-6}$ as defined in the present invention, comprises a linear or branched, optionally at least mono-substituted alkyl chain of 1 to 6 carbon atoms which is bonded to an heteroaryl group, as defined above. The heteroarylalkyl radical is bonded to the molecule through the alkyl chain. A preferred heteroarylalkyl radical is a pyridinylmethyl group, wherein the alkyl chain is optionally branched or substituted. Preferred substituents for heteroarylalkyl radicals, according to the present invention, are independently selected from a halogen, $C_{1-6}$-alkyl, $C_{1-6}$-alkoxy, $C_{1-6}$-haloalkoxy, $C_{1-6}$-haloalkyl, trihaloalkyl or a hydroxyl group.

"Heterocyclic ring" or "heterocyclic system", as defined in the present invention, comprise any saturated, unsaturated or aromatic carbocyclic ring systems which are optionally at least mono-substituted and which contain at least one heteroatom as ring member. Preferred heteroatoms for these heterocyclyl groups are N, S or O. Preferred substituents for heterocyclyl radicals, according to the present invention, are F, Cl, Br, I, $NH_2$, SH, OH, $SO_2$, $CF_3$, carboxy, amido, cyano, carbamyl, nitro, phenyl, benzyl, $-SO_2NH_2$, $C_{1-6}$ alkyl and/or $C_{1-6}$-alkoxy.

The term "$C_{1-3}$ alkylene" is understood as meaning a divalent alkyl group like $-CH_2-$ or $-OH_2-OH_2-$ or $-CH_2-OH_2-OH_2-$. An "alkylene" may also be unsaturated The term "condensed" according to the present invention means that a ring or ring-system is attached to another ring or ring-system, whereby the terms "annulated" or "annelated" are also used by those skilled in the art to designate this kind of attachment.

The term "ring system" according to the present invention refers to ring systems comprising saturated, unsaturated or aromatic carbocyclic ring systems which contain optionally at least one heteroatom as ring member and which are optionally at least mono-substituted. Said ring systems may be condensed to other carbocyclic ring systems such as aryl groups, heteroaryl groups, cycloalkyl groups, etc.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions. The definition particularly includes physiologically acceptable salts, this term must be understood as equivalent to "pharmacologically acceptable salts".

The term "pharmaceutically acceptable salts" in the context of this invention means any salt that is tolerated physiologically (normally meaning that it is not toxic, particularly as a result of the counter-ion) when used in an appropriate manner for a treatment, particularly applied or used in humans and/or mammals. These physiologically acceptable salts may be formed with cations or bases and, in the context of this invention, are understood to be salts formed by at least one compound used in accordance with the invention—normally an acid (deprotonated)—such as an anion and at least one physiologically tolerated cation, preferably inorganic, particularly when used on humans and/or mammals. Salts with alkali and alkali earth metals are particularly preferred, as well as those formed with ammonium cations ($NH_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" is to be understood as meaning any form of the active compound according to the invention in which this compound has attached to it via non-covalent binding another molecule (most likely a polar solvent) especially including hydrates and alcoholates, e.g. methanolate.

The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the compounds of the invention: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (april 2002).

Any compound that is a prodrug of a compound of formula (I) is within the scope of the invention. Particularly favored prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

In a particular and preferred embodiment of the invention, $R_1$ represents a thiophene, a thiazole, a pyridine or a tetrahydropyran. These groups may optionally be substituted by at least one substituent selected from halogen, $C_{1-6}$ alkyl, $C_{1-6}$-alkoxy, $C_{1-6}$-haloalkoxy, $C_{1-6}$-haloalkyl or a hydroxyl group. The thiophene, thiazole, pyridine or tetrahydropyran group can be attached to the main structure through different points of attachment. For instance, when $R_1$ represents thiophene this might be a 2-thiophene or 3-thiophene, when it represents thiazole it may represent a 2-thiazole, 4-thiazole or 5-thiazole, when it represents a pyridine it may represent a 2-pyridine, 3-pyridine or 4-pyridine or when it represents tetrahydropyran it may represent 2-tetrahydropyran, 3-tetrahydropyran or 4-tetrahydropyran.

In a particularly preferred embodiment $R_1$ represents a group selected from:

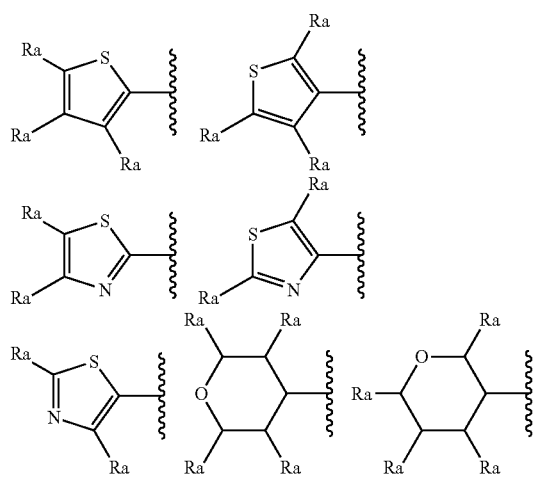

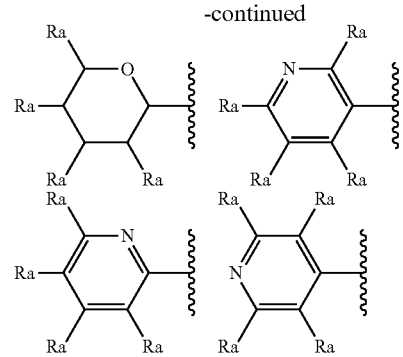

wherein each $R_a$ independently represents a hydrogen atom, a halogen, $C_{1-6}$ alkyl, $C_{1-6}$-alkoxy, $C_{1-6}$-haloalkoxy, $C_{1-6}$-haloalkyl or a hydroxyl group.

In another particular and preferred embodiment of the invention, Z is selected from:

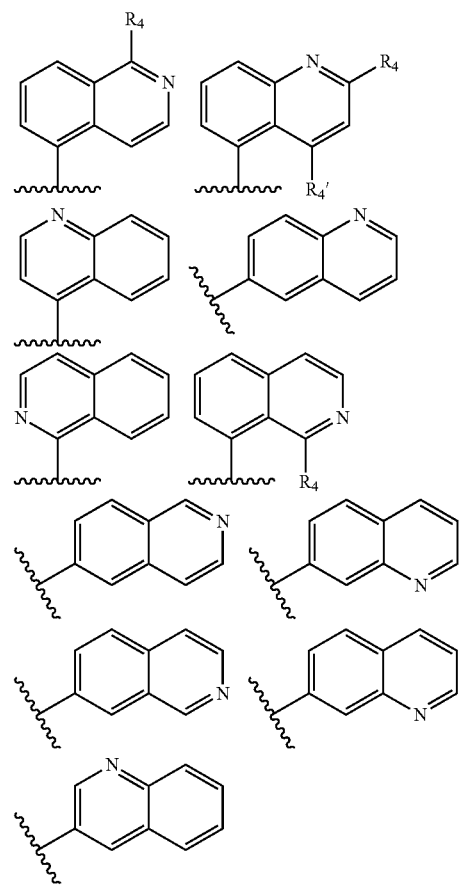

wherein each $R_4$ or $R_{4'}$ independently represent a hydrogen atom; a branched or unbranched $C_{1-6}$ alkyl radical; a —CN; or a —C(O)NRR' where R and R' independently represent a hydrogen atom or a branched or unbranched $C_{1-6}$ alkyl radical.

In another particular and preferred embodiment of the invention $R_2$ and $R_3$ independently represent a hydrogen atom or a branched or unbranched $C_{1-6}$ alkyl radical.

In another particular and preferred embodiment of the invention one of A, B, D and E represents —N— and the others A, B, D and E are —C—.

A preferred embodiment of the invention is represented by compounds of formula (I):

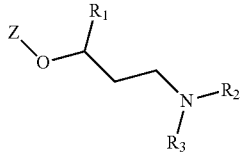

(I)

wherein
Z is selected from:

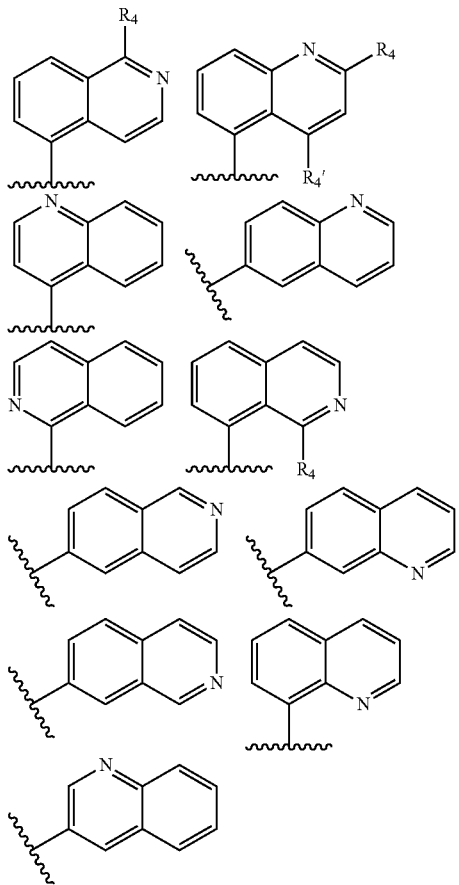

wherein each $R_4$ or $R_{4'}$ independently represent a hydrogen atom; a branched or unbranched $C_{1-6}$ alkyl radical; a —CN; or a —C(O)NRR' where R and R' independently represent a hydrogen atom or a branched or unbranched $C_{1-6}$ alkyl radical;

$R_1$ represents a thiophene, a thiazole, a pyridine or a tetrahydropyran, all of them optionally substituted by at least one substituent selected from selected from a halogen, $C_{1-6}$ alkyl, $C_{1-6}$-alkoxy, $C_{1-6}$-haloalkoxy, $C_{1-6}$-haloalkyl or a hydroxyl group;

$R_2$ and $R_3$ independently represent a hydrogen atom or a branched or unbranched $C_{1-6}$ alkyl radical;

or a pharmaceutically acceptable salt, isomer, prodrug or solvate thereof.

A still more preferred embodiment is represented by compounds of formula (I):

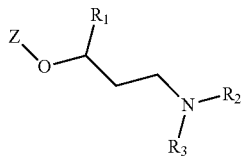

(I)

wherein
Z is selected from:

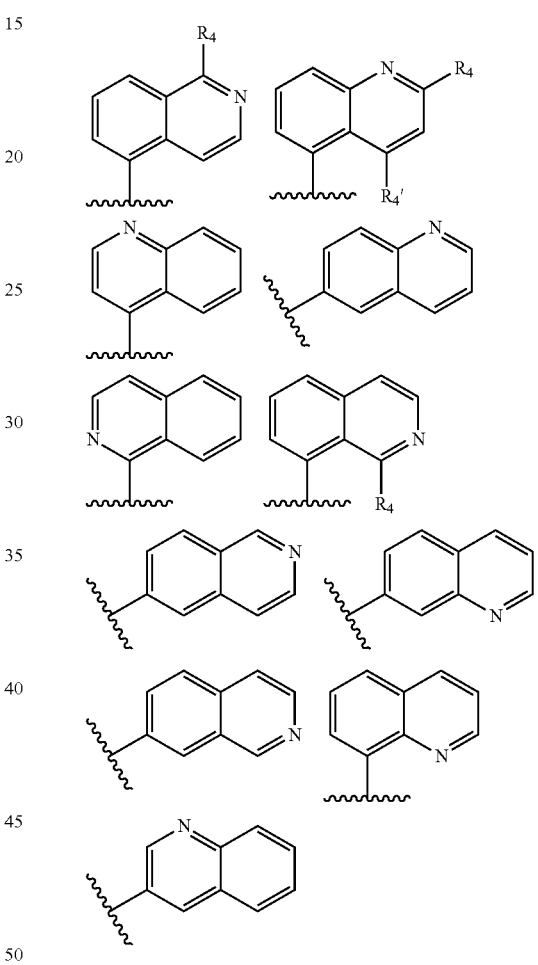

wherein each $R_4$ or $R_{4'}$ independently represent a hydrogen atom; a branched or unbranched $C_{1-6}$ alkyl radical; a —CN; or a —C(O)NRR' where R and R' independently represent a hydrogen atom or a branched or unbranched $C_{1-6}$ alkyl radical;

$R_1$ represents a group selected from:

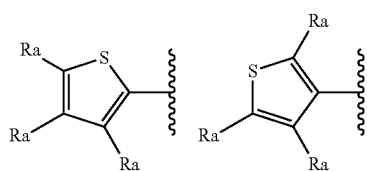

-continued

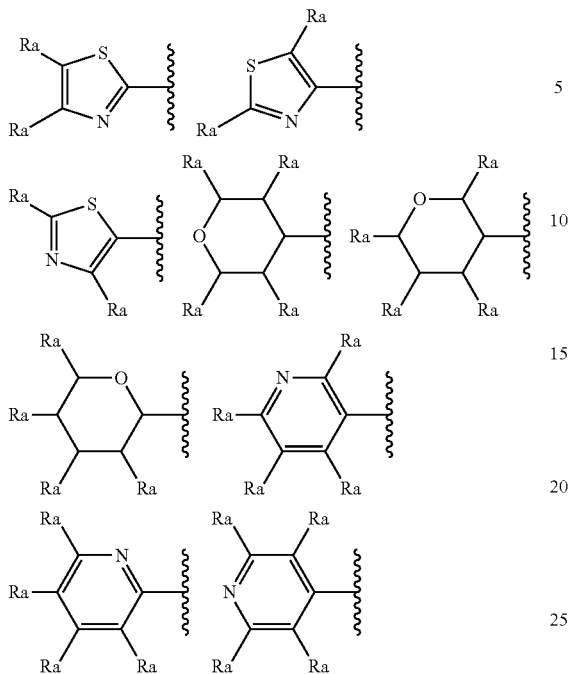

wherein each $R_a$ independently represents a hydrogen atom, a halogen, $C_{1-6}$ alkyl, $C_{1-6}$-alkoxy, $C_{1-6}$-haloalkoxy, $C_{1-6}$-haloalkyl or a hydroxyl group;

$R_2$ and $R_3$ independently represent a hydrogen atom or a branched or unbranched $C_{1-6}$ alkyl radical;

or a pharmaceutically acceptable salt, isomer, prodrug or solvate thereof.

Another particular embodiment of compounds of general formula (I) is represented by compounds having one of the following formula (Iaa), (Iab), (Iba), (Ibb), (Ibc), (Ic) or (Id):

(Iaa)

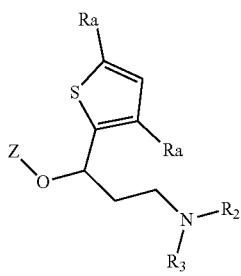

(Iab)

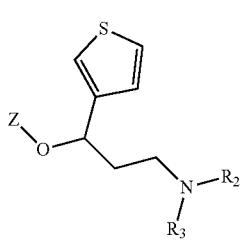

(Iba)

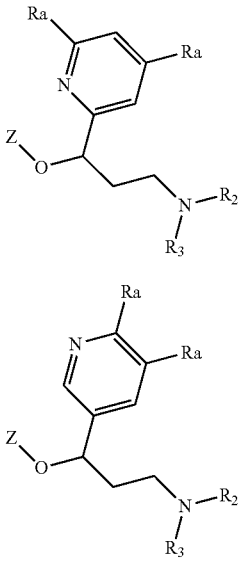

(Ibb)

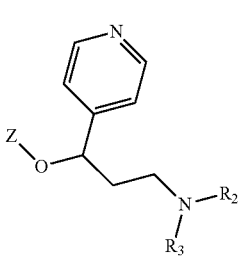

(Ibc)

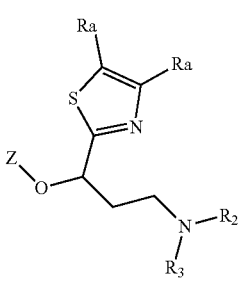

(Ic)

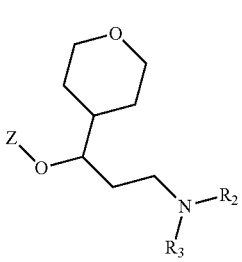

(Id)

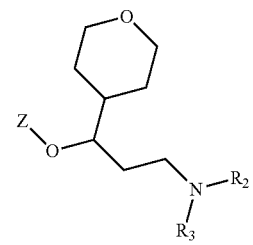

wherein $R_2$, $R_3$ and Z are as defined above and each $R_a$ independently represents a hydrogen atom, a halogen, $C_{1-6}$ alkyl, $C_{1-6}$-alkoxy, $C_{1-6}$-haloalkoxy, $C_{1-6}$-haloalkyl or a hydroxyl group.

The compounds of the present invention represented by the above described formula (I), (Iaa), (Iab), (Iba), (Ibb), (Ibc), (Ic) or (Id) may include enantiomers depending on the presence of chiral centers or isomers depending on the presence of double bonds (e.g. Z, E). The single isomers, enantiomers or diastereoisomers and mixtures thereof fall within the scope of the present invention.

Among all the compounds described in the general formula (I), the following compounds are preferred for showing an intense inhibitory effect towards subunit α2δ-1 of voltage-gated calcium channels (VGCC):

[1] N-methyl-3-(quinolin-8-yloxy)-3-(thiophen-2-yl)propan-1-amine;
[2] N-methyl-3-(quinolin-5-yloxy)-3-(thiophen-2-yl)propan-1-amine;
[3] 3-(Isoquinolin-5-yloxy)-N-methyl-3-(thiophen-2-yl)propan-1-amine;
[4] N-methyl-3-(quinolin-4-yloxy)-3-(thiophen-2-yl)propan-1-amine;
[5] N-ethyl-3-(isoquinolin-5-yloxy)-3-(thiophen-2-yl)propan-1-amine;
[6] N-benzyl-3-(isoquinolin-5-yloxy)-3-(thiophen-2-yl)propan-1-amine;
[7] (R)—N-methyl-3-(quinolin-6-yloxy)-3-(thiophen-2-yl)propan-1-amine;
[8] 3-(Isoquinolin-1-yloxy)-N,N-dimethyl-3-(thiophen-2-yl)propan-1-amine;
[9] (S)—N-methyl-3-(quinolin-5-yloxy)-3-(thiophen-2-yl)propan-1-amine;
[10] (S)-3-(isoquinolin-8-yloxy)-N-methyl-3-(thiophen-2-yl)propan-1-amine;
[11] (S)-3-(isoquinolin-5-yloxy)-N-methyl-3-(thiophen-2-yl)propan-1-amine;
[12] 3-(Isoquinolin-8-yloxy)-N-methyl-3-(thiophen-2-yl)propan-1-amine;
[13] (R)-3-(isoquinolin-8-yloxy)-N-methyl-3-(thiophen-2-yl)propan-1-amine;
[14] (R)-3-(isoquinolin-5-yloxy)-N-methyl-3-(thiophen-2-yl)propan-1-amine;
[15] (R)—N-methyl-3-(quinolin-5-yloxy)-3-(thiophen-2-yl)propan-1-amine;
[16] 5-(3-(Methylamino)-1-(thiophen-2-yl)propoxy)isoquinoline-1-carboxamide;
[17] 3-(Isoquinolin-5-yloxy)-N-methyl-3-(pyridin-3-yl)propan-1-amine;
[18] 3-(Isoquinolin-5-yloxy)-N-methyl-3-(tetrahydro-2H-pyran-4-yl)propan-1-amine;
[19] 3-(Isoquinolin-8-yloxy)-N-methyl-3-(tetrahydro-2H-pyran-4-yl)propan-1-amine;
[20] N-methyl-3-(quinolin-5-yloxy)-3-(tetrahydro-2H-pyran-4-yl)propan-1-amine;
[21] 3-(Isoquinolin-8-yloxy)-N-methyl-3-(pyridin-3-yl)propan-1-amine;
[22] 3-(Isoquinolin-8-yloxy)-N-methyl-3-(pyridin-2-yl)propan-1-amine;
[23] 3-(Isoquinolin-5-yloxy)-N-methyl-3-(pyridin-2-yl)propan-1-amine;
[24] 3-(Isoquinolin-8-yloxy)-N-methyl-3-(6-(trifluoromethyl)pyridin-2-yl)propan-1-amine;
[25] 3-(Isoquinolin-5-yloxy)-N-methyl-3-(pyridin-4-yl)propan-1-amine;
[26] 3-(5-Chloropyridin-3-yl)-3-(isoquinolin-5-yloxy)-N-methylpropan-1-amine;
[27] 3-(Isoquinolin-8-yloxy)-N-methyl-3-(pyridin-4-yl)propan-1-amine;
[28] 3-(Isoquinolin-5-yloxy)-N-methyl-3-(6-(trifluoromethyl)pyridin-3-yl)propan-1-amine;
[29] 3-(Isoquinolin-5-yloxy)-N-methyl-3-(4-(trifluoromethyl)pyridin-2-yl)propan-1-amine;
[30] 3-(Isoquinolin-8-yloxy)-N-methyl-3-(4-(trifluoromethyl)pyridin-2-yl)propan-1-amine;
[31] N-methyl-3-(quinolin-5-yloxy)-3-(4-(trifluoromethyl)pyridin-2-yl)propan-1-amine;
[32] N-methyl-3-(4-methylthiazol-2-yl)-3-(quinolin-5-yloxy)propan-1-amine;
[33] N-methyl-3-(pyridin-2-yl)-3-(quinolin-5-yloxy)propan-1-amine;
[34] N-methyl-3-(5-methylthiazol-2-yl)-3-(quinolin-5-yloxy)propan-1-amine;
[35] N-methyl-3-(pyridin-4-yl)-3-(quinolin-5-yloxy)propan-1-amine;
[36] N-methyl-3-(pyridin-3-yl)-3-(quinolin-5-yloxy)propan-1-amine;
[37] 3-(Isoquinolin-5-yloxy)-N-methyl-3-(6-(trifluoromethyl)pyridin-2-yl)propan-1-amine;
[38] N-methyl-3-(quinolin-5-yloxy)-3-(6-(trifluoromethyl)pyridin-2-yl)propan-1-amine;
[39] 3-(Isoquinolin-8-yloxy)-N-methyl-3-(6-(trifluoromethyl)pyridin-3-yl)propan-1-amine;
[40] N-methyl-3-(quinolin-5-yloxy)-3-(6-(trifluoromethyl)pyridin-3-yl)propan-1-amine;
[41] 3-(5-Chlorothiophen-2-yl)-N-methyl-3-(quinolin-5-yloxy)propan-1-amine;
[42] 3-(5-Fluorothiophen-2-yl)-N-methyl-3-(quinolin-5-yloxy)propan-1-amine;
[43] 3-(Isoquinolin-5-yloxy)-N,N-dimethyl-3-(thiophen-2-yl)propan-1-amine;
[44] 3-(Isoquinolin-5-yloxy)-3-(thiophen-2-yl)propan-1-amine;
[45] 3-(5-Fluorothiophen-2-yl)-3-(isoquinolin-5-yloxy)-N-methylpropan-1-amine;
[46] 3-(3-Fluorothiophen-2-yl)-3-(isoquinolin-5-yloxy)-N-methylpropan-1-amine;
[47] 3-(3-Fluorothiophen-2-yl)-3-(isoquinolin-8-yloxy)-N-methylpropan-1-amine;
[48] 3-(3-Fluorothiophen-2-yl)-N-methyl-3-(quinolin-5-yloxy)propan-1-amine;
[49] 3-(5-Fluorothiophen-2-yl)-3-(isoquinolin-8-yloxy)-N-methylpropan-1-amine;
[50] (S)-3-(5-fluorothiophen-2-yl)-3-(isoquinolin-5-yloxy)-N-methylpropan-1-amine;
[51] (S)-3-(5-fluorothiophen-2-yl)-N-methyl-3-(quinolin-5-yloxy)propan-1-amine;
[52] (R)-3-(5-fluorothiophen-2-yl)-3-(isoquinolin-5-yloxy)-N-methylpropan-1-amine;
[53] (R)-3-(5-fluorothiophen-2-yl)-N-methyl-3-(quinolin-5-yloxy)propan-1-amine;
[54] 3-(Isoquinolin-6-yloxy)-N-methyl-3-(thiophen-2-yl)propan-1-amine;
[55] (S)-3-(isoquinolin-6-yloxy)-N-methyl-3-(thiophen-2-yl)propan-1-amine;
[56] 3-(Isoquinolin-5-yloxy)-N-methyl-3-(thiophen-3-yl)propan-1-amine;
[57] N-methyl-3-(quinolin-5-yloxy)-3-(thiophen-3-yl)propan-1-amine;
[58] 3-(Isoquinolin-8-yloxy)-N-methyl-3-(thiophen-3-yl)propan-1-amine;
[59] (R)—N-methyl-3-((1-methylisoquinolin-5-yl)oxy)-3-(thiophen-2-yl)propan-1-amine;
[60] (R)-3-(isoquinolin-5-yloxy)-N-methyl-3-(thiophen-3-yl)propan-1-amine;
[61] (R)-3-(isoquinolin-8-yloxy)-N-methyl-3-(thiophen-3-yl)propan-1-amine;
[62] (R)—N-methyl-3-((1-methylisoquinolin-8-yl)oxy)-3-(thiophen-2-yl)propan-1-amine;
[63] (R)—N-methyl-3-(quinolin-5-yloxy)-3-(thiophen-3-yl)propan-1-amine;
[64] (S)—N-methyl-3-((1-methylisoquinolin-8-yl)oxy)-3-(thiophen-2-yl)propan-1-amine;

[65] (S)—N-methyl-3-((1-methylisoquinolin-5-yl)oxy)-3-(thiophen-2-yl)propan-1-amine;
[66] (R)-3-((2,4-dimethylquinolin-5-yl)oxy)-N-methyl-3-(thiophen-2-yl)propan-1-amine;
[67] (S)—N-methyl-3-(quinolin-5-yloxy)-3-(thiophen-3-yl)propan-1-amine;
[68] (S)-3-(isoquinolin-5-yloxy)-N-methyl-3-(thiophen-3-yl)propan-1-amine;
[69] (S)-3-(isoquinolin-8-yloxy)-N-methyl-3-(thiophen-3-yl)propan-1-amine;
[70] 3-(Isoquinolin-8-yloxy)-N-methyl-3-(thiazol-2-yl)propan-1-amine;
[71] 3-(Isoquinolin-5-yloxy)-N-methyl-3-(thiazol-2-yl)propan-1-amine;
[72] N-methyl-3-(quinolin-5-yloxy)-3-(thiazol-2-yl)propan-1-amine;
[73] N-methyl-3-(quinolin-7-yloxy)-3-(thiophen-2-yl)propan-1-amine;
[74] 3-(Isoquinolin-7-yloxy)-N-methyl-3-(thiophen-2-yl)propan-1-amine;
[75] 5-(3-(Methylamino)-1-(thiophen-2-yl)propoxy)isoquinoline-1-carbonitrile;
[76] (S)—N-methyl-3-(quinolin-5-yloxy)-3-(thiazol-2-yl)propan-1-amine;
[77] (R)—N-methyl-3-(quinolin-5-yloxy)-3-(thiazol-2-yl)propan-1-amine;
[78] (S)-3-(5-chlorothiophen-2-yl)-N-methyl-3-(quinolin-5-yloxy)propan-1-amine;
[79] (R)-3-(5-chlorothiophen-2-yl)-N-methyl-3-(quinolin-5-yloxy)propan-1-amine;
[80] (S)-3-(5-fluorothiophen-2-yl)-3-(isoquinolin-8-yloxy)-N-methylpropan-1-amine;
[81] (R)-3-(5-fluorothiophen-2-yl)-3-(isoquinolin-8-yloxy)-N-methylpropan-1-amine;
[82] (S)-3-(3-fluorothiophen-2-yl)-3-(isoquinolin-5-yloxy)-N-methylpropan-1-amine;
[83] (R)-3-(3-fluorothiophen-2-yl)-3-(isoquinolin-5-yloxy)-N-methylpropan-1-amine;
[84] (S)-3-(3-fluorothiophen-2-yl)-N-methyl-3-(quinolin-5-yloxy)propan-1-amine;
[85] (R)-3-(3-fluorothiophen-2-yl)-N-methyl-3-(quinolin-5-yloxy)propan-1-amine;
[86] (S)-3-(3-fluorothiophen-2-yl)-3-(isoquinolin-8-yloxy)-N-methylpropan-1-amine;
[87] (R)-3-(3-fluorothiophen-2-yl)-3-(isoquinolin-8-yloxy)-N-methylpropan-1-amine;
[88] (R)—N-ethyl-3-(isoquinolin-5-yloxy)-3-(thiophen-2-yl)propan-1-amine;
[89] (R)-5-(3-(ethylamino)-1-(thiophen-2-yl)propoxy)isoquinoline-1-carbonitrile;
[90] (S)—N-ethyl-3-(quinolin-5-yloxy)-3-(thiophen-2-yl)propan-1-amine;
[91] (S)-5-(3-(ethylamino)-1-(thiophen-2-yl)propoxy)isoquinoline-1-carbonitrile;
[92] (S)—N-ethyl-3-(isoquinolin-5-yloxy)-3-(thiophen-2-yl)propan-1-amine;
[93] (R)—N-ethyl-3-(quinolin-5-yloxy)-3-(thiophen-2-yl)propan-1-amine;
[94] (R)—N-methyl-3-(quinolin-3-yloxy)-3-(thiophen-2-yl)propan-1-amine and
[95] (S)—N-methyl-3-(quinolin-3-yloxy)-3-(thiophen-2-yl)propan-1-amine;
or a pharmaceutically acceptable salt, prodrug or solvate thereof.

Among compounds of general formula (I) some subgroups of compounds have shown in addition a dual affinity towards subunit α2δ-1 of voltage-gated calcium channels (VGCC) and noradrenaline transporter (NET). These compounds having dual affinity represent the preferred embodiments of the invention and are represented by formulas (Iaa1), (Iaa2), (Iaa3), (Iaa4), (Iab1), (Iab2), (Iab3), (Iab4), (Iab5), (Iba1), (Ibb1), (Ibc1), (Ic1), (Ic2) or (Id1):

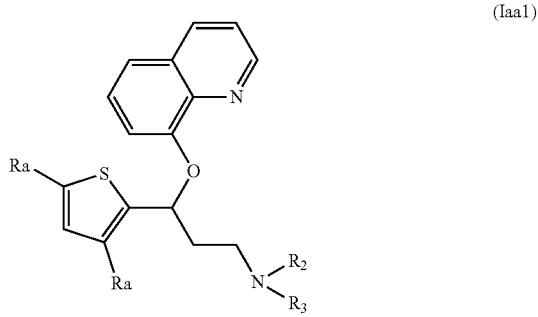

(Iaa1)

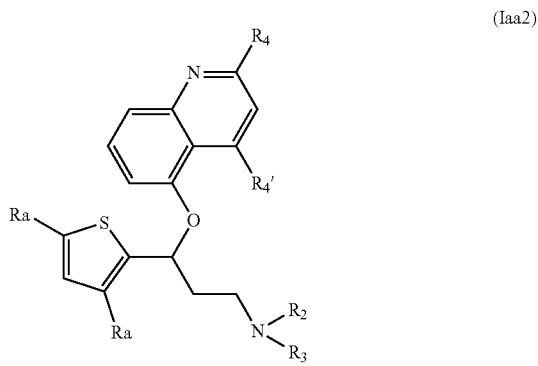

(Iaa2)

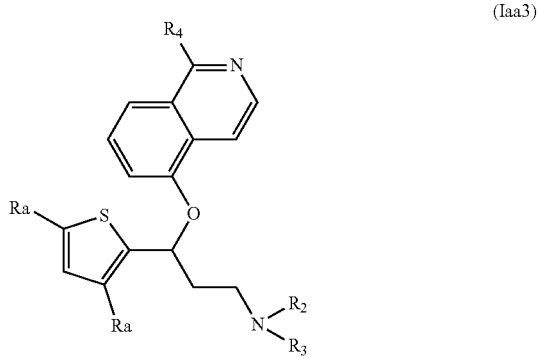

(Iaa3)

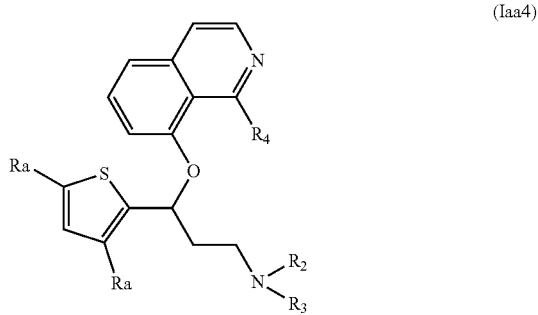

(Iaa4)

(Iab1)
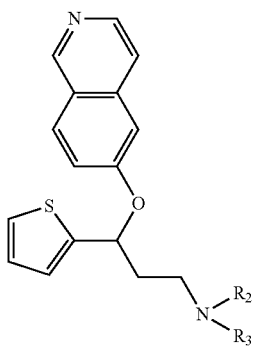
(Iab2)
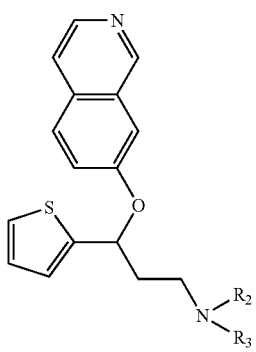
(Iab3)
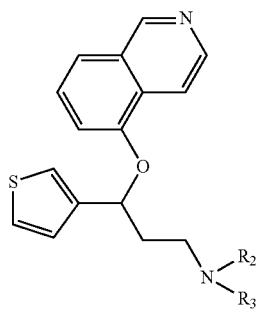
(Iab4)
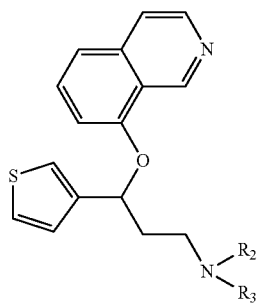
(Iab5)
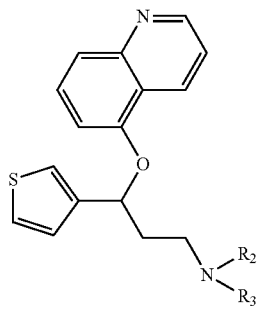
(Iba1)
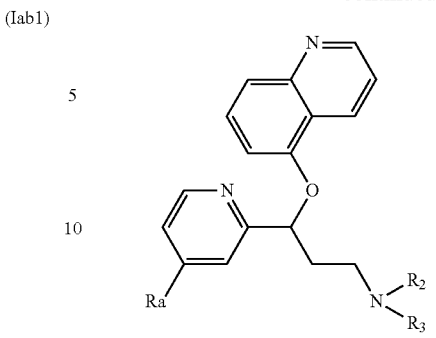
(Ibb1)
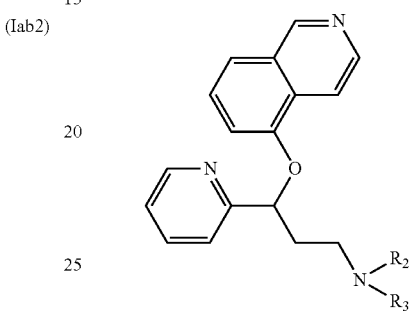
(Ibc1)
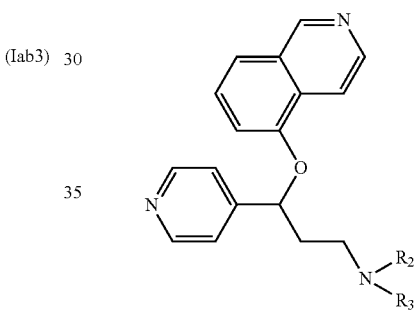
(Ic1)
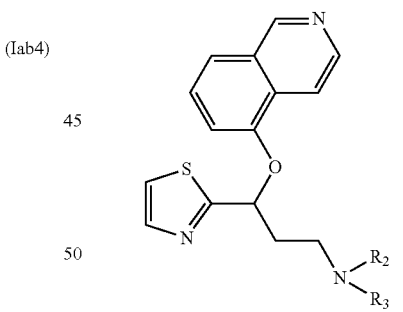
(Ic2)
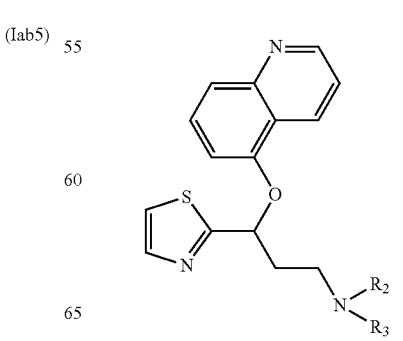

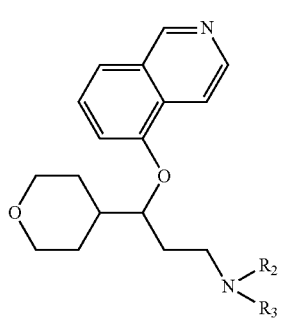

(Id1)

wherein R$_2$, R$_3$, R$_4$ and R'$_4$ are as defined above and each R$_a$ independently represents a hydrogen atom, a halogen, C$_{1-6}$ alkyl, C$_{1-6}$-alkoxy, C$_{1-6}$-haloalkoxy, C$_{1-6}$-haloalkyl or a hydroxyl group.

The preferred compounds of the invention showing dual inhibitory effect towards subunit α2δ-1 of voltage-gated calcium channels (VGCC) and noradrenaline transporter (NET) are selected from the following group:

[1] N-methyl-3-(quinolin-8-yloxy)-3-(thiophen-2-yl)propan-1-amine;
[2] N-methyl-3-(quinolin-5-yloxy)-3-(thiophen-2-yl)propan-1-amine;
[3] 3-(Isoquinolin-5-yloxy)-N-methyl-3-(thiophen-2-yl)propan-1-amine;
[9] (S)—N-methyl-3-(quinolin-5-yloxy)-3-(thiophen-2-yl)propan-1-amine;
[10] (S)-3-(isoquinolin-8-yloxy)-N-methyl-3-(thiophen-2-yl)propan-1-amine;
[11] (S)-3-(isoquinolin-5-yloxy)-N-methyl-3-(thiophen-2-yl)propan-1-amine;
[12] 3-(Isoquinolin-8-yloxy)-N-methyl-3-(thiophen-2-yl)propan-1-amine;
[13] (R)-3-(isoquinolin-8-yloxy)-N-methyl-3-(thiophen-2-yl)propan-1-amine;
[14] (R)-3-(isoquinolin-5-yloxy)-N-methyl-3-(thiophen-2-yl)propan-1-amine;
[15] (R)—N-methyl-3-(quinolin-5-yloxy)-3-(thiophen-2-yl)propan-1-amine;
[17] 3-(Isoquinolin-5-yloxy)-N-methyl-3-(pyridin-3-yl)propan-1-amine;
[18] 3-(Isoquinolin-5-yloxy)-N-methyl-3-(tetrahydro-2H-pyran-4-yl)propan-1-amine;
[25] 3-(Isoquinolin-5-yloxy)-N-methyl-3-(pyridin-4-yl)propan-1-amine;
[30] 3-(Isoquinolin-8-yloxy)-N-methyl-3-(4-(trifluoromethyl)pyridin-2-yl)propan-1-amine;
[41] 3-(5-Chlorothiophen-2-yl)-N-methyl-3-(quinolin-5-yloxy)propan-1-amine;
[42] 3-(5-Fluorothiophen-2-yl)-N-methyl-3-(quinolin-5-yloxy)propan-1-amine;
[44] 3-(Isoquinolin-5-yloxy)-3-(thiophen-2-yl)propan-1-amine;
[45] 3-(5-Fluorothiophen-2-yl)-3-(isoquinolin-5-yloxy)-N-methylpropan-1-amine;
[46] 3-(3-Fluorothiophen-2-yl)-3-(isoquinolin-5-yloxy)-N-methylpropan-1-amine;
[47] 3-(3-Fluorothiophen-2-yl)-3-(isoquinolin-8-yloxy)-N-methylpropan-1-amine;
[48] 3-(3-Fluorothiophen-2-yl)-N-methyl-3-(quinolin-5-yloxy)propan-1-amine;
[49] 3-(5-Fluorothiophen-2-yl)-3-(isoquinolin-8-yloxy)-N-methylpropan-1-amine;
[50] (S)-3-(5-fluorothiophen-2-yl)-3-(isoquinolin-5-yloxy)-N-methylpropan-1-amine;
[51] (S)-3-(5-fluorothiophen-2-yl)-N-methyl-3-(quinolin-5-yloxy)propan-1-amine;
[52] (R)-3-(5-fluorothiophen-2-yl)-3-(isoquinolin-5-yloxy)-N-methylpropan-1-amine;
[53] (R)-3-(5-fluorothiophen-2-yl)-N-methyl-3-(quinolin-5-yloxy)propan-1-amine;
[54] 3-(Isoquinolin-6-yloxy)-N-methyl-3-(thiophen-2-yl)propan-1-amine;
[56] 3-(Isoquinolin-5-yloxy)-N-methyl-3-(thiophen-3-l1)propan-1-amine;
[58] 3-(Isoquinolin-8-yloxy)-N-methyl-3-(thiophen-3-l1)propan-1-amine;
[60] (R)-3-(isoquinolin-5-yloxy)-N-methyl-3-(thiophen-3-yl)propan-1-amine;
[61] (R)-3-(isoquinolin-8-yloxy)-N-methyl-3-(thiophen-3-yl)propan-1-amine;
[62] (R)—N-methyl-3-((1-methylisoquinolin-8-yl)oxy)-3-(thiophen-2-yl)propan-1-amine;
[65] (S)—N-methyl-3-((1-methylisoquinolin-5-yl)oxy)-3-(thiophen-2-yl)propan-1-amine;
[66] (R)-3-((2,4-dimethylquinolin-5-yl)oxy)-N-methyl-3-(thiophen-2-yl)propan-1-amine;
[67] (S)—N-methyl-3-(quinolin-5-yloxy)-3-(thiophen-3-yl)propan-1-amine;
[68] (S)-3-(isoquinolin-5-yloxy)-N-methyl-3-(thiophen-3-yl)propan-1-amine;
[69] (S)-3-(isoquinolin-8-yloxy)-N-methyl-3-(thiophen-3-yl)propan-1-amine;
[71] 3-(Isoquinolin-5-yloxy)-N-methyl-3-(thiazol-2-yl)propan-1-amine;
[72] N-methyl-3-(quinolin-5-yloxy)-3-(thiazol-2-yl)propan-1-amine;
[74] 3-(Isoquinolin-7-yloxy)-N-methyl-3-(thiophen-2-yl)propan-1-amine;
[78] (S)-3-(5-chlorothiophen-2-yl)-N-methyl-3-(quinolin-5-yloxy)propan-1-amine;
[79] (R)-3-(5-chlorothiophen-2-yl)-N-methyl-3-(quinolin-5-yloxy)propan-1-amine;
[81] (R)-3-(5-fluorothiophen-2-yl)-3-(isoquinolin-8-yloxy)-N-methylpropan-1-amine;
[82] (S)-3-(3-fluorothiophen-2-yl)-3-(isoquinolin-5-yloxy)-N-methylpropan-1-amine;
[83] (R)-3-(3-fluorothiophen-2-yl)-3-(isoquinolin-5-yloxy)-N-methylpropan-1-amine;
[84] (S)-3-(3-fluorothiophen-2-yl)-N-methyl-3-(quinolin-5-yloxy)propan-1-amine;
[85] (R)-3-(3-fluorothiophen-2-yl)-N-methyl-3-(quinolin-5-yloxy)propan-1-amine;
[86] (S)-3-(3-fluorothiophen-2-yl)-3-(isoquinolin-8-yloxy)-N-methylpropan-1-amine;
[87] (R)-3-(3-fluorothiophen-2-yl)-3-(isoquinolin-8-yloxy)-N-methylpropan-1-amine and
[94] (R)—N-methyl-3-(quinolin-3-yloxy)-3-(thiophen-2-yl)propan-1-amine;

or a pharmaceutically acceptable salt, prodrug or solvate thereof.

In another aspect, the invention refers to the processes for the preparation of the compounds of general formula (I):

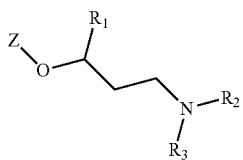

(I)

Comprising
A) the reaction of a compound of formula (II):

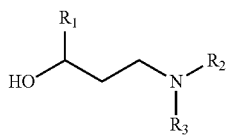

(II)

with a compound of formula (IIIa) or (IIIb):

   (IIIa)

or

   (IIIb)

wherein $R_1$, $R_2$, $R_3$ and Z are as defined in claim 1 and X represents a halogen, or
B) the reaction of a compound of formula (V):

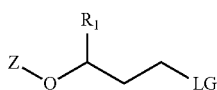

(V)

with a compound of formula (VI):

   (VI)

wherein $R_1$, $R_2$, $R_3$ and Z are as defined in claim 1 and LG represents a leaving group, such as chloro, bromo, iodo, mesylate, tosylate, nosylate or triflate.

The obtained reaction products may, if desired, be purified by conventional methods, such as crystallization and chromatography. Where the processes described for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

Different reaction conditions are applied when the compounds of formula (I) are synthesized through the reaction of a compound of formula (II) with either a compound of formula (IIIa) or a compound of formula (IIIb):

a) When a hydroxy compound of formula (IIIa) is used, the reaction is carried out under conventional Mitsunobu conditions by treating an alcohol of formula II with a compound of formula IIIa preferably in the presence of an azo compound such as 1,1'-(azodicarbonyl)dipiperidine (ADDP), diisopropylazodicarboxylate (DIAD) or diethyl azodicarboxylate (DEAD) and a phosphine such as tributylphosphine or triphenylphoshine. The Mitsunobu reaction is carried out in a suitable solvent, such as toluene or tetrahydrofuran; at a suitable temperature comprised between room temperature and the reflux temperature, preferably heating, or alternatively, the reactions can be carried out in a microwave reactor.

b) When a halo compound of formula (IIIb) is used, the reaction is carried out under conventional aromatic nucleophilic substitution conditions by treating an alcohol of formula (II) with a compound of formula (IIIb) wherein X represents halogen (preferably fluoro), in the presence of a strong base such as sodium hydride or potassium tert-butoxide. The reaction is carried out in a suitable solvent, such as a polar aprotic solvent, preferably dimethylformamide, dimethylacetamide or dimethylsulfoxide; at a suitable temperature comprised between room temperature and the reflux temperature, preferably heating, or alternatively, the reactions can be carried out in a microwave reactor. Alternatively, when X is bromo or iodo, the compound of formula (IIIb) can be introduced under cross-coupling conditions, using a Pd or Cu catalyst and a suitable ligand.

Alternatively and, as explained above, a compound of formula (I) can be obtained by reaction of a compound of formula (V) with a compound of formula (VI). The alkylation reaction is carried out in a suitable solvent, such as ethanol, dimethylformamide, dimethylsulfoxide or acetonitrile, preferably ethanol; optionally in the presence of a base such as $K_2CO_3$ or triethylamine; at a suitable temperature comprised between room temperature and the reflux temperature, preferably heating, or alternatively, the reactions can be carried out in a microwave reactor. Additionally, an activating agent such as sodium iodide or potassium iodide can be used.

The processes of the invention use a compound of formula (II) as starting material. The amino group can be either introduced in a compound of formula (II) at an early stage, that is, before the reaction for producing compounds of formula (I) or later in the synthesis by reaction of a compound of formula (II)-LG or (V) wherein LG represents a leaving group (such as chloro, bromo, iodo, mesylate, tosylate, nosylate or triflate) with an amine of formula (VI) to render a compound of formula (II) or (I), respectively, as shown in Scheme 1 below. The alkylation reaction is carried out in a suitable solvent, such as ethanol, dimethylformamide, dimethylsulfoxide or acetonitrile, preferably ethanol; optionally in the presence of a base such as $K_2CO_3$ or triethylamine; at a suitable temperature comprised between room temperature and the reflux temperature, preferably heating, or alternatively, the reactions can be carried out in a microwave reactor. Additionally, an activating agent such as sodium iodide or potassium iodide can be used.

The different reactions of the synthetic process of the invention as well as the reactions for preparing the intermediate compounds for such reactions are depicted in scheme 1:

Scheme 1

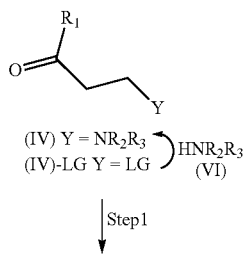

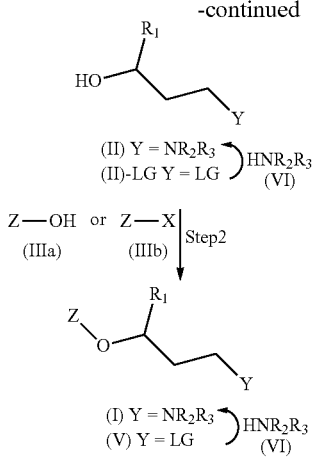

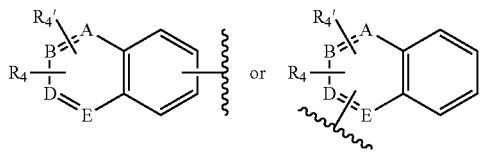

wherein Z can be

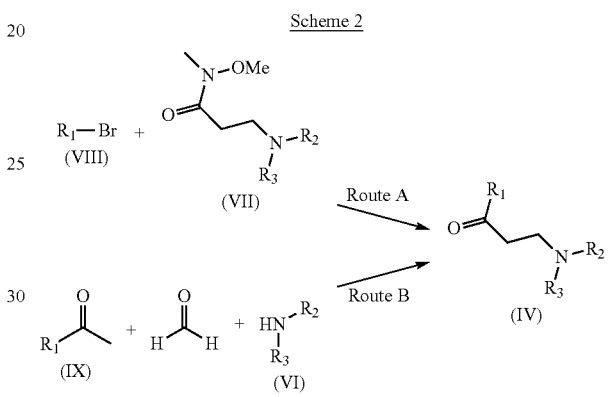

The intermediate compound (II) which is the basic reagent for producing compounds of formula (I) can be prepared by reduction of a keto compound of formula (IV) following conventional procedures described in the literature. As a way of example, the reduction can be performed using a hydride source such as sodium borohydride in a suitable solvent such as methanol, ethanol or tetrahydrofuran or lithium aluminium hydride in a suitable solvent such as tetrahydrofuran or diethyl ether, at a suitable temperature, preferably comprised between 0° C. and room temperature.

Alternatively, the reduction can be carried out by hydrogenation under hydrogen atmosphere and metal catalysis, preferably by the use of palladium over charcoal or Nickel-Raney as catalysts, in a suitable solvent such as methanol, ethanol or ethyl acetate. In addition, the reduction can be performed under asymmetric hydrogenation conditions using a rhodium catalyst to render chiral compounds of formula (II) in enantiopure form, following procedures described in the literature (i.e. *Angew. Chem. Int. Ed.* 2004, 43, 2816; *Angew. Chem. Int. Ed.* 2005, 44, 1687; *Angew. Chem. Int. Ed.* 2015, 54, 2260)

A compound of formula (V), can be synthesized from a compound of formula (II)-LG by reaction with a compound of formula (IIIa), following the conditions described above for the preparation of a compound of formula (I) from a compound of formula (II) and a compound of formula (IIIa).

The compounds of general formula (IIIa), (IIIb) and (VI) are commercially available or can be prepared by conventional methods described in the bibliography.

The compounds of formula (II)-LG are commercially available or can be obtained from a compound of formula (IV)-LG following the reduction conditions described above (Step 1), preferably using a hydride source. In addition, the reduction can be performed under asymmetric conditions described in the literature to render chiral compounds of formula (II)-LG in enantiopure form. As a way of example, the chiral reduction can be performed using a hydride source such as borane-tetrahydrofuran complex or borane-dimethyl sulfide complex, in the presence of a Corey-Bakshi-Shibata oxazaborolidine catalyst, in a suitable solvent such as tetrahydrofuran or toluene, at a suitable temperature, preferably comprised between 0° C. and room temperature.

In turn, compounds of formula (IV) and (IV)-LG are commercially available or can be synthesized following procedures described in the literature. As a way of example, some routes of synthesis are described in Schemes 2 and 3 below. In addition, a compound of formula (IV) can be prepared from a compound of formula (IV)-LG and an amine of formula (VI) following the conditions described above for the synthesis of a compound of formula (I) from a compound of formula (V).

The preparation of compounds of general formula IV can be performed following several methods described in the literature. As a way of example, two routes of synthesis are described in Scheme 2:

Scheme 2

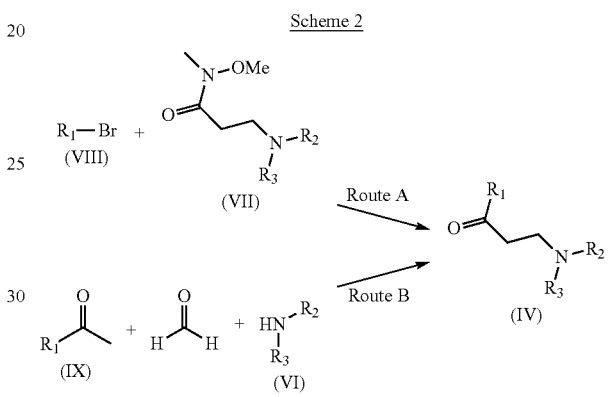

wherein $R_1$, $R_2$ and $R_3$ have the meanings as defined above for a compound of formula (I).

Following Route A, the treatment of a compound of formula (VIII) with a strong base such as butyl lithium to generate the corresponding organometallic reagent and subsequent condensation with a Weinreb amide of formula (VII), in a suitable solvent such as tetrahydrofuran, renders a compound of formula (IV).

Alternatively, the compounds of formula (IV) can be prepared through a Mannich reaction by condensation of an acetyl compound of formula (IX) with an amine of formula (VI) and a formaldehyde source such as paraformaldehyde, preferably in the presence of an acid such as hydrochloric acid, in a suitable solvent such as ethanol or isopropanol, at a suitable temperature, preferably heating.

The preparation of compounds of general formula (IV)-LG can be performed following several methods described in the literature. As a way of example, a route of synthesis is described in Scheme 3:

Scheme 3

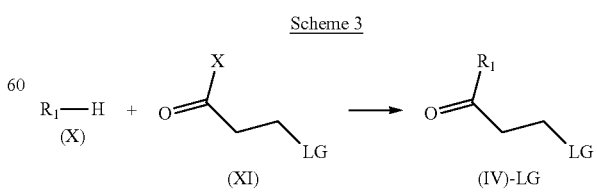

wherein $R_1$ has the meaning as defined above for a compound of formula (I), LG represents a leaving group (preferably chloro, bromo or iodo) and (X) represents halogen (preferably chloro or bromo).

The Friedel-Crafts acylation of an heteroaryl compound of formula (X) with an acid halide of formula (XI) in the presence of a Lewis acid such as aluminum trichloride renders a compound of formula (IV-LG). The reaction is carried out in a suitable solvent, such as dichloromethane or dichloroethane; at a suitable temperature comprised between 0° C. and the reflux temperature.

The compounds of general formula (VI), (VII), (VIII), (IX), (X) and (XI) are commercially available or can be prepared by conventional methods described in the bibliography.

Moreover, certain compounds of the present invention can also be obtained starting from other compounds of formula (I) by appropriate conversion reactions of functional groups, in one or several steps, using well-known reactions in organic chemistry under standard experimental conditions.

In some of the processes described above it may be necessary to protect the reactive or labile groups present with suitable protecting groups, such as for example Boc (tert-butoxycarbonyl), Teoc (2-(trimethylsilyl)ethoxycarbonyl) or benzyl for the protection of amino groups. The procedures for the introduction and removal of these protecting groups are well known in the art and can be found thoroughly described in the literature.

In addition, a compound of formula (I) that shows chirality can also be obtained by resolution of a racemic compound of formula I either by chiral preparative HPLC or by crystallization of a diastereomeric salt or co-crystal. Alternatively, the resolution step can be carried out at a previous stage, using any suitable intermediate.

Another particular aspect is represented by the intermediate compounds used for the preparation of compounds of general formula (I).

In a particular embodiment, these intermediate compounds are selected from:
3-(Methylamino)-1-(6-(trifluoromethyl)pyridin-2-yl)propan-1-ol;
tert-Butyl (3-hydroxy-3-(thiazol-2-yl)propyl)(methyl)carbamate;
1-(5-Chloropyridin-3-yl)-3-(methylamino)propan-1-ol;
3-(Methylamino)-1-(6-(trifluoromethyl)pyridin-3-yl)propan-1-ol;
3-(Methylamino)-1-(4-(trifluoromethyl)pyridin-2-yl)propan-1-ol;
3-(Methylamino)-1-(4-methylthiazol-2-yl)propan-1-ol;
3-(Methylamino)-1-(5-methylthiazol-2-yl)propan-1-ol;
1-(3-Fluorothiophen-2-yl)-3-(methylamino)propan-1-ol;
1-(5-Fluorothiophen-2-yl)-3-(methylamino)propan-1-ol;
3-(Methylamino)-1-(thiophen-3-yl)propan-1-ol;
3-(Methylamino)-1-(thiophen-2-yl)propan-1-ol;
(R)-1-(5-fluorothiophen-2-yl)-3-(methylamino)propan-1-ol;
(S)-1-(5-fluorothiophen-2-yl)-3-(methylamino)propan-1-ol;
(R)-3-(methylamino)-1-(thiophen-3-yl)propan-1-ol;
(S)-3-(methylamino)-1-(thiophen-3-yl)propan-1-ol;
tert-Butyl (3-hydroxy-3-(thiophen-2-yl)propyl)(methyl)carbamate;
5-Fluoro-2,4-dimethylquinoline;

Turning to another aspect, the invention also relates to the therapeutic use of the compounds of general formula (I). As mentioned above, compounds of general formula (I) show a strong affinity to subunit an and, more preferably, to α2δ-1 subunit of voltage-gated calcium channels. In a more preferred embodiment of the invention compounds of general formula (I) show a strong affinity both to subunit an and, more preferably, to α2δ-1 subunit of voltage-gated calcium channels, as well as to noradrenaline transporter (NET) and can behave as agonists, antagonists, inverse agonists, partial antagonists or partial agonists thereof. Therefore, compounds of general formula (I) are useful as medicaments.

They are suitable for the treatment and/or prophylaxis of diseases and/or disorders mediated by the subunit an, especially α2δ-1 subunit of voltage-gated calcium channels and/or noradrenaline transporter (NET). In this sense, compounds of formula (I) are suitable for the treatment and/or prophylaxis of pain, depression anxiety and attention-deficit-/hyperactivity disorder (ADHD).

The compounds of formula (I) are especially suited for the treatment of pain, especially medium to severe pain, visceral pain, chronic pain, cancer pain, migraine, inflammatory pain, acute pain neuropathic pain, allodynia or hyperalgesia, including mechanical allodynia or thermal hyperalgesia.

PAIN is defined by the International Association for the Study of Pain (IASP) as "an unpleasant sensory and emotional experience associated with actual or potential tissue damage, or described in terms of such damage (IASP, Classification of chronic pain, 2nd Edition, IASP Press (2002), 210). Even though pain is always subjective its causes or syndromes can be classified.

In a preferred embodiment compounds of the invention are used for the treatment and/or prophylaxis of allodynia and more specifically mechanical or thermal allodynia.

In another preferred embodiment compounds of the invention are used for the treatment and/or prophylaxis of hyperalgesia.

In yet another preferred embodiment compounds of the invention are used for the treatment and/or prophylaxis of neuropathic pain and more specifically for the treatment and/or prophylaxis of hyperpathia.

A related aspect of the invention refers to the use of compounds of formula (I) for the manufacture of a medicament for the treatment and/or prophylaxis of disorders and diseases mediated by the subunit an, especially α2δ-1 subunit of voltage-gated calcium channels and/or noradrenaline transporter (NET), as explained before.

Another related aspect of the invention refers to a method for the treatment and/or prophylaxis of disorders and diseases mediated by the subunit an, especially α2δ-1 subunit of voltage-gated calcium channels and/or noradrenaline transporter (NET), as explained before comprising the administration of a therapeutically effective amount of a compound of general formula (I) to a subject in need thereof.

Another aspect of the invention is a pharmaceutical composition, which comprises at least a compound of general formula (I) or a pharmaceutically acceptable salt, prodrug, isomer or solvate thereof, and at least a pharmaceutically acceptable carrier, additive, adjuvant or vehicle.

The pharmaceutical composition of the invention can be formulated as a medicament in different pharmaceutical forms comprising at least a compound binding to the subunit an, especially α2δ-1 subunit of voltage-gated calcium channels and/or noradrenaline transporter (NET) and optionally at least one further active substance and/or optionally at least one auxiliary substance.

The auxiliary substances or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously.

Preferably, the composition is suitable for oral or parenteral administration, more preferably for oral, intravenous, intraperitoneal, intramuscular, subcutaneous, intrathekal, rectal, transdermal, transmucosal or nasal administration.

The composition of the invention can be formulated for oral administration in any form preferably selected from the group consisting of tablets, dragees, capsules, pills, chewing gums, powders, drops, gels, juices, syrups, solutions and suspensions. The composition of the present invention for oral administration may also be in the form of multiparticulates, preferably microparticles, microtablets, pellets or granules, optionally compressed into a tablet, filled into a capsule or suspended in a suitable liquid. Suitable liquids are known to those skilled in the art.

Suitable preparations for parenteral applications are solutions, suspensions, reconstitutable dry preparations or sprays.

The compounds of the invention can be formulated as deposits in dissolved form or in patches, for percutaneous application.

Skin applications include ointments, gels, creams, lotions, suspensions or emulsions.

The preferred form of rectal application is by means of suppositories.

In a preferred embodiment, the pharmaceutical compositions are in oral form, either solid or liquid. Suitable dose forms for oral administration may be tablets, capsules, syrups or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or abletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized product propriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

The following examples are merely illustrative of certain embodiments of the invention and cannot be considered as restricting it in any way.

EXAMPLES

In the next preparation examples the synthesis of both intermediate derivatives as well as compounds according to the invention are disclosed.

The following abbreviations are used in the examples:
ACN: acetonitrile
ADDP: 1,1'-(azodicarbonyl)dipiperidine
Boc: tert-butoxycarbonyl
BuLi: butyl lithium
Conc: concentrated
DCM: dichloromethane
DEA: diethylamine
DIAD: diisopropyl azodicarboxylate
DMA: N,N-dimethylacetamide
Eq: equivalent/s
$Et_2O$; diethyl ether
EtOAc; ethyl acetate
EtOH: ethanol
EX: example
h: hour/s
HPLC: high performance liquid chromatography
2-Me-CBS-oxazaborolidine: 5,5-diphenyl-2-methyl-3,4-propano-1,3,2-oxazaborolidine (Corey-Bakshi-Shibata oxazaborolidine catalyst)
MeOH: methanol
MS: mass spectrometry
Min.: minutes
$PPh_3$: triphenylphosphine
Quant: quantitative
Ret.: retention
r.t.: room temperature
Sat: saturated
TEA: triethylamine
TFA: trifluoroacetic acid
THF: tetrahydrofuran
Wt: weight The following methods were used to determine the HPLC-MS spectra:

Method A
Column Xbridge C18 XP 30×4.6 mm, 2.5 um
Temperature: 40° C.
Flow: 2.0 mL/min
Gradient: $NH_4HCO_3$ pH 8: ACN (95:5)—0.5 min—(95:5)—6.5 min—(0:100)—1 min—(0:100)
Sample dissolved approx. 1 mg/mL in $NH_4HCO_3$ pH 8/ACN Method B
Column: Gemini-NX 30×4.6 mm, 3 um
Temperature: 40° C.
Flow: 2.0 mL/min
Gradient: $NH_4HCO_3$ pH 8: ACN (95:5)—0.5 min—(95:5)—6.5 min—(0:100)—1 min—(0:100)
Sample dissolved approx. 1 mg/mL in $NH_4HCO_3$ pH 8/ACN Method C
Column: Kinetex EVO 50×4.6 mm, 2.6 um
Temperature: 40° C.
Flow: 2.0 mL/min
Gradient: $NH_4HCO_3$ pH 8: ACN (95:5)—0.5 min—(95:5)—6.5 min—(0:100)—1 min—(0:100)e dissolved approx. 1 mg/mL $NH_4HCO_3$ pH 8/ACN Method D
Column: Kinetex EVO 50×4.6 mm, 2.6 um
Temperature: 40° C.
Flow: 1.5 mL/min
Gradient: NH$_4$HCO$_3$ pH 8: ACN (95:5)—0.5 min—(95:5)—6.5 min—(0:100)—2 min—(0:100)
Sample dissolved approx. 1 mg/mL in NH$_4$HCO$_3$ pH 8/ACN Synthesis of Intermediates Intermediate 1: 3-(Methylamino)-1-(6-(trifluoromethyl)pyridin-2-yl)propan-1-ol

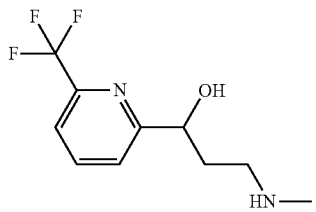

Step 1. tert-Butyl methyl(3-ox(trifluoromethyl)pyridin-2-yl)propyl)carbamate

To a solution of 2-bromo-6-(trifluoromethyl)pyridine (1 g, 4.4 mmol) in dry THF (14.4 mL), cooled at −78° C., BuLi (2.5 M solution in hexanes, 1.7 mL, 4.3 mmol) was added dropwise. After stirring for 1 h at −78° C., a solution of tert-butyl (3-(methoxy(methyl)amino)-3-oxopropyl)(methyl)carbamate (0.727 g, 2.95 mmol) in THF (9.7 mL) was added dropwise. The solution was gradually warmed up to r.t. and stirred overnight. To the crude reaction mixture, NH$_4$Cl sat. solution (25 mL) and EtOAc (25 mL) were added. The phases were separated and the aqueous phase was extracted with EtOAc. The combined organic extracts were dried over MgSO$_4$ and concentrated to dryness. The residue was purified by flash chromatography, silica gel, gradient Cyclohexane/EtOAc 100:0 to Cyclohexane/EtOAc 0:100 to give the title compound (408 mg, 41% yield).

Step 2. tert-Butyl (3-hydrox(trifluoromethyl)pyridin-2-yl)propyl)(methyl)carbamate To a cooled solution of the product obtained in Step 1 (0.4 g, 1.23 mmol) in MeOH (10 mL), NaBH$_4$ (141 mg, 3.68 mmol) was added portionwise and the mixture was stirred at 0° C. for 1 h. NH$_4$Cl sat. solution was then added (25 mL) and MeOH was distilled off. The aqueous phase was extracted with EtOAc, dried over MgSO$_4$ and concentrated to dryness to afford the title compound (332 mg, 78% yield).

Step 3. Title Compound

A solution of the product obtained in Step 2 (332 mg, 0.99 mmol) and TFA (0.76 mL, 9.9 mmol) was stirred at r.t. overnight. Additional TFA (0.38 mL, 4.95 mmol) was added to achieve full conversion. It was then concentrated to dryness and the residue was redissolved in DCM. The organic phase was washed with 1 M NaOH solution, dried over MgSO$_4$ and concentrated under vacuum to yield the title compound (257 mg, quant yield).

This method was used for the preparation of Intermediates 2-7 using suitable starting materials:

| INT | Structure | Chemical name |
|---|---|---|
| 2 | 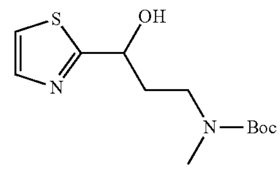 [SMILES: CN(CCC(O)c1nccs1)C(=O)OC(C)(C)C] | tert-butyl (3-hydroxy-3-(thiazol-2-yl)propyl)(methyl)carbamate[1] |
| 3 | 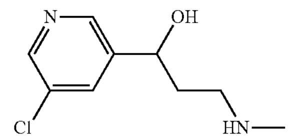 | 1-(5-chloropyridin-3-yl)-3-(methylamino)propan-1-ol |
| 4 | 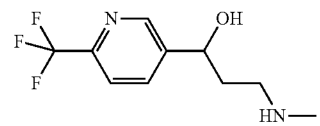 [SMILES: CNCCC(O)c1ccc(C(F)(F)F)nc1] | 3-(methylamino)-1-(6-(trifluoromethyl)pyridin-3-yl)propan-1-ol |
| 5 | 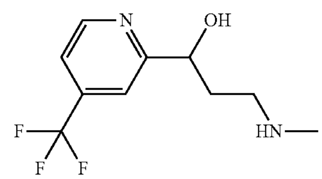 [SMILES: CNCCC(O)c1cc(C(F)(F)F)ccn1] | 3-(methylamino)-1-(4-(trifluoromethyl)pyridin-2-yl)propan-1-ol |
| 6 | 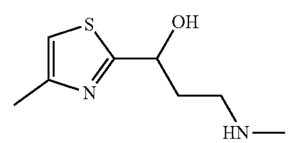 | 3-(methylamino)-1-(4-methylthiazol-2-yl)propan-1-ol |
| 7 | 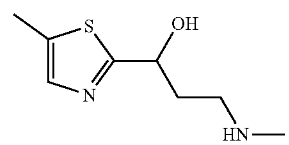 | 3-(methylamino)-1-(5-methylthiazol-2-yl)propan-1-ol |

[1]In this case, Step 3 was not performed, obtaining the Boc-protected intermediate.

Intermediate 8: 1-(3-Fluorothiophen-2-yl)-3-(methylamino)propan-1-ol

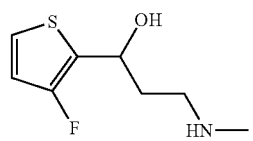

Step 1. 1-(3-Fluorothiophen-2-yl)-3-(methylamino)propan-1-one hydrochloride

In a sealed tube, 1-(3-fluorothiophen-2-yl)ethanone (1.1 g, 7.6 mmol), methylamine hydrochloride (0.567 g, 8.39 mmol), paraformaldehyde (0.321 g, 10.6 mmol) and conc. HCl (0.04 mL, 7.63 mmol) were dissolved in EtOH (3.8 mL). The reaction mixture was heated at 110° C. overnight. The solvent was concentrated, EtOAc (7.6 mL) was added and the suspension was stirred at r.t. for 3 h. The solids were filtered and washed with EtOAc to afford the title compound as an impure orange solid. The crude product was slurried in a mixture of EtOAc (5.6 mL) and EtOH (1.8 mL) and it was heated to reflux for 1 h. The solids were filtered, washed with EtOAc and dried under vacuum to afford the title compound (820 mg, 48% yield).

Step 2. Title Compound

To a cooled solution of the product obtained in Step 1 (0.82 g, 3.67 mmol) in MeOH (50 mL), NaBH$_4$ (0.416 g, 11 mmol) was added portionwise and the mixture was stirred at 0° C. for 1 h. NH$_4$Cl sat. solution was then added (25 mL) and MeOH was distilled off. The aqueous phase was extracted with DCM, dried over MgSO$_4$ and concentrated to dryness to afford the title compound (460 mg, 66% yield).

This method was used for the preparation of Intermediates 9-11 using suitable starting materials:

| INT | Structure | Chemical name |
|---|---|---|
| 9 | 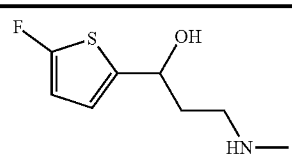 | 1-(5-fluorothiophen-2-yl)-3-(methylamino)propan-1-ol |
| 10 | 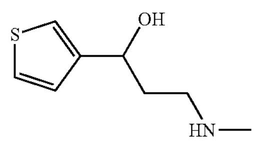 | 3-(methylamino)-1-(thiophen-3-yl)propan-1-ol |
| 11 | 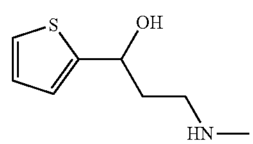 | 3-(methylamino)-1-(thiophen-2-yl)propan-1-ol |

Intermediate 12: (R)-1-(5-Fluorothiophen-2-yl)-3-(methylamino)propan-1-ol

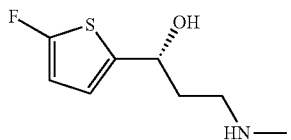

Step 1.
3-Chloro-1-(5-fluorothiophen-2-yl)propan-1-one

To a suspension of AlCl$_3$ (3.13 g, 23.5 mmol) in DCM (24 mL) cooled at 0° C., 3-chloropropanoyl chloride (2 mL, 21.5 mmol) was added dropwise. After stirring for 10 min at 0° C., a solution of 2-fluorothiophene (2 g, 1.6 mmol) in DCM (12 mL) was added. The reaction mixture was then stirred at 0-5° C. for 1 h. Then, crushed ice was added, the phases were separated and the aqueous phase was extracted with DCM. The combined organic phases were dried over Na$_2$SO$_4$ and concentrated to dryness. The crude product was purified by flash chromatography, silica gel, gradient Cyclohexane/EtOAc 100:0 to Cyclohexane/EtOAc 0:100 to give the title compound (2.48 g, 66% yield).

Step 2. (R)-3-Chloro-1-(5-fluorothiophen-2-yl)propan-1-ol

To a solution of (S)-2-Me-CBS-oxazaborolidine (0.719 g, 2.60 mmol) in dry THF (51 mL), borane dimethyl sulfide complex (2.46 mL, 26 mmol) was added dropwise at r.t. After stirring for 10 min, a solution of the product obtained in Step 1 (2.5 g, 12.9 mmol) in dry THF (88 mL) was added during 1 h. The reaction mixture was stirred at r.t. for 1 h. Then, it was concentrated to dryness. The residue was dissolved in Et$_2$O (198 mL) and it was washed with NH$_4$Cl sat. solution (100 mL). The organic phase was dried over MgSO$_4$ and concentrated under vacuum. The crude product was purified by flash chromatography, silica gel, gradient Cyclohexane/EtOAc 100:0 to Cyclohexane/EtOAc 0:100 to give the title compound (1.92 g, 76% yield).

Step 3. Title Compound

In a round-bottom pressure flask, a mixture of the product obtained in Step 2 (1.92 g, 9.86 mmol) and methylamine (57 mL, 458 mmol, 33 wt % in EtOH) was heated at 90° C. overnight. The solvent was concentrated to dryness and the residue was dissolved in DCM (25 mL) that was washed with 1 N NaOH solution (2×15 mL). The organic phase was dried over MgSO4 and concentrated under vacuum to afford the title compound (1.62 g, 86% yield). The crude product (1.12 g) was crystallized in order to enrich the enantiomeric excess by heating at 60° C. in a mixture of methylcyclohexane-toluene (3:1). The solids were filtered and dried under vacuum to render the title compound (763 mg, 68% recovery yield).

Intermediate 13: (S)-1-(5-Fluorothiophen-2-yl)-3-(methylamino)propan-1-ol

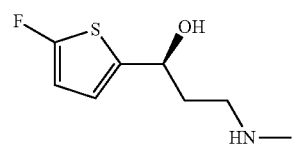

Following the procedure described for the synthesis of intermediate 12 but using (R)-2-Me-CBS-oxazaborolidine in Step 2, the title compound can be obtained.

Intermediate 14: (R)-3-(Methylamino)-1-(thiophen-3-yl)propan-1-ol

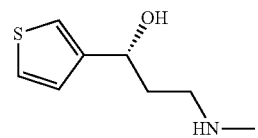

Step 1. (R)-3-Chloro-1-(thiophen-3-yl)propan-1-ol

Starting from 3-chloro-1-(thiophen-3-yl)propan-1-one (prepared according to the procedure described in US2003/

0158185 Example 74 steps a-c) (2 g, 11.45 mmol) and following the experimental procedure described in Step 2 of Intermediate 12, the title compound was obtained (1.92 g, 95% yield).

Step 2. Title Compound

Starting from the product obtained in Step 1 and following the experimental procedure described in Step 3 of Intermediate 12, the title compound was obtained (842 mg, 88% yield).

Intermediate 15: (S)-3-(Methylamino)-1-(thiophen-3-yl)propan-1-ol

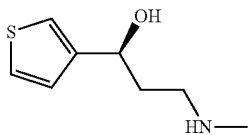

Following the procedure described for the synthesis of intermediate 14 but using (R)-2-Me-CBS-oxazaborolidine in Step 1, the title compound was obtained.

Intermediate 16: tert-Butyl (3-hydroxy-3-(thiophen-2-yl)propyl)(methyl)carbamate

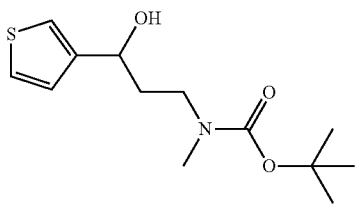 [SMILES: CN(CCC(O)c1ccsc1)C(=O)OC(C)(C)C]

A solution of intermediate 11 (0.39 g, 2.29 mmol) and di-tert-butyl dicarbonate (0.55 g, 2.5 mmol) in a mixture of tert-butanol (2 mL), water (2 mL) and 6 M NaOH solution (0.5 mL) was stirred at r.t. for 30 min. Brine and DCM were then added to the reaction mixture and the layers were separated. The organic phase was dried over $MgSO_4$ and concentrated under vacuum. The residue was purified by flash chromatography, silica gel, gradient DCM to MeOH:DCM (1:4) to give the title compound (447 mg, 72% yield).

Intermediate 17: 5-Fluoro-2,4-dimethylquinoline

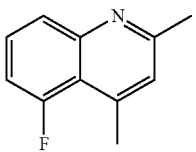

In a round-bottomed flask, a solution of 5-fluoroquinoline (255 g, 1.73 mmol) and (4,4'-di-tert-butyl-2,2'-bipyridine)bis[3,5-difluoro-2-[5-trifluoromethyl-2-pyridinyl-kN]phenyl-kC]iridium(III) hexafluorophosphate (CAS number 870987-63-6, 39 mg, 0.035 mmol) in a 1:1 mixture of ACN and acetic acid (17.2 mL) was degassed by bubbling $N_2$ through the solution.ert-butyl peracetate (50 wt. % in odorless mineral spirits, 1.4 mL, 4.33 mmol) was added. The flask was placed in a Dewar and it was irradiated with blue-LEDs (Kessil H150 lamp) for 24 h, cooling the system with a mini-fan in order to maintain the temperature below 30° C. Additional Ir catalyst (39 mg, 0.035) and tell-butyl peracetate (50 wt. % in odorless mineral spirits, 1.4 mL, 4.33 mmol) were added and the reaction mixture was irradiated for 48 h. The volatiles were removed under vacuum and the residue was purified by flash chromatography, silica gel, gradient Cyclohexane/EtOAc 100:0 to 0:100, to give the title compound (104 mg, 34% yield).

Intermediate 18: (R)-3-(Ethylamino)-1-(thiophen-2-yl)propan-1-ol

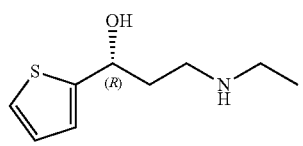

Following the procedure described for the synthesis of intermediate 12 but using thiophene in Step 1 and ethylamine in Step 3, the title compound was obtained.

Intermediate 19: (S)-3-(Ethylamino)-1-(thiophen-2-yl)propan-1-ol

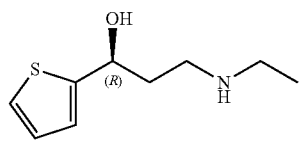

Following the procedure described for the synthesis of intermediate 18 but using (R)-2-Me-CBS-oxazaborolidine in Step 1, the title compound was obtained.

SYNTHESIS OF EXAMPLES

Example 1: N-Methyl-3-(quinolin-8-yloxy)-3-(thiophen-2-yl)propan-1-amine

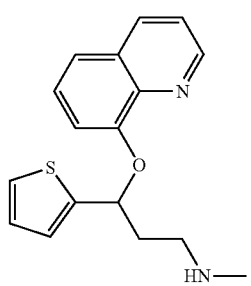 [SMILES: CNCCC(Oc1cccc2cccnc12)c1cccs1]

Step 1.
8-(3-Chloro-1-(thiophen-2-yl)propoxy)quinoline

To a solution of 3-chloro-1-(thiophen-2-yl)propan-1-ol (0.2 g, 1.13 mmol), tributylphosphine (0.34 mL, 1.36 mmol) and quinolin-8-ol (0.164 g, 1.13 mmol) in toluene (6 mL), ADDP (0.343 g, 1.36 mmol) was added and the reaction mixture was heated at 100° C. overnight. It was then allowed to cool, the suspension was filtered and the collected solids were washed with toluene. The filtrate containing the desired product was concentrated under vacuum. The crude product was purified by flash chromatography, silica gel, gradient DCM to MeOH:DCM (1:4) to give the title compound (74 mg, 21% yield).

Step 2. Title Compound

In a sealed tube, a mixture of the product obtained in Step 1 (74 mg, 0.244 mmol), NaI (7.3 mg, 0.049 mmol) and methylamine (33 wt % in EtOH, 0.152 mL, 1.22 mmol) in EtOH (28 mL) was heated at 100° C. overnight. Then, the solvent was concentrated. The crude product was dissolved in DCM (10 mL) and it was washed with 1 N NaOH solution and then brine. The organic phase was dried over $MgSO_4$ and concentrated under vacuum. The crude product was purified by flash chromatography, $C_{18}$, gradient $NH_4HCO_3$ pH 8 to ACN to give the title compound (20 mg, 23% yield).

HPLC retention time (method A): 3.16 min; MS: 299.1 (M+H).

This method was used for the preparation of Examples 2-6 using suitable starting materials:

| EX | Structure | Chemical name | Ret time (min) | MS (M + H) | HPLC Method |
|---|---|---|---|---|---|
| 2 | 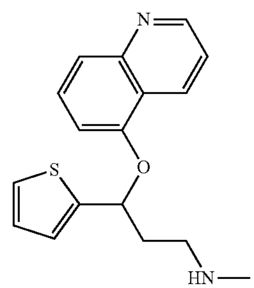 [SMILES: CNCCC(Oc1cccc2ncccc12)c1cccs1] | N-methyl-3-(quinolin-5-yloxy)-3-(thiophen-2-yl)propan-1-amine[1] | 2.74 | 299.1 | A |
| 3 | 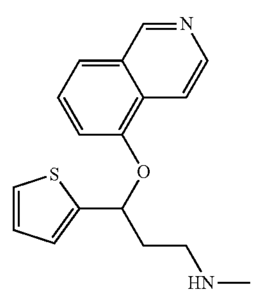 | 3-(isoquinolin-5-yloxy)-N-methyl-3-(thiophen-2-yl)propan-1-amine | 2.90 | 299.1 | A |
| 4 | 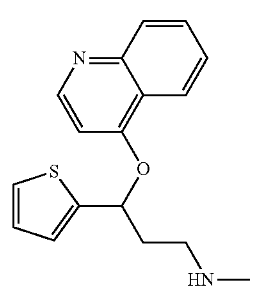 [SMILES: CNCCC(Oc1ccnc2ccccc12)c1cccs1] | N-methyl-3-(quinolin-4-yloxy)-3-(thiophen-2-yl)propan-1-amine[1] | 2.43 | 299.0 | A |

| EX | Structure | Chemical name | Ret time (min) | MS (M + H) | HPLC Method |
|---|---|---|---|---|---|
| 5 | 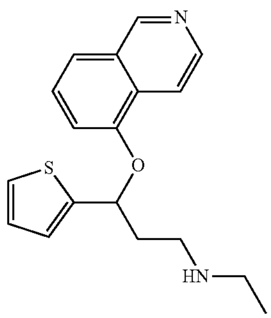 [SMILES: CCNCCC(Oc1cccc2cnccc12)c1cccs1] | N-ethyl-3-(isoquinolin-5-yloxy)-3-(thiophen-2-yl)propan-1-amine | 3.05 | 313.1 | A |
| 6 | 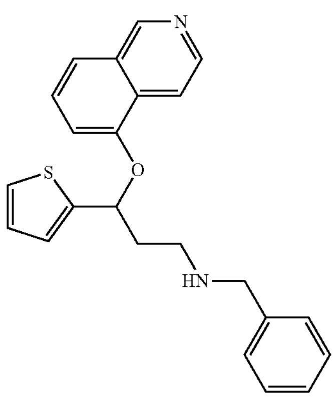 [SMILES: c1ccc(CNCCC(Oc2cccc3cnccc23)c2cccs2)cc1] | N-benzyl-3-(isoquinolin-5-yloxy)-3-(thiophen-2-yl)propan-1-amine | 4.42 | 375.0 | A |

(1)Step 1 was performed using PPh$_3$ and DIAD in THF

Example 7: (R)—N-Methyl-3-(quinolin-6-yloxy)-3-(thiophen-2-yl)propan-1-amine

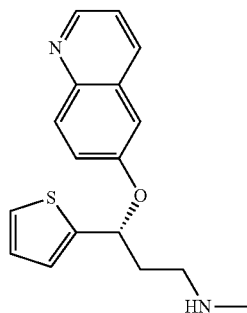 [SMILES: CNCC[C@@H](Oc1ccc2ncccc2c1)c1cccs1]

To a solution of (R)-3-(methylamino)-1-(thiophen-2-yl)propan-1-ol (150 mg, 0.88 mmol) in anhydrous DMA (6 mL) cooled at 0° C. under a N$_2$ atmosphere, NaH (60% dispersion in mineral oil, 70 mg, 1.75 mmol) was added portionwise. After stirring at 0° C. for 30 min, a solution of 6-fluoroquinoline (155 mg, 1.05 mmol) in anhydrous DMA (3 mL) was added and the reaction mixture was stirred at 50° C. for 1.5 h. It was cooled to 0° C. and then water was carefully added. The aqueous phase was extracted with DCM, the combined organic phases were dried over MgSO$_4$ and then evaporated to dryness. The crude product was purified by flash chromatography, silica gel, gradient DCM to MeOH:DCM (1:4) to give the title compound (154 mg, 59% yield).

HPLC retention time (method B): 2.96 min; MS: 299.1 (M+H).

This method was used for the preparation of Examples 8-69 using suitable starting materials:

| EX | Structure | Chemical name | Ret time (min) | MS (M + H) | HPLC Method |
|---|---|---|---|---|---|
| 8 | 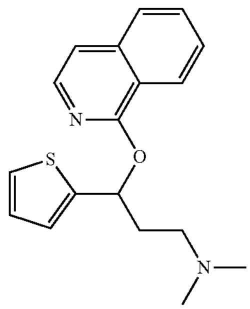 [SMILES: CN(C)CCC(Oc1nccc2ccccc12)c1cccs1] | 3-(isoquinolin-1-yloxy)-N,N-dimethyl-3-(thiophen-2-yl)propan-1-amine | 4.40 | Only fragmentation m/z observed | A |
| 9 | 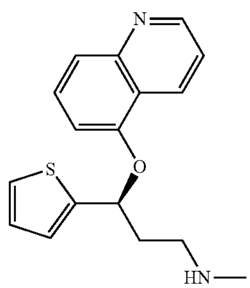 [SMILES: CNCC[C@H](Oc1cccc2ncccc12)c1cccs1] | (S)-N-methyl-3-(quinolin-5-yloxy)-3-(thiophen-2-yl)propan-1-amine | 2.94 | 299.0 | B |
| 10 | 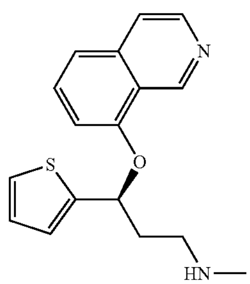 [SMILES: CNCC[C@H](Oc1cccc2ccncc12)c1cccs1] | (S)-3-(isoquinolin-8-yloxy)-N-methyl-3-(thiophen-2-yl)propan-1-amine | 2.99 | 299.0 | A |
| 11 | 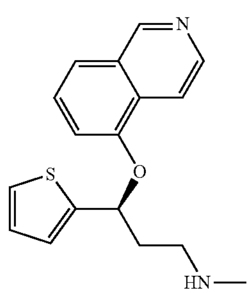 [SMILES: CNCC[C@H](Oc1cccc2cnccc12)c1cccs1] | (S)-3-(isoquinolin-5-yloxy)-N-methyl-3-(thiophen-2-yl)propan-1-amine | 2.87 | 299.1 | A |
| 12 | 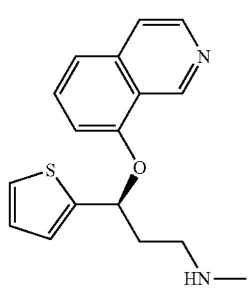 [SMILES: CNCC[C@H](Oc1cccc2ccncc12)c1cccs1] | 3-(isoquinolin-8-yloxy)-N-methyl-3-(thiophen-2-yl)propan-1-amine | 3.03 | 299.1 | A |

-continued

| EX | Structure | Chemical name | Ret time (min) | MS (M + H) | HPLC Method |
|---|---|---|---|---|---|
| 13 | 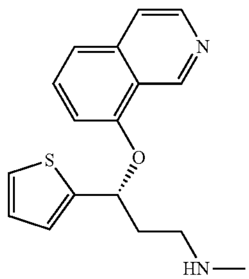 [SMILES: CNCC[C@@H](Oc1cccc2ccncc12)c1cccs1] | (R)-3-(isoquinolin-8-yloxy)-N-methyl-3-(thiophen-2-yl)propan-1-amine | 3.12 | 299.1 | A |
| 14 | 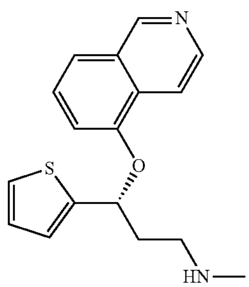 [SMILES: CNCC[C@@H](Oc1cccc2cnccc12)c1cccs1] | (R)-3-(isoquinolin-5-yloxy)-N-methyl-3-(thiophen-2-yl)propan-1-amine | 3.12 | 299.1 | B |
| 15 | 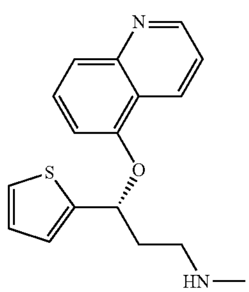 [SMILES: CNCC[C@@H](Oc1cccc2ncccc12)c1cccs1] | (R)-N-methyl-3-(quinolin-5-yloxy)-3-(thiophen-2-yl)propan-1-amine | 2.92 | 299.1 | A |
| 16 | 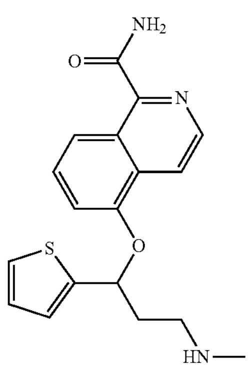 [SMILES: CNCCC(Oc1cccc2c(C(N)=O)nccc12)c1cccs1] | 5-(3-(methylamino)-1-(thiophen-2-yl)propoxy)isoquinoline-1-carboxamide[1] | 2.66 | 342.1 | A |
| 17 | 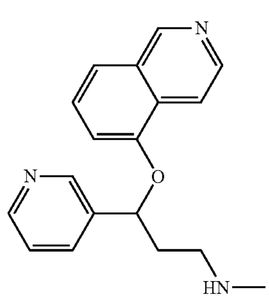 [SMILES: CNCCC(Oc1cccc2cnccc12)c1cccnc1] | 3-(isoquinolin-5-yloxy)-N-methyl-3-(pyridin-3-yl)propan-1-amine | 2.31 | 294.1 | A |

-continued

| EX | Structure | Chemical name | Ret time (min) | MS (M + H) | HPLC Method |
|---|---|---|---|---|---|
| 18 | 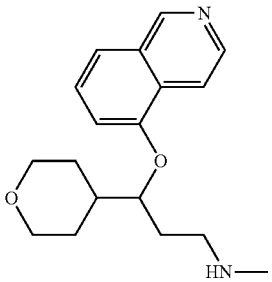 [SMILES: CNCCC(Oc1cccc2cnccc12)C1CCOCC1] | 3-(isoquinolin-5-yloxy)-N-methyl-3-(tetrahydro-2H-pyran-4-yl)propan-1-amine | 2.45 | 301.1 | A |
| 19 | 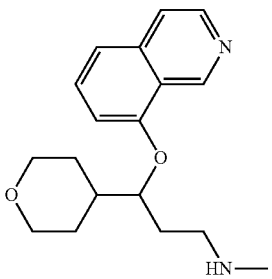 [SMILES: CNCCC(Oc1cccc2ccncc12)C1CCOCC1] | 3-(isoquinolin-8-yloxy)-N-methyl-3-(tetrahydro-2H-pyran-4-yl)propan-1-amine | 2.60 | 301.1 | A |
| 20 | 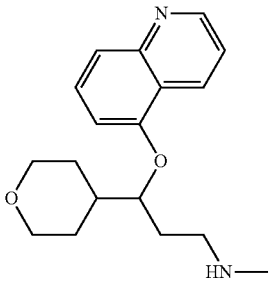 [SMILES: CNCCC(Oc1cccc2ncccc12)C1CCOCC1] | N-methyl-3-(quinolin-5-yloxy)-3-(tetrahydro-2H-pyran-4-yl)propan-1-amine | 2.39 | 301.1 | A |
| 21 | 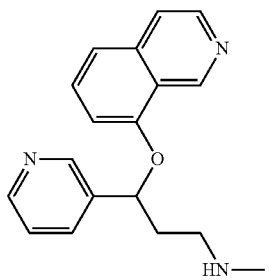 [SMILES: CNCCC(Oc1cccc2ccncc12)c1cccnc1] | 3-(isoquinolin-8-yloxy)-N-methyl-3-(pyridin-3-yl)propan-1-amine | 2.46 | 294.1 | A |
| 22 | 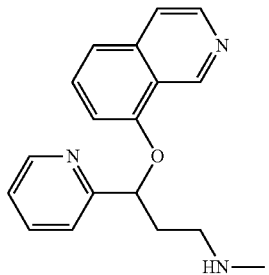 [SMILES: CNCCC(Oc1cccc2ccncc12)c1ccccn1] | 3-(isoquinolin-8-yloxy)-N-methyl-3-(pyridin-2-yl)propan-1-amine | 2.58 | 294.1 | A |

-continued

| EX | Structure | Chemical name | Ret time (min) | MS (M + H) | HPLC Method |
|---|---|---|---|---|---|
| 23 | 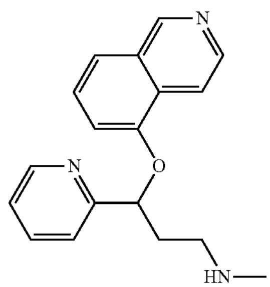 [SMILES: CNCCC(Oc1cccc2cnccc12)c1ccccn1] | 3-(isoquinolin-5-yloxy)-N-methyl-3-(pyridin-2-yl)propan-1-amine | 2.50 | 294.1 | A |
| 24 | 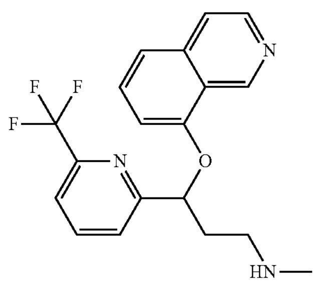 [SMILES: CNCCC(Oc1cccc2ccncc12)c1cccc(C(F)(F)F)n1] | 3-(isoquinolin-8-yloxy)-N-methyl-3-(6-(trifluoromethyl)pyridin-2-yl)propan-1-amine | 3.39 | 362.1 | A |
| 25 | 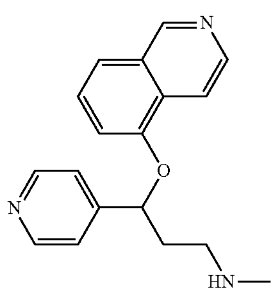 [SMILES: CNCCC(Oc1cccc2cnccc12)c1ccncc1] | 3-(isoquinolin-5-yloxy)-N-methyl-3-(pyridin-4-yl)propan-1-amine | 2.21 | 294.1 | A |
| 26 | 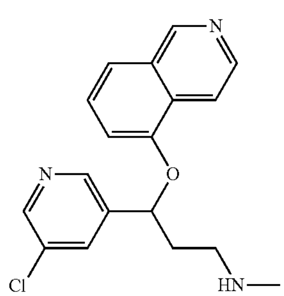 [SMILES: CNCCC(Oc1cccc2cnccc12)c1cncc(Cl)c1] | 3-(5-chloropyridin-3-yl)-3-(isoquinolin-5-yloxy)-N-methylpropan-1-amine | 2.77 | 328.1 | A |
| 27 | 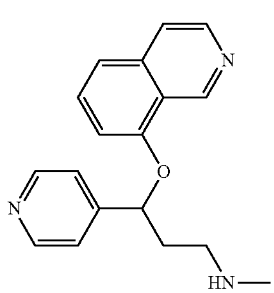 [SMILES: CNCCC(Oc1cccc2ccncc12)c1ccncc1] | 3-(isoquinolin-8-yloxy)-N-methyl-3-(pyridin-4-yl)propan-1-amine | 2.40 | 294.1 | A |

-continued

| EX | Structure | Chemical name | Ret time (min) | MS (M + H) | HPLC Method |
|---|---|---|---|---|---|
| 28 | 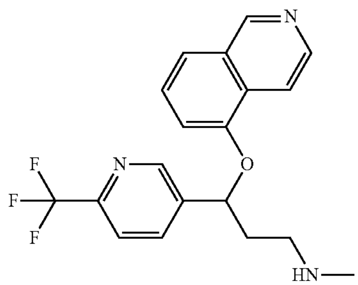 [SMILES: CNCCC(Oc1cccc2cnccc12)c1ccc(C(F)(F)F)nc1] | 3-(isoquinolin-5-yloxy)-N-methyl-3-(6-(trifluoromethyl)pyridin-3-yl)propan-1-amine | 3.16 | 362.1 | A |
| 29 | 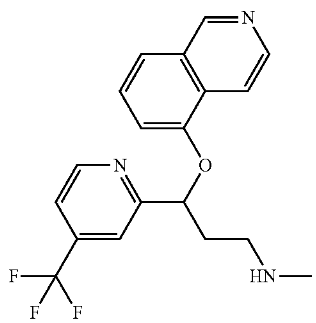 [SMILES: CNCCC(Oc1cccc2cnccc12)c1cc(C(F)(F)F)ccn1] | 3-(isoquinolin-5-yloxy)-N-methyl-3-(4-(trifluoromethyl)pyridin-2-yl)propan-1-amine | 3.08 | 362.1 | A |
| 30 | 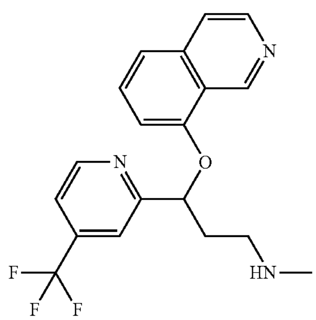 [SMILES: CNCCC(Oc1cccc2ccncc12)c1cc(C(F)(F)F)ccn1] | 3-(isoquinolin-8-yloxy)-N-methyl-3-(4-(trifluoromethyl)pyridin-2-yl)propan-1-amine | 3.24 | 362.1 | A |
| 31 | 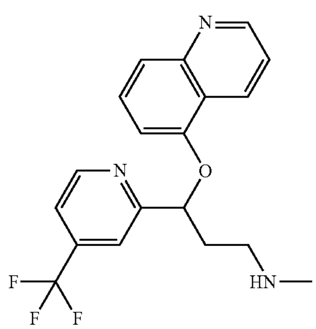 [SMILES: CNCCC(Oc1cccc2ncccc12)c1cc(C(F)(F)F)ccn1] | N-methyl-3-(quinolin-5-yloxy)-3-(4-(trifluoromethyl)pyridin-2-yl)propan-1-amine | 3.07 | 362.1 | A |
| 32 | 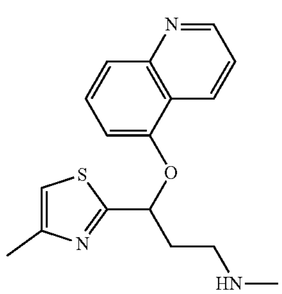 | N-methyl-3-(4-methylthiazol-2-yl)-3-(quinolin-5-yloxy)propan-1-amine | 2.66 | 314.1 | A |

| EX | Structure | Chemical name | Ret time (min) | MS (M + H) | HPLC Method |
|---|---|---|---|---|---|
| 33 | 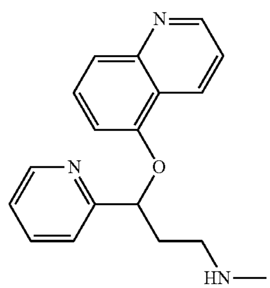 [SMILES: CNCCC(Oc1cccc2ncccc12)c1ccccn1] | N-methyl-3-(pyridin-2-yl)-3-(quinolin-5-yloxy)propan-1-amine | 2.38 | 294.1 | A |
| 34 | 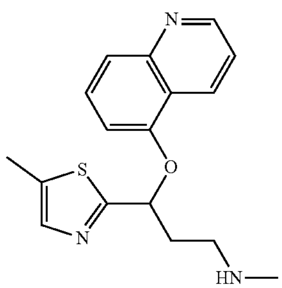 | N-methyl-3-(5-methylthiazol-2-yl)-3-(quinolin-5-yloxy)propan-1-amine | 2.65 | 314.1 | A |
| 35 | 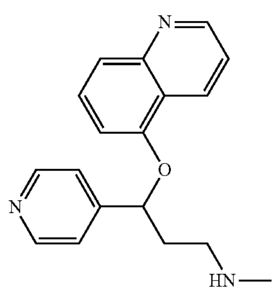 [SMILES: CNCCC(Oc1cccc2ncccc12)c1ccncc1] | N-methyl-3-(pyridin-4-yl)-3-(quinolin-5-yloxy)propan-1-amine | 2.08 | 294.1 | A |
| 36 | 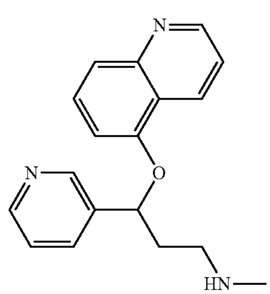 [SMILES: CNCCC(Oc1cccc2ncccc12)c1cccnc1] | N-methyl-3-(pyridin-3-yl)-3-(quinolin-5-yloxy)propan-1-amine | 2.17 | 294.1 | A |
| 37 | 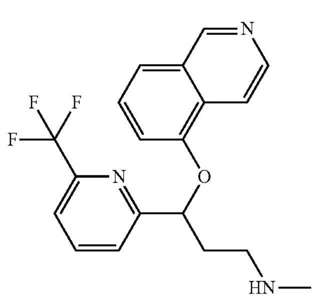 [SMILES: CNCCC(Oc1cccc2cnccc12)c1cccc(C(F)(F)F)n1] | 3-(isoquinolin-5-yloxy)-N-methyl-3-(6-(trifluoromethyl)pyridin-2-yl)propan-1-amine | 3.18 | 362.1 | A |

-continued

| EX | Structure | Chemical name | Ret time (min) | MS (M + H) | HPLC Method |
|---|---|---|---|---|---|
| 38 | 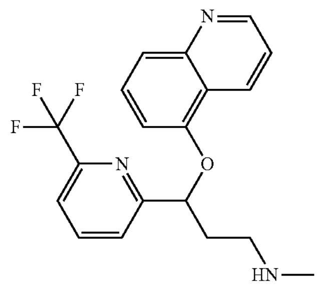 [SMILES: CNCCC(Oc1cccc2ncccc12)c1cccc(C(F)(F)F)n1] | N-methyl-3-(quinolin-5-yloxy)-3-(6-(trifluoromethyl)pyridin-2-yl)propan-1-amine | 3.05 | 362.1 | A |
| 39 | 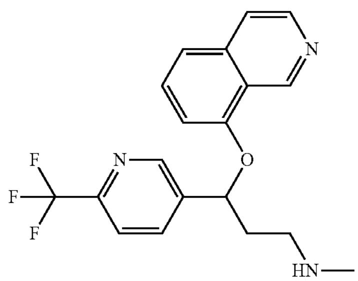 [SMILES: CNCCC(Oc1cccc2ccncc12)c1ccc(C(F)(F)F)nc1] | 3-(isoquinolin-8-yloxy)-N-methyl-3-(6-(trifluoromethyl)pyridin-3-yl)propan-1-amine | 3.15 | 362.1 | A |
| 40 | 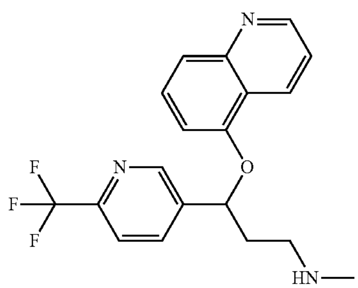 [SMILES: CNCCC(Oc1cccc2ncccc12)c1ccc(C(F)(F)F)nc1] | N-methyl-3-(quinolin-5-yloxy)-3-(6-(trifluoromethyl)pyridin-3-yl)propan-1-amine | 2.97 | 362.1 | A |
| 41 | 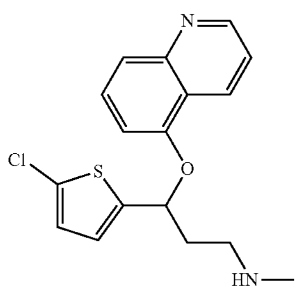 [SMILES: CNCCC(Oc1cccc2ncccc12)c1ccc(Cl)s1] | 3-(5-chlorothiophen-2-yl)-N-methyl-3-(quinolin-5-yloxy)propan-1-amine | 3.30 | 333.0 | A |
| 42 | 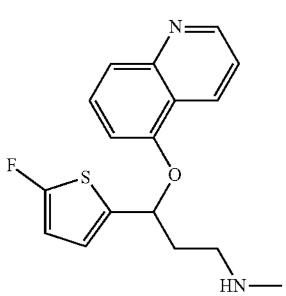 [SMILES: CNCCC(Oc1cccc2ncccc12)c1ccc(F)s1] | 3-(5-fluorothiophen-2-yl)-N-methyl-3-(quinolin-5-yloxy)propan-1-amine | 3.02 | 317.0 | A |

-continued
| EX | Structure | Chemical name | Ret time (min) | MS (M + H) | HPLC Method |
|---|---|---|---|---|---|
| 43 | 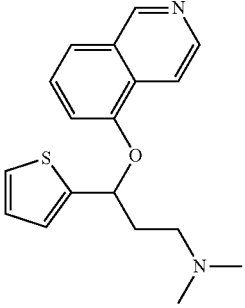 [SMILES: CN(C)CCC(Oc1cccc2cnccc12)c1cccs1] | 3-(isoquinolin-5-yloxy)-N,N-dimethyl-3-(thiophen-2-yl)propan-1-amine | 3.75 | 313.1 | B |
| 44 | 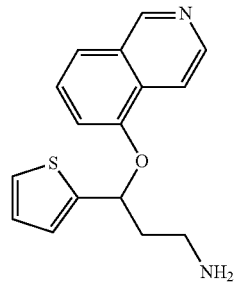 [SMILES: NCCC(Oc1cccc2cnccc12)c1cccs1] | 3-(isoquinolin-5-yloxy)-3-(thiophen-2-yl)propan-1-amine | 2.94 | 285.0 | B |
| 45 | 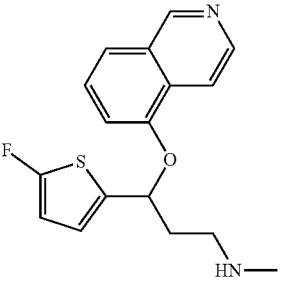 [SMILES: CNCCC(Oc1cccc2cnccc12)c1ccc(F)s1] | 3-(5-fluorothiophen-2-yl)-3-(isoquinolin-5-yloxy)-N-methylpropan-1-amine | 3.28 | 317.0 | B |
| 46 | 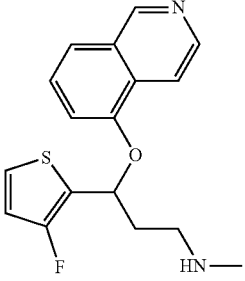 [SMILES: CNCCC(Oc1cccc2cnccc12)c1sccc1F] | 3-(3-fluorothiophen-2-yl)-3-(isoquinolin-5-yloxy)-N-methylpropan-1-amine | 3.09 | 317.0 | B |
| 47 | 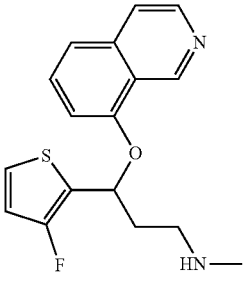 [SMILES: CNCCC(Oc1cccc2ccncc12)c1sccc1F] | 3-(3-fluorothiophen-2-yl)-3-(isoquinolin-8-yloxy)-N-methylpropan-1-amine | 3.28 | 317.1 | B |

-continued

| EX | Structure | Chemical name | Ret time (min) | MS (M + H) | HPLC Method |
|---|---|---|---|---|---|
| 48 | 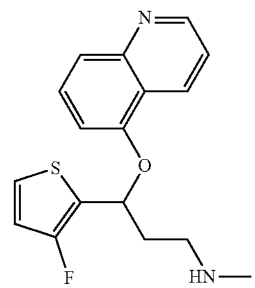 [SMILES: CNCCC(Oc1cccc2ncccc12)c1sccc1F] | 3-(3-fluorothiophen-2-yl)-N-methyl-3-(quinolin-5-yloxy)propan-1-amine | 3.00 | 317.1 | B |
| 49 | 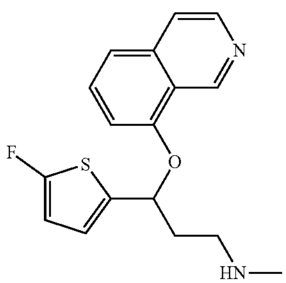 [SMILES: CNCCC(Oc1cccc2ccncc12)c1ccc(F)s1] | 3-(5-fluorothiophen-2-yl)-3-(isoquinolin-8-yloxy)-N-methylpropan-1-amine | 3.38 | 317.0 | B |
| 50 | 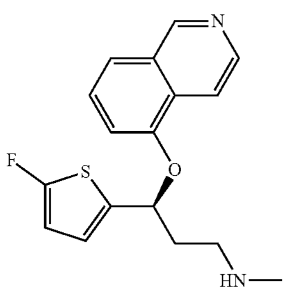 [SMILES: CNCC[C@H](Oc1cccc2cnccc12)c1ccc(F)s1] | (S)-3-(5-fluorothiophen-2-yl)-3-(isoquinolin-5-yloxy)-N-methylpropan-1-amine | 3.22 | 317.0 | B |
| 51 | 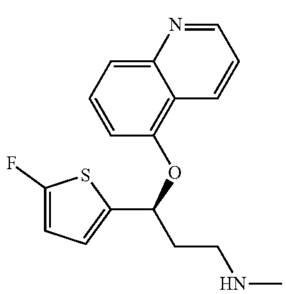 [SMILES: CNCC[C@H](Oc1cccc2ncccc12)c1ccc(F)s1] | (S)-3-(5-fluorothiophen-2-yl)-N-methyl-3-(quinolin-5-yloxy)propan-1-amine | 3.18 | 317.0 | B |
| 52 | 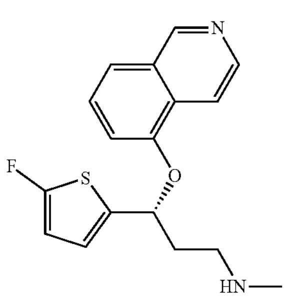 [SMILES: CNCC[C@@H](Oc1cccc2cnccc12)c1ccc(F)s1] | (R)-3-(5-fluorothiophen-2-yl)-3-(isoquinolin-5-yloxy)-N-methylpropan-1-amine | 3.47 | 317.1 | C |

| EX | Structure | Chemical name | Ret time (min) | MS (M + H) | HPLC Method |
|---|---|---|---|---|---|
| 53 | 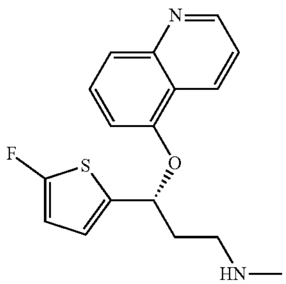 [SMILES: CNCC[C@@H](Oc1cccc2ncccc12)c1ccc(F)s1] | (R)-3-(5-fluorothiophen-2-yl)-N-methyl-3-(quinolin-5-yloxy)propan-1-amine | 3.08 | 317.0 | B |
| 54 | 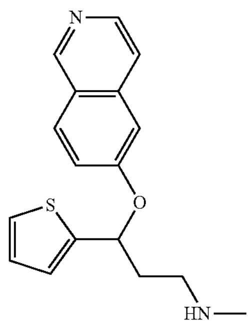 [SMILES: CNCCC(Oc1ccc2cnccc2c1)c1cccs1] | 3-(isoquinolin-6-yloxy)-N-methyl-3-(thiophen-2-yl)propan-1-amine | 2.95 | 299.1 | B |
| 55 | 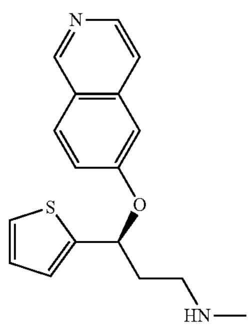 [SMILES: CNCC[C@H](Oc1ccc2cnccc2c1)c1cccs1] | (S)-3-(isoquinolin-6-yloxy)-N-methyl-3-(thiophen-2-yl)propan-1-amine | 2.96 | 299.0 | B |
| 56 | 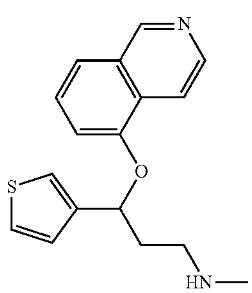 [SMILES: CNCCC(Oc1cccc2cnccc12)c1ccsc1] | 3-(isoquinolin-5-yloxy)-N-methyl-3-(thiophen-3-yl)propan-1-amine | 3.48 | 299.0 | D |
| 57 | 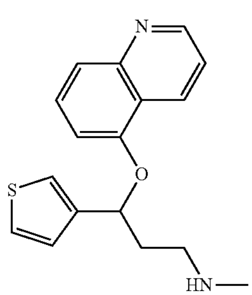 [SMILES: CNCCC(Oc1cccc2ncccc12)c1ccsc1] | N-methyl-3-(quinolin-5-yloxy)-3-(thiophen-3-yl)propan-1-amine | 3.40 | 299.0 | D |

| EX | Structure | Chemical name | Ret time (min) | MS (M + H) | HPLC Method |
|---|---|---|---|---|---|
| 58 | 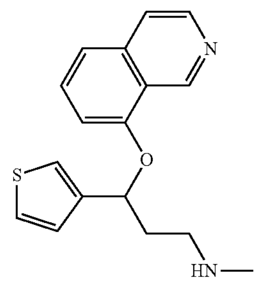 [SMILES: CNCCC(Oc1cccc2ccncc12)c1ccsc1] | 3-(isoquinolin-8-yloxy)-N-methyl-3-(thiophen-3-yl)propan-1-amine | 3.55 | 299.0 | D |
| 59 | 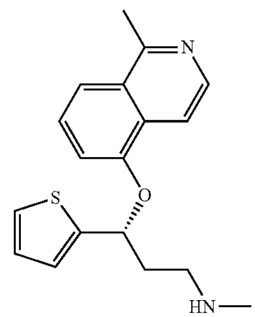 [SMILES: CNCC[C@@H](Oc1cccc2c(C)nccc12)c1cccs1] | (R)-N-methyl-3-((1-methylisoquinolin-5-yl)oxy)-3-(thiophen-2-yl)propan-1-amine | 3.75 | 313.1 | D |
| 60 | 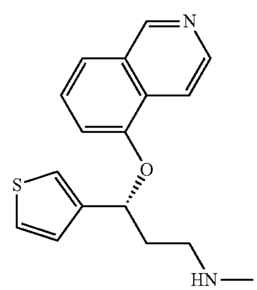 [SMILES: CNCC[C@@H](Oc1cccc2cnccc12)c1ccsc1] | (R)-3-(isoquinolin-5-yloxy)-N-methyl-3-(thiophen-3-yl)propan-1-amine | 3.55 | 299.1 | D |
| 61 | 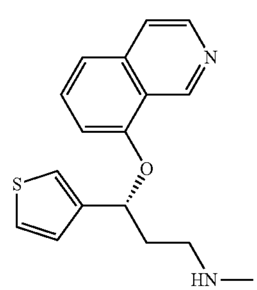 [SMILES: CNCC[C@@H](Oc1cccc2ccncc12)c1ccsc1] | (R)-3-(isoquinolin-8-yloxy)-N-methyl-3-(thiophen-3-yl)propan-1-amine | 3.79 | 299.1 | D |
| 62 | 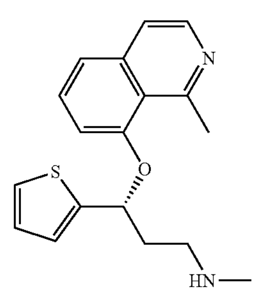 [SMILES: CNCC[C@@H](Oc1cccc2ccnc(C)c12)c1cccs1] | (R)-N-methyl-3-((1-methylisoquinolin-8-yl)oxy)-3-(thiophen-2-yl)propan-1-amine | 3.86 | 313.1 | D |

| EX | Structure | Chemical name | Ret time (min) | MS (M + H) | HPLC Method |
|---|---|---|---|---|---|
| 63 | 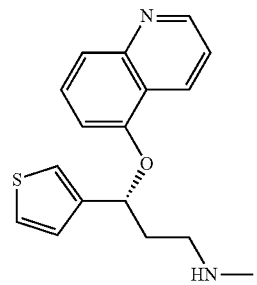 [SMILES: CNCC[C@@H](Oc1cccc2ncccc12)c1ccsc1] | (R)-N-methyl-3-(quinolin-5-yloxy)-3-(thiophen-3-yl)propan-1-amine | 3.47 | 299.1 | D |
| 64 | 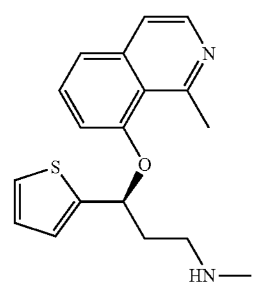 [SMILES: CNCC[C@H](Oc1cccc2ccnc(C)c12)c1cccs1] | (S)-N-methyl-3-((1-methylisoquinolin-8-yl)oxy)-3-(thiophen-2-yl)propan-1-amine | 3.85 | 313.1 | D |
| 65 | 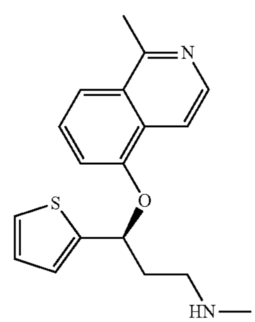 [SMILES: CNCC[C@H](Oc1cccc2c(C)nccc12)c1cccs1] | (S)-N-methyl-3-((1-methylisoquinolin-5-yl)oxy)-3-(thiophen-2-yl)propan-1-amine | 3.93 | 313.1 | D |
| 66 | 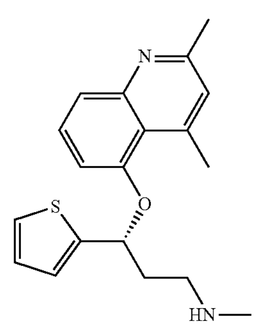 [SMILES: CNCC[C@@H](Oc1cccc2nc(C)cc(C)c12)c1cccs1] | (R)-3-((2,4-dimethylquinolin-5-yl)oxy)-N-methyl-3-(thiophen-2-yl)propan-1-amine | 4.10 | 327.1 | D |
| 67 | 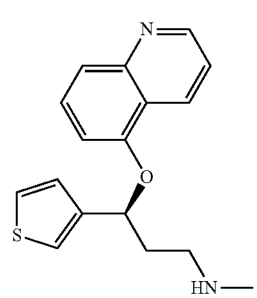 [SMILES: CNCC[C@H](Oc1cccc2ncccc12)c1ccsc1] | (S)-N-methyl-3-(quinolin-5-yloxy)-3-(thiophen-3-yl)propan-1-amine | 3.61 | 299.1 | D |

-continued

| EX | Structure | Chemical name | Ret time (min) | MS (M + H) | HPLC Method |
|----|-----------|---------------|----------------|------------|-------------|
| 68 | 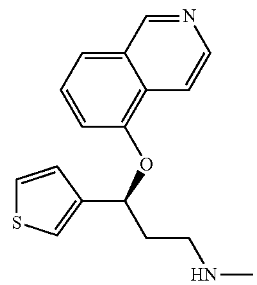 [SMILES: CNCC[C@H](Oc1cccc2cnccc12)c1ccsc1] | (S)-3-(isoquinolin-5-yloxy)-N-methyl-3-(thiophen-3-yl)propan-1-amine | 3.65 | 299.1 | D |
| 69 | 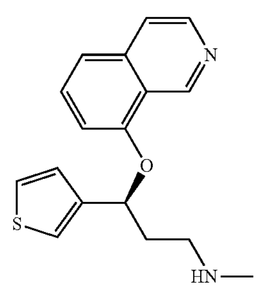 [SMILES: CNCC[C@H](Oc1cccc2ccncc12)c1ccsc1] | (S)-3-(isoquinolin-8-yloxy)-N-methyl-3-(thiophen-3-yl)propan-1-amine | 3.81 | 299.1 | D |

(1)Example 16 was obtained as a hydrolysis by-product while performing the condensation reaction of Intermediate 11 and 5-fluoroisoquinoline-1-carbonitrile

Example 70: 3-(Isoquinolin-8-yloxy)-N-methyl-3-(thiazol-2-yl)propan-1-amine

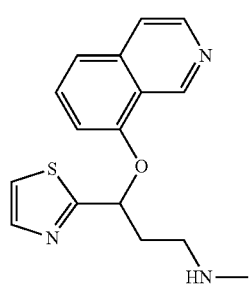 [SMILES: CNCCC(Oc1cccc2ccncc12)c1nccs1]

Step 1. tert-Butyl (3-(isoquinolin-8-yloxy)-3-(thiazol-2-yl)propyl)(methyl)carbamate Following the same procedure described for the preparation of Example 1 Step 1, but starting from Intermediate 2 (100 mg, 0.37 mmol) and isoquinolin-8-ol, the title compound was obtained (67 mg, 45% yield).

Step 2. Title Compound

To a solute of the product obtained in Step 1 (65 mg, 0.16 mmol) in ACN (5 mL), iodotrimethylsilane (46 µL, 0.33 mmol) was added dropwise and the mixture was stirred at r.t. for 30 min. NaHCO$_3$ sat. solution and DCM were added to the reaction mixture and it was stirred for 10 minutes. Layers were separated and the organic phase was washed with 1 N NaOH, dried over MgSO$_4$ and concentrated to dryness. The crude product was purified by flash chromatography, silica gel, gradient DCM to MeOH:DCM (1:4) to give the title compound (16 mg, 33% yield).

HPLC retention time (method A): 2.64 min; MS: 300.1 (M+H).

This method was used for the preparation of Examples 71-74 using suitable starting materials:

| EX | Structure | Chemical name | Ret (min) time | MS (M + H) | HPLC Method |
|----|-----------|---------------|----------------|------------|-------------|
| 71 | 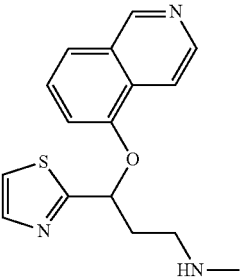 [SMILES: CNCCC(Oc1cccc2cnccc12)c1nccs1] | 3-(isoquinolin-5-yloxy)-N-methyl-3-(thiazol-2-yl)propan-1-amine | 2.52 | 300.1 | A |
| 72 | 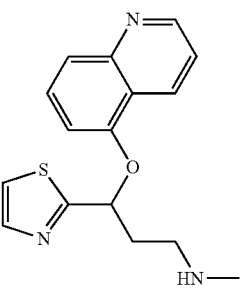 [SMILES: CNCCC(Oc1cccc2ncccc12)c1nccs1] | N-methyl-3-(quinolin-5-yloxy)-3-(thiazol-2-yl)propan-1-amine | 2.48 | 300.1 | A |
| 73 | 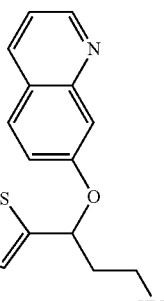 | N-methyl-3-(quinolin-7-yloxy)-3-(thiophen-2-yl)propan-1-amine | 3.14 | 299.0 | B |
| 74 | 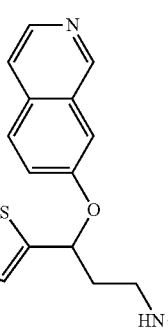 | 3-(isoquinolin-7-yloxy)-N-methyl-3-(thiophen-2-yl)propan-1-amine | 3.06 | 299.0 | B |

Example 75: 5-(3-(Methylamino)-1-(thiophen-2-yl)propoxy)isoquinoline-1-carbonitrile

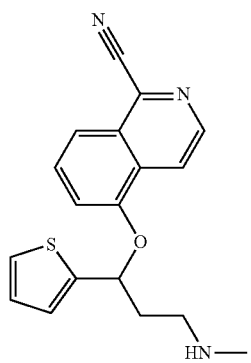 [SMILES: CNCCC(Oc1cccc2c(C#N)nccc12)c1cccs1]

Step 1. 5-(3-(Methylamino)-1-(thiophen-2-yl)propoxy)isoquinoline 2-oxide

Following the experimental procedure described for the preparation of Example 7, using Intermediate 11 and 5-fluoroisoquinoline 2-oxide (prepared following the procedure described in Journal of the Chemical Society 1964, 4561) as starting materials, the title compound was obtained.

Step 2. Title Compound

To a solution of the product obtained in Step 1 (55 mg, 0.175 mmol) and TEA (49 µL, 0.350 mmol) in ACN (0.2 mL), trimethylsilyl cyanide (70 µL, 0.525 mmol) was added under a $N_2$ atmosphere. The reaction mixture was heated at 75° C. for 4 h and it was then diluted with EtOAc. The organic phase was washed with $NaHCO_3$ sat. solution and brine, it was dried over $MgSO_4$ and concentrated. The crude product was purified by flash chromatography, $C_{18}$, gradient $NH_4HCO_3$ pH 8 to ACN to give the title compound (4.5 mg, 7% yield).

HPLC retention time (method A): 3.88 min; MS: 324.1 (M+H).

Examples 76 and 77: (S)—N-Methyl-3-(quinolin-5-yloxy)-3-(thiazol-2-yl)propan-1-amine and (R)—N-methyl-3-(quinolin-5-yloxy)-3-(thiazol-2-yl)propan-1-amine

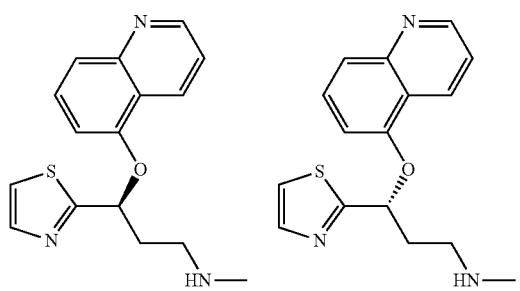 [SMILES: CNCC[C@H](Oc1cccc2ncccc12)c1nccs1 ; CNCC[C@@H](Oc1cccc2ncccc12)c1nccs1]

Starting from Example 72 a chiral preparative HPLC separation (column: Chiralcel OJ; temperature: ambient; flow: 15 mL/min; eluent: n-Heptane/(EtOH+0.33% DEA) 85/15 v/v) was carried out to give the title compounds.

Examples 78 and 79: (S)-3-(5-Chlorothiophen-2-yl)-N-methyl-3-(quinolin-5-yloxy)propan-1-amine and (R)-3-(5-chlorothiophen-2-yl)-N-methyl-3-(quinolin-5-yloxy)propan-1-amine

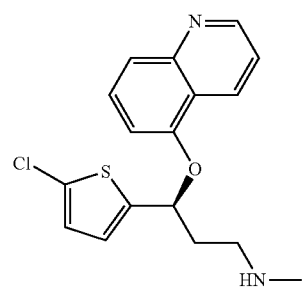

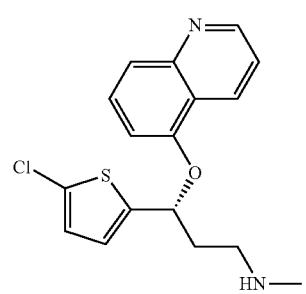

Starting from Example 41 a chiral preparative HPLC separation (column: Chiralpak IC; temperature: ambient; flow: 10 mL/min; eluent: n-Heptane/(IPA+0.2% DEA) 85/15 v/v) was carried out to give the title compounds.

Examples 80 and 81: (S)-3-(5-Fluorothiophen-2-yl)-3-(isoquinolin-8-yloxy)-N-methylpropan-1-amine and (R)-3-(5-fluorothiophen-2-yl)-3-(isoquinolin-8-yloxy)-N-methylpropan-1-amine

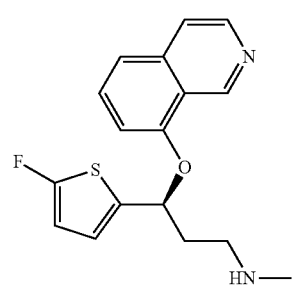

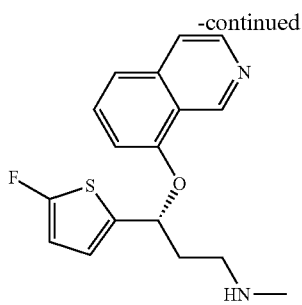

Starting from Example 49, a chiral preparative HPLC separation (column: Chiralpak IB; temperature: ambient; flow: 10 mL/min; eluent: n-Heptane/(EtOH+0.33% DEA) 70/30 v/v) was carried out to give the title compounds.

Examples 82 and 83: (S)-3-(3-Fluorothiophen-2-yl)-3-(isoquinolin-5-yloxy)-N-methylpropan-1-amine and (R)-3-(3-fluorothiophen-2-yl)-3-(isoquinolin-5-yloxy)-N-methylpropan-1-amine Starting from Example 46, a chiral preparative HPLC separation (column: Chiralpak AS-H; temperature: ambient; flow: 0.8 mL/min; eluent: n-Heptane/(EtOH+0.33% DEA) 95/5 v/v) was carried out to give the title compounds.

Examples 84 and 85: (S)-3-(3-Fluorothiophen-2-yl)-N-methyl-3-(quinolin-5-yloxy)propan-1-amine and (R)-3-(3-fluorothiophen-2-yl)-N-methyl-3-(quinolin-5-yloxy)propan-1-amine

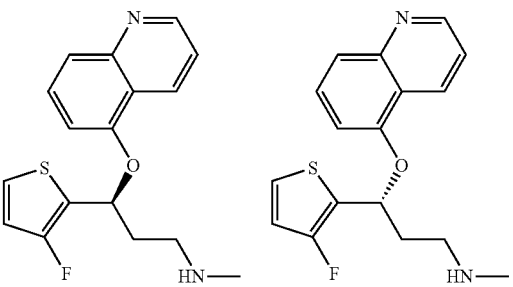 [SMILES: CNCC[C@H](Oc1cccc2ncccc12)c1sccc1F ; CNCC[C@@H](Oc1cccc2ncccc12)c1sccc1F]

Starting from Example 48, a chiral preparative HPLC separation (column: Chiralpak IC; temperature: ambient; flow: 0.8 mL/min; eluent: n-Heptane/(EtOH+0.33% DEA) 90/10 v/v) was carried out to give the title compounds.

Examples 86 and 87: (S)-3-(3-Fluorothiophen-2-yl)-3-(isoquinolin-8-yloxy)-N-methylpropan-1-amine and (R)-3-(3-fluorothiophen-2-yl)-3-(isoquinolin-8-yloxy)-N-methylpropan-1-amine Starting from Example 47, a chiral preparative HPLC separation (column: Chiralpak AS-H; temperature: ambient; flow: 0.8 mL/min; eluent: n-Heptane/(EtOH+0.33% DEA) 95/5 v/v) was carried out to give the title compounds.

Following the method described for the preparation of Example 7 but using suitable starting materials, Examples 88-95 were obtained:

| EX | Structure | Chemical name | Ret time (min) | MS (M + H) | HPLC Method |
|---|---|---|---|---|---|
| 88 | 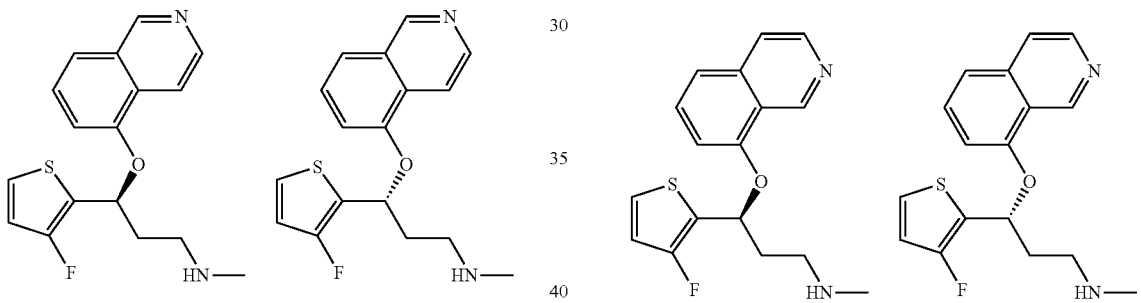 | (R)-N-ethyl-3-(isoquinolin-5-yloxy)-3-(thiophen-2-yl)propan-1-amine | 3.89 | 313.1 | D |

-continued

| EX | Structure | Chemical name | Ret time (min) | MS (M + H) | HPLC Method |
|---|---|---|---|---|---|
| 89 | 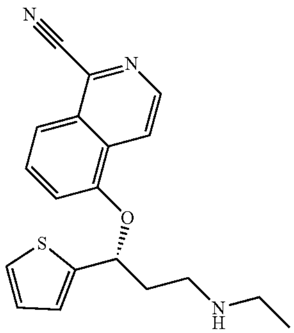 [SMILES: CCNCC[C@@H](Oc1cccc2c(C#N)nccc12)c1cccs1] | (R)-5-(3-(ethylamino)-1-(thiophen-2-yl)propoxy)isoquinoline-1-carbonitrile | 4.26 | 338.1 | D |
| 90 | 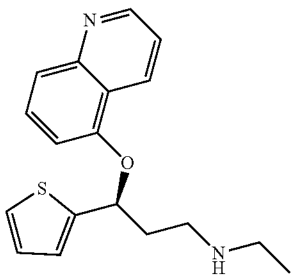 [SMILES: CCNCC[C@H](Oc1cccc2ncccc12)c1cccs1] | (S)-N-ethyl-3-(quinolin-5-yloxy)-3-(thiophen-2-yl)propan-1-amine | 3.56 | 313.1 | D |
| 91 | 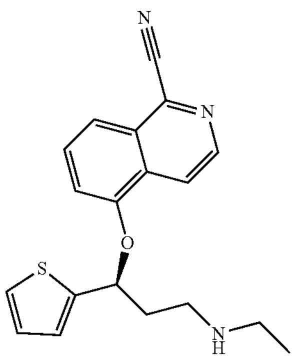 [SMILES: CCNCC[C@H](Oc1cccc2c(C#N)nccc12)c1cccs1] | (S)-5-(3-(ethylamino)-1-(thiophen-2-yl)propoxy)isoquinoline-1-carbonitrile | 4.28 | 338.1 | D |
| 92 | 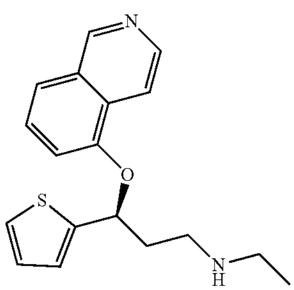 [SMILES: CCNCC[C@H](Oc1cccc2cnccc12)c1cccs1] | (S)-N-ethyl-3-(isoquinolin-5-yloxy)-3-(thiophen-2-yl)propan-1-amine | 4.13 | 312.9 | D |
| 93 | 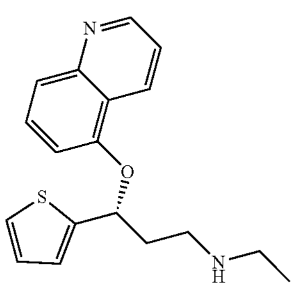 [SMILES: CCNCC[C@@H](Oc1cccc2ncccc12)c1cccs1] | (R)-N-ethyl-3-(quinolin-5-yloxy)-3-(thiophen-2-yl)propan-1-amine | 4.03 | 312.9 | D |

-continued

| EX | Structure | Chemical name | Ret time (min) | MS (M + H) | HPLC Method |
|---|---|---|---|---|---|
| 94 | 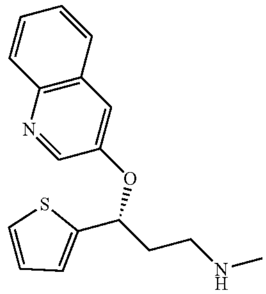 [SMILES: CNCC[C@@H](Oc1cnc2ccccc2c1)c1cccs1] | (R)-N-methyl-3-(quinolin-3-yloxy)-3-(thiophen-2-yl)propan-1-amine | 3.82 | 299.1 | D |
| 95 | 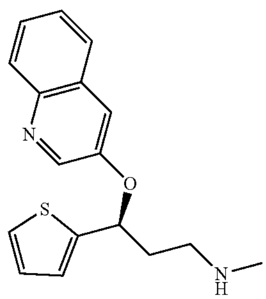 [SMILES: CNCC[C@H](Oc1cnc2ccccc2c1)c1cccs1] | (S)-N-methyl-3-(quinolin-3-yloxy)-3-(thiophen-2-yl)propan-1-amine | 3.90 | 299.1 | D |

Pharmacological Data

Binding Assay to Human $\alpha_2\delta$-1 Subunit of Cav2.2 Calcium Channel.

Human $\alpha_2\delta$-1 enriched membranes (2.5 µg) were incubated with 15 nM of radiolabeled [3H]-Gabapentin in assay buffer containing Hepes-KOH 10 mM, pH 7.4.

NSB (non specific binding) was measured by adding 10 µM pregabalin. The binding of the test compound was measured at five different concentrations. After 60 min incubation at 27° C., binding reaction was terminated by filtering through Multiscreen GF/C (Millipore) presoaked in 0.5% polyethyleneimine in Vacuum Manifold Station, followed by 3 washes with ice-cold filtration buffer containing 50 mM Tris-HCl, pH 7.4. Filter plates were dried at 60° C. for 1 h and 30 µl of scintillation cocktail were added to each well before radioactivity reading.

Readings were performed in a Trilux 1450 Microbeta radioactive counter (Perkin Elmer).

Binding Assay to Human Norepinephrine Transporter (NET).

Human norepinephrine transporter (NET) enriched membranes (5 µg) were incubated with 5 nM of radiolabeled [3H]-Nisoxetin in assay buffer containing 50 mM Tris-HCl, 120 mM NaCl, 5 mM KCl, pH 7.4.

NSB (non specific binding) was measured by adding desipramine 10 µM. The binding of the test compound was measured at five different concentrations. After 60 min incubation at 4° C., binding reaction was terminated by filtering through Multiscreen GF/C (Millipore) presoaked in 0.5% polyethyleneimine in Vacuum Manifold Station, followed by 3 washes with ice-cold filtration buffer containing 50 mM Tris-HCl, 0.9% NaCl, pH 7.4.

Filter plates were dried at 60° C. for 1 h and 30 µl of scintillation cocktail were added to each well before radioactivity reading.

Readings were performed in a Trilux 1450 Microbeta radioactive counter (Perkin Elmer).

The following scale has been adopted for representing the binding to the $\alpha 2\delta 1$ receptor expressed as Ki:
+ Ki-$\alpha 2\delta 1$>=3000 nM
++ 500 nM<Ki-$\alpha 2\delta 1$<3000 nM
+++ 100 nM<Ki-$\alpha 2\delta 1$<500 nM
++++ Ki-$\alpha 2\delta 1$<100 nM For the dual compounds and regarding the NET receptor, the following scale has been adopted for representing the binding expressed as Ki:
+ Ki-NET>=1000 nM
++ 500 nM<Ki-NET<1000 nM
+++ 100 nM<Ki-NET<500 nM
++++ Ki-NET<100 nM The results of the binding for $\alpha 2\delta$ receptor are shown in Table 1:

TABLE 1

| EX | Ki (nM) alpha2delta Hum |
|---|---|
| 1 | + |
| 2 | +++ |
| 3 | +++ |
| 4 | + |
| 5 | ++++ |
| 6 | + |
| 7 | + |
| 8 | + |
| 9 | ++++ |
| 10 | + |
| 11 | + |
| 12 | +++ |
| 13 | +++ |
| 14 | +++ |
| 15 | +++ |

TABLE 1-continued

| EX | Ki (nM) alpha2delta Hum |
|---|---|
| 16 | ++++ |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | + |
| 30 | + |
| 31 | + |
| 32 | +++ |
| 33 | + |
| 34 | ++ |
| 35 | + |
| 36 | + |
| 37 | + |
| 38 | + |
| 39 | + |
| 40 | + |
| 41 | +++ |
| 42 | ++++ |
| 43 | ++ |
| 44 | + |
| 45 | ++++ |
| 46 | +++ |
| 47 | +++ |
| 48 | +++ |
| 49 | +++ |
| 50 | ++ |
| 51 | +++ |
| 52 | ++++ |
| 53 | ++++ |
| 54 | ++ |
| 55 | ++ |
| 56 | +++ |
| 57 | +++ |
| 58 | +++ |
| 59 | ++++ |
| 60 | +++ |
| 61 | +++ |
| 62 | ++++ |
| 63 | +++ |
| 64 | + |
| 65 | + |
| 66 | ++++ |
| 67 | +++ |
| 68 | + |
| 69 | + |
| 70 | + |
| 71 | ++ |
| 72 | +++ |
| 73 | ++ |
| 74 | + |
| 75 | +++ |
| 76 | +++ |
| 77 | ++ |
| 78 | ++ |
| 79 | ++++ |
| 80 | ++ |
| 81 | +++ |
| 82 | + |
| 83 | +++ |
| 84 | ++ |
| 85 | ++ |
| 86 | + |
| 87 | +++ |
| 88 | +++ |
| 89 | ++++ |
| 90 | +++ |
| 91 | +++ |
| 92 | + |
| 93 | +++ |
| 94 | + |
| 95 | + |

The binding results for the α2δ receptor and the NET receptor for the dual compounds are shown in Table 2:

| EX | Ki (nM) NET Hum | Ki (nM) alpha2delta Hum |
|---|---|---|
| 1 | ++++ | + |
| 2 | +++ | +++ |
| 3 | ++++ | +++ |
| 9 | ++ | ++++ |
| 10 | ++ | + |
| 11 | ++++ | + |
| 12 | +++ | +++ |
| 13 | +++ | +++ |
| 14 | +++ | +++ |
| 15 | +++ | +++ |
| 17 | +++ | + |
| 18 | +++ | + |
| 25 | +++ | + |
| 30 | ++ | + |
| 41 | +++ | +++ |
| 42 | +++ | ++++ |
| 44 | +++ | + |
| 45 | +++ | ++++ |
| 46 | ++++ | +++ |
| 47 | +++ | +++ |
| 48 | +++ | +++ |
| 49 | +++ | +++ |
| 50 | ++++ | ++ |
| 51 | +++ | +++ |
| 52 | +++ | ++++ |
| 53 | +++ | ++++ |
| 54 | +++ | ++ |
| 56 | ++++ | +++ |
| 58 | ++ | +++ |
| 60 | +++ | +++ |
| 61 | +++ | +++ |
| 62 | ++ | ++++ |
| 65 | +++ | + |
| 67 | +++ | +++ |
| 68 | ++++ | + |
| 69 | ++ | + |
| 71 | +++ | ++ |
| 72 | ++ | +++ |
| 74 | +++ | + |
| 78 | +++ | ++ |
| 79 | ++ | ++++ |
| 81 | +++ | +++ |
| 82 | ++++ | + |
| 83 | +++ | +++ |
| 84 | +++ | ++ |
| 85 | +++ | ++ |
| 86 | +++ | + |
| 87 | +++ | +++ |
| 94 | +++ | + |

The invention claimed is:

1. A compound of general formula (I):

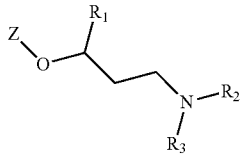

wherein:

Z is one of the following moieties:

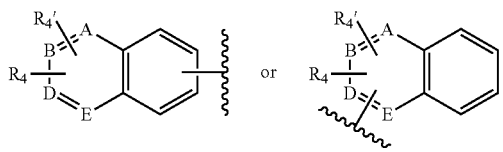

wherein $R_4$ and $R_{4'}$ independently represent a hydrogen atom; a branched or unbranched $C_{1-6}$ alkyl; —CN; or —C(O)NRR' wherein R and R' independently represent a hydrogen atom or a branched or unbranched $C_{1-6}$ alkyl radical;

A, B, D and E independently from one another represent —N—; or —C—;

with the proviso that at least one of A, B, D or E is —N—;

$R_1$ is an optionally substituted 5 to 9 membered heteroaryl group having at least one heteroatom selected from the group consisting of N, O or S; or from an optionally substituted 5 to 9 membered heterocycloalkyl group having at least one heteroatom selected from the group consisting of N, O or S;

$R_2$ and $R_3$ independently represent a hydrogen atom; a branched or unbranched $C_{1-6}$ alkyl or a benzyl;

or a pharmaceutically acceptable salt, isomer, prodrug or solvate thereof.

2. The compound according to claim 1, wherein $R_1$ represents a thiophene, a thiazole, a pyridine or a tetrahydropyran, all of which are optionally substituted by at least one substituent selected from the group consisting of halogen, $C_{1-6}$ alkyl, $C_{1-6}$-alkoxy, $C_{1-6}$-haloalkoxy, $C_{1-6}$-haloalkyl and hydroxy.

3. The compound according to claim 1 wherein $R_1$ represents:

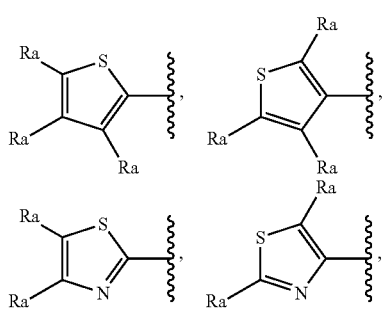

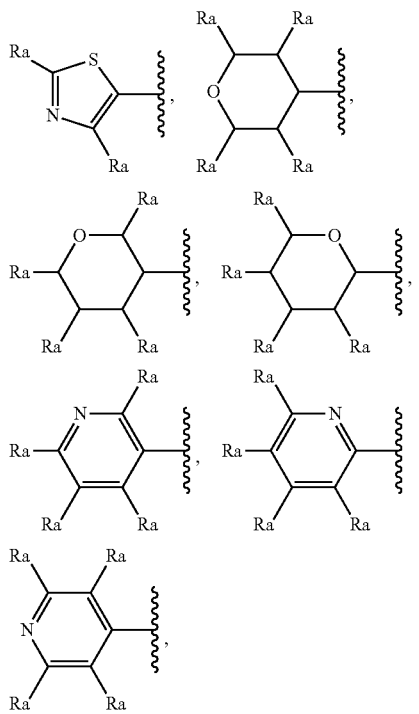

wherein each $R_a$ independently represents a hydrogen atom, a halogen, $C_{1-6}$ alkyl, $C_{1-6}$-alkoxy, $C_{1-6}$-haloalkoxy, $C_{1-6}$-haloalkyl or hydroxy.

4. The compound according to claim 1, wherein Z is:

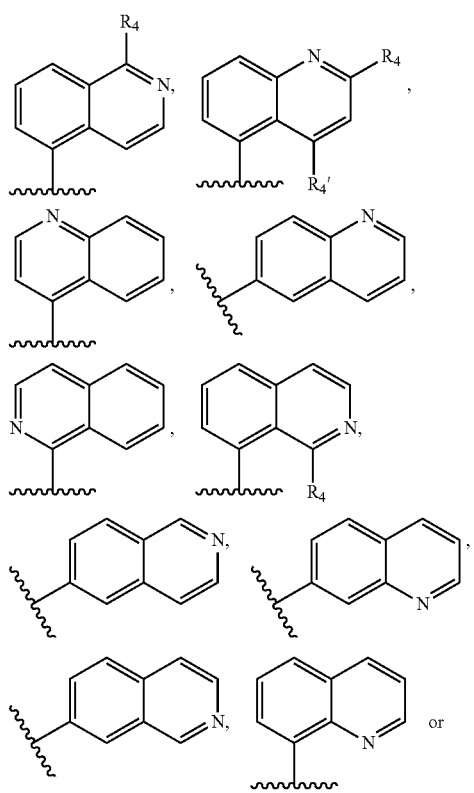

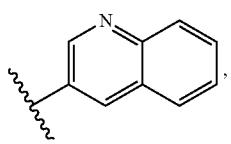

wherein each $R_4$ or $R_{4'}$ independently represents a hydrogen atom; a branched or unbranched $C_{1-6}$ alkyl; —CN; or —C(O)NRR' wherein R and R' independently represent a hydrogen atom or a branched or unbranched $C_{1-6}$ alkyl.

5. The compound according to claim 1, wherein $R_2$ and $R_3$ independently represent a hydrogen atom or a branched or unbranched $C_{1-6}$ alkyl.

6. The compound according to claim 1, which is a compound of formula (Iaa), (Iab), (Iba), (Ibb), (Ibc), (Ic) or (Id):

(Iaa)
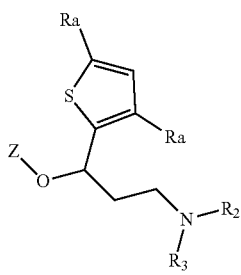

(Iab)
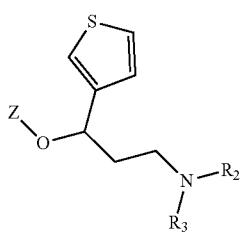

(Iba)
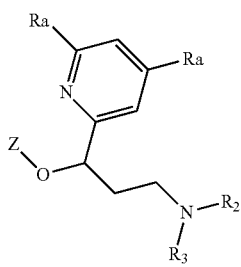

(Ibb)
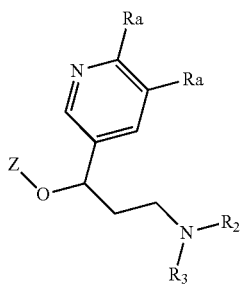

(Ibc)
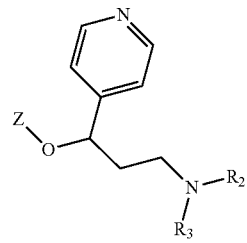

(Ic)
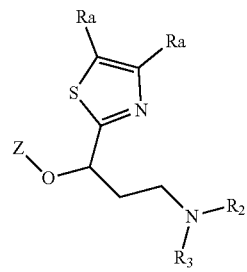

(Id)
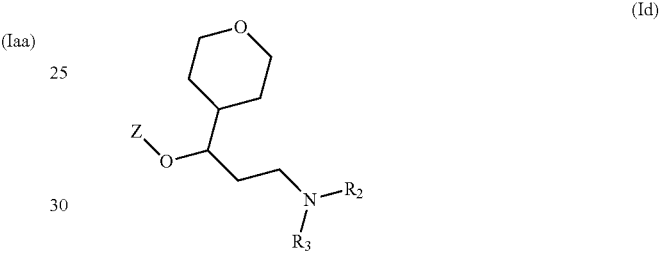

wherein $R_2$, $R_3$ and Z are as defined in claim 1, and each $R_a$ independently represents a hydrogen atom, a halogen, $C_{1-6}$ alkyl, $C_{1-6}$-alkoxy, $C_{1-6}$-haloalkoxy, $C_{1-6}$-haloalkyl or hydroxy.

7. The compound according to claim 1, which is selected from the group consisting of:
N-methyl-3-(quinolin-8-yloxy)-3-(thiophen-2-yl)propan-1-amine;
N-methyl-3-(quinolin-5-yloxy)-3-(thiophen-2-yl)propan-1-amine;
3-(Isoquinolin-5-yloxy)-N-methyl-3-(thiophen-2-yl)propan-1-amine;
N-methyl-3-(quinolin-4-yloxy)-3-(thiophen-2-yl)propan-1-amine;
N-ethyl-3-(isoquinolin-5-yloxy)-3-(thiophen-2-yl)propan-1-amine;
N-benzyl-3-(isoquinolin-5-yloxy)-3-(thiophen-2-yl)propan-1-amine;
(R)—N-methyl-3-(quinolin-6-yloxy)-3-(thiophen-2-yl)propan-1-amine;
3-(Isoquinolin-1-yloxy)-N,N-dimethyl-3-(thiophen-2-yl)propan-1-amine;
(S)—N-methyl-3-(quinolin-5-yloxy)-3-(thiophen-2-yl)propan-1-amine;
(S)-3-(isoquinolin-8-yloxy)-N-methyl-3-(thiophen-2-yl)propan-1-amine;
(S)-3-(isoquinolin-5-yloxy)-N-methyl-3-(thiophen-2-yl)propan-1-amine;
3-(Isoquinolin-8-yloxy)-N-methyl-3-(thiophen-2-yl)propan-1-amine;
(R)-3-(isoquinolin-8-yloxy)-N-methyl-3-(thiophen-2-yl)propan-1-amine;
(R)-3-(isoquinolin-5-yloxy)-N-methyl-3-(thiophen-2-yl)propan-1-amine;

(R)—N-methyl-3-(quinolin-5-yloxy)-3-(thiophen-2-yl)propan-1-amine;
5-(3-(Methylamino)-1-(thiophen-2-yl)propoxy)isoquinoline-1-carboxamide;
3-(Isoquinolin-5-yloxy)-N-methyl-3-(pyridin-3-yl)propan-1-amine;
3-(Isoquinolin-5-yloxy)-N-methyl-3-(tetrahydro-2H-pyran-4-yl)propan-1-amine;
3-(Isoquinolin-8-yloxy)-N-methyl-3-(tetrahydro-2H-pyran-4-yl)propan-1-amine;
N-methyl-3-(quinolin-5-yloxy)-3-(tetrahydro-2H-pyran-4-yl)propan-1-amine;
3-(Isoquinolin-8-yloxy)-N-methyl-3-(pyridin-3-yl)propan-1-amine;
3-(Isoquinolin-8-yloxy)-N-methyl-3-(pyridin-2-yl)propan-1-amine;
3-(Isoquinolin-5-yloxy)-N-methyl-3-(pyridin-2-yl)propan-1-amine;
3-(Isoquinolin-8-yloxy)-N-methyl-3-(6-(trifluoromethyl)pyridin-2-yl)propan-1-amine;
3-(Isoquinolin-5-yloxy)-N-methyl-3-(pyridin-4-yl)propan-1-amine;
3-(5-Chloropyridin-3-yl)-3-(isoquinolin-5-yloxy)-N-methylpropan-1-amine;
3-(Isoquinolin-8-yloxy)-N-methyl-3-(pyridin-4-yl)propan-1-amine;
3-(Isoquinolin-5-yloxy)-N-methyl-3-(6-(trifluoromethyl)pyridin-3-yl)propan-1-amine;
3-(Isoquinolin-5-yloxy)-N-methyl-3-(4-(trifluoromethyl)pyridin-2-yl)propan-1-amine;
3-(Isoquinolin-8-yloxy)-N-methyl-3-(4-(trifluoromethyl)pyridin-2-yl)propan-1-amine;
N-methyl-3-(quinolin-5-yloxy)-3-(4-(trifluoromethyl)pyridin-2-yl)propan-1-amine;
N-methyl-3-(4-methylthiazol-2-yl)-3-(quinolin-5-yloxy)propan-1-amine;
N-methyl-3-(pyridin-2-yl)-3-(quinolin-5-yloxy)propan-1-amine;
N-methyl-3-(5-methylthiazol-2-yl)-3-(quinolin-5-yloxy)propan-1-amine;
N-methyl-3-(pyridin-4-yl)-3-(quinolin-5-yloxy)propan-1-amine;
N-methyl-3-(pyridin-3-yl)-3-(quinolin-5-yloxy)propan-1-amine;
3-(Isoquinolin-5-yloxy)-N-methyl-3-(6-(trifluoromethyl)pyridin-2-yl)propan-1-amine;
N-methyl-3-(quinolin-5-yloxy)-3-(6-(trifluoromethyl)pyridin-2-yl)propan-1-amine;
3-(Isoquinolin-8-yloxy)-N-methyl-3-(6-(trifluoromethyl)pyridin-3-yl)propan-1-amine;
N-methyl-3-(quinolin-5-yloxy)-3-(6-(trifluoromethyl)pyridin-3-yl)propan-1-amine;
3-(5-Chlorothiophen-2-yl)-N-methyl-3-(quinolin-5-yloxy)propan-1-amine;
3-(5-Fluorothiophen-2-yl)-N-methyl-3-(quinolin-5-yloxy)propan-1-amine;
3-(Isoquinolin-5-yloxy)-N,N-dimethyl-3-(thiophen-2-yl)propan-1-amine;
3-(Isoquinolin-5-yloxy)-3-(thiophen-2-yl)propan-1-amine;
3-(5-Fluorothiophen-2-yl)-3-(isoquinolin-5-yloxy)-N-methylpropan-1-amine;
3-(3-Fluorothiophen-2-yl)-3-(isoquinolin-5-yloxy)-N-methylpropan-1-amine;
3-(3-Fluorothiophen-2-yl)-3-(isoquinolin-8-yloxy)-N-methylpropan-1-amine;
3-(3-Fluorothiophen-2-yl)-N-methyl-3-(quinolin-5-yloxy)propan-1-amine;
3-(5-Fluorothiophen-2-yl)-3-(isoquinolin-8-yloxy)-N-methylpropan-1-amine;
(S)-3-(5-fluorothiophen-2-yl)-3-(isoquinolin-5-yloxy)-N-methylpropan-1-amine;
(S)-3-(5-fluorothiophen-2-yl)-N-methyl-3-(quinolin-5-yloxy)propan-1-amine;
(R)-3-(5-fluorothiophen-2-yl)-3-(isoquinolin-5-yloxy)-N-methylpropan-1-amine;
(R)-3-(5-fluorothiophen-2-yl)-N-methyl-3-(quinolin-5-yloxy)propan-1-amine;
3-(Isoquinolin-6-yloxy)-N-methyl-3-(thiophen-2-yl)propan-1-amine;
(S)-3-(isoquinolin-6-yloxy)-N-methyl-3-(thiophen-2-yl)propan-1-amine;
3-(Isoquinolin-5-yloxy)-N-methyl-3-(thiophen-3-yl)propan-1-amine;
N-methyl-3-(quinolin-5-yloxy)-3-(thiophen-3-yl)propan-1-amine;
3-(Isoquinolin-8-yloxy)-N-methyl-3-(thiophen-3-yl)propan-1-amine;
(R)—N-methyl-3-((1-methylisoquinolin-5-yl)oxy)-3-(thiophen-2-yl)propan-1-amine;
(R)-3-(isoquinolin-5-yloxy)-N-methyl-3-(thiophen-3-yl)propan-1-amine;
(R)-3-(isoquinolin-8-yloxy)-N-methyl-3-(thiophen-3-yl)propan-1-amine;
(R)—N-methyl-3-((1-methylisoquinolin-8-yl)oxy)-3-(thiophen-2-yl)propan-1-amine;
(R)—N-methyl-3-(quinolin-5-yloxy)-3-(thiophen-3-yl)propan-1-amine;
(S)—N-methyl-3-((1-methylisoquinolin-8-yl)oxy)-3-(thiophen-2-yl)propan-1-amine;
(S)—N-methyl-3-((1-methylisoquinolin-5-yl)oxy)-3-(thiophen-2-yl)propan-1-amine;
(R)-3-((2,4-dimethylquinolin-5-yl)oxy)-N-methyl-3-(thiophen-2-yl)propan-1-amine;
(S)—N-methyl-3-(quinolin-5-yloxy)-3-(thiophen-3-yl)propan-1-amine;
(S)-3-(isoquinolin-5-yloxy)-N-methyl-3-(thiophen-3-yl)propan-1-amine;
(S)-3-(isoquinolin-8-yloxy)-N-methyl-3-(thiophen-3-yl)propan-1-amine;
3-(Isoquinolin-8-yloxy)-N-methyl-3-(thiazol-2-yl)propan-1-amine;
3-(Isoquinolin-5-yloxy)-N-methyl-3-(thiazol-2-yl)propan-1-amine;
N-methyl-3-(quinolin-5-yloxy)-3-(thiazol-2-yl)propan-1-amine;
N-methyl-3-(quinolin-7-yloxy)-3-(thiophen-2-yl)propan-1-amine;
3-(Isoquinolin-7-yloxy)-N-methyl-3-(thiophen-2-yl)propan-1-amine;
5-(3-(Methylamino)-1-(thiophen-2-yl)propoxy)isoquinoline-1-carbonitrile;
(S)—N-methyl-3-(quinolin-5-yloxy)-3-(thiazol-2-yl)propan-1-amine;
(R)—N-methyl-3-(quinolin-5-yloxy)-3-(thiazol-2-yl)propan-1-amine;
(S)-3-(5-chlorothiophen-2-yl)-N-methyl-3-(quinolin-5-yloxy)propan-1-amine;
(R)-3-(5-chlorothiophen-2-yl)-N-methyl-3-(quinolin-5-yloxy)propan-1-amine;
(S)-3-(5-fluorothiophen-2-yl)-3-(isoquinolin-8-yloxy)-N-methylpropan-1-amine;

(R)-3-(5-fluorothiophen-2-yl)-3-(isoquinolin-8-yloxy)-N-methylpropan-1-amine;
(S)-3-(3-fluorothiophen-2-yl)-3-(isoquinolin-5-yloxy)-N-methylpropan-1-amine;
(R)-3-(3-fluorothiophen-2-yl)-3-(isoquinolin-5-yloxy)-N-methylpropan-1-amine;
(S)-3-(3-fluorothiophen-2-yl)-N-methyl-3-(quinolin-5-yloxy)propan-1-amine;
(R)-3-(3-fluorothiophen-2-yl)-N-methyl-3-(quinolin-5-yloxy)propan-1-amine;
(S)-3-(3-fluorothiophen-2-yl)-3-(isoquinolin-8-yloxy)-N-methylpropan-1-amine;
(R)-3-(3-fluorothiophen-2-yl)-3-(isoquinolin-8-yloxy)-N-methylpropan-1-amine;
(R)—N-ethyl-3-(isoquinolin-5-yloxy)-3-(thiophen-2-yl)propan-1-amine;
(R)-5-(3-(ethylamino)-1-(thiophen-2-yl)propoxy)isoquinoline-1-carbonitrile;
(S)—N-ethyl-3-(quinolin-5-yloxy)-3-(thiophen-2-yl)propan-1-amine;
(S)-5-(3-(ethylamino)-1-(thiophen-2-yl)propoxy)isoquinoline-1-carbonitrile;
(S)—N-ethyl-3-(isoquinolin-5-yloxy)-3-(thiophen-2-yl)propan-1-amine;
(R)—N-ethyl-3-(quinolin-5-yloxy)-3-(thiophen-2-yl)propan-1-amine;
(R)—N-methyl-3-(quinolin-3-yloxy)-3-(thiophen-2-yl)propan-1-amine and
(S)—N-methyl-3-(quinolin-3-yloxy)-3-(thiophen-2-yl)propan-1-amine;

or a pharmaceutically acceptable salt, prodrug or solvate thereof.

8. The compound according to claim 1, which is a compound of formula (Iaa1), (Iaa2), (Iaa3), (Iaa4), (Iab1), (Iab2), (Iab3), (Iab4), (Iab5), (Iba1), (Ibb1), (Ibc1), (Ic1), (Ic2) or (Id1):

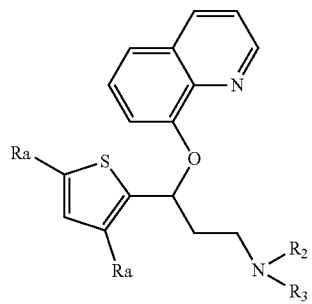
(Iaa1)

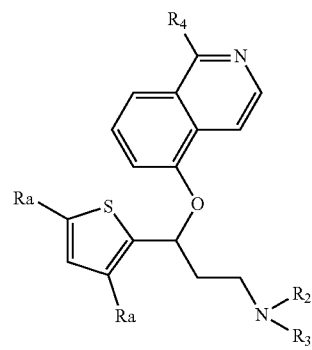
(Iaa2)

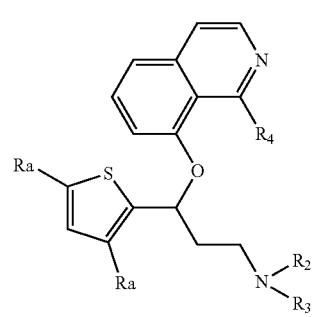
(Iaa3)

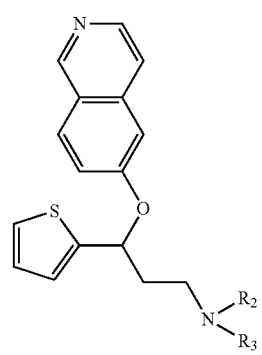
(Iaa4)

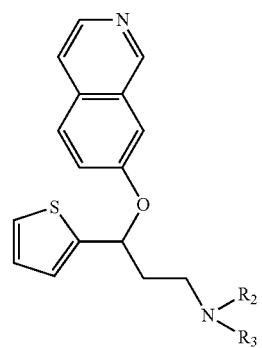
(Iab1)

(Iab2)

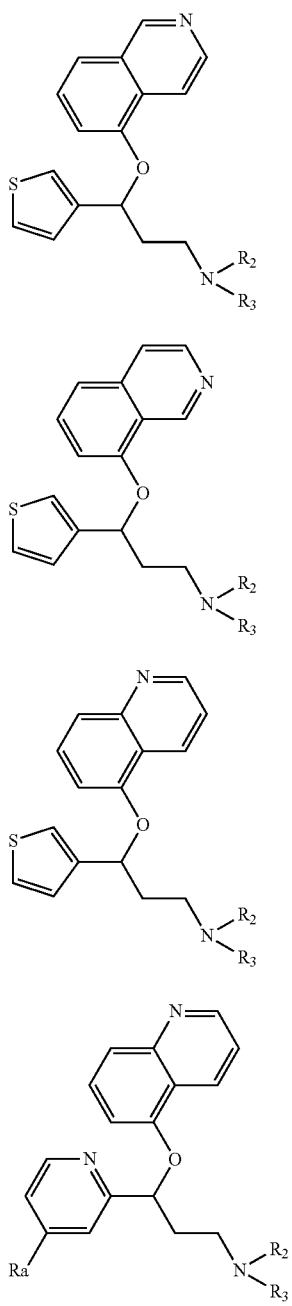
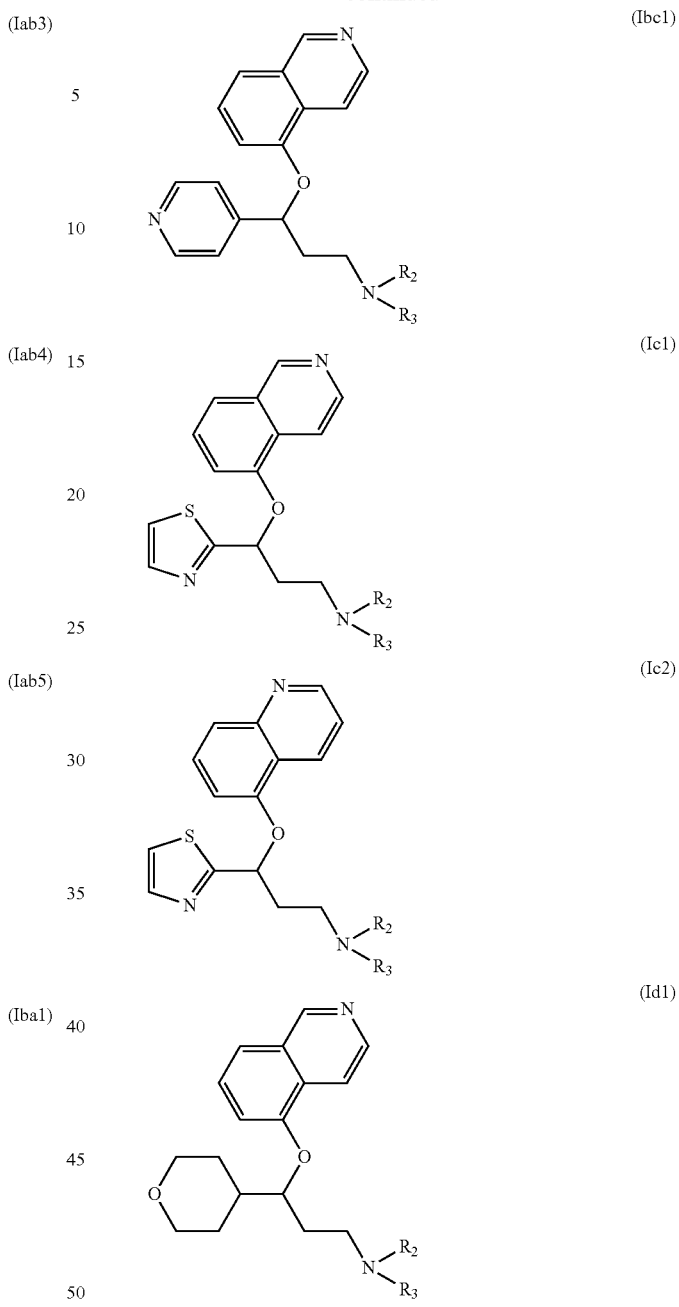

wherein $R_2$, $R_3$, $R_4$ and $R'_4$ are as defined in claim 1, and each $R_a$ independently represents a hydrogen atom, a halogen, $C_{1-6}$ alkyl, $C_{1-6}$-alkoxy, $C_{1-6}$-haloalkoxy, $C_{1-6}$-haloalkyl or a hydroxyl group.

9. The compound according to claim 8, which is selected from the group consisting of:
N-methyl-3-(quinolin-8-yloxy)-3-(thiophen-2-yl)propan-1-amine;
N-methyl-3-(quinolin-5-yloxy)-3-(thiophen-2-yl)propan-1-amine;
3-(Isoquinolin-5-yloxy)-N-methyl-3-(thiophen-2-yl)propan-1-amine;
(S)—N-methyl-3-(quinolin-5-yloxy)-3-(thiophen-2-yl)propan-1-amine;
(S)-3-(isoquinolin-8-yloxy)-N-methyl-3-(thiophen-2-yl)propan-1-amine;

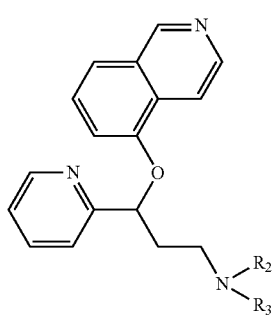

(S)-3-(isoquinolin-5-yloxy)-N-methyl-3-(thiophen-2-yl) propan-1-amine;
3-(Isoquinolin-8-yloxy)-N-methyl-3-(thiophen-2-yl)propan-1-amine;
(R)-3-(isoquinolin-8-yloxy)-N-methyl-3-(thiophen-2-yl) propan-1-amine;
(R)-3-(isoquinolin-5-yloxy)-N-methyl-3-(thiophen-2-yl) propan-1-amine;
(R)—N-methyl-3-(quinolin-5-yloxy)-3-(thiophen-2-yl) propan-1-amine;
3-(Isoquinolin-5-yloxy)-N-methyl-3-(pyridin-3-yl)propan-1-amine;
3-(Isoquinolin-5-yloxy)-N-methyl-3-(tetrahydro-2H-pyran-4-yl)propan-1-amine;
3-(Isoquinolin-5-yloxy)-N-methyl-3-(pyridin-4-yl)propan-1-amine;
3-(Isoquinolin-8-yloxy)-N-methyl-3-(4-(trifluoromethyl) pyridin-2-yl)propan-1-amine;
3-(5-Chlorothiophen-2-yl)-N-methyl-3-(quinolin-5-yloxy)propan-1-amine;
3-(5-Fluorothiophen-2-yl)-N-methyl-3-(quinolin-5-yloxy)propan-1-amine;
3-(Isoquinolin-5-yloxy)-3-(thiophen-2-yl)propan-1-amine;
3-(5-Fluorothiophen-2-yl)-3-(isoquinolin-5-yloxy)-N-methylpropan-1-amine;
3-(3-Fluorothiophen-2-yl)-3-(isoquinolin-5-yloxy)-N-methylpropan-1-amine;
3-(3-Fluorothiophen-2-yl)-3-(isoquinolin-8-yloxy)-N-methylpropan-1-amine;
3-(3-Fluorothiophen-2-yl)-N-methyl-3-(quinolin-5-yloxy)propan-1-amine;
3-(5-Fluorothiophen-2-yl)-3-(isoquinolin-8-yloxy)-N-methylpropan-1-amine;
(S)-3-(5-fluorothiophen-2-yl)-3-(isoquinolin-5-yloxy)-N-methylpropan-1-amine;
(S)-3-(5-fluorothiophen-2-yl)-N-methyl-3-(quinolin-5-yloxy)propan-1-amine;
(R)-3-(5-fluorothiophen-2-yl)-3-(isoquinolin-5-yloxy)-N-methylpropan-1-amine;
R)-3-(5-fluorothiophen-2-yl)-N-methyl-3-(quinolin-5-yloxy)propan-1-amine;
3-(Isoquinolin-6-yloxy)-N-methyl-3-(thiophen-2-yl)propan-1-amine;
3-(Isoquinolin-5-yloxy)-N-methyl-3-(thiophen-3-yl)propan-1-amine;
3-(Isoquinolin-8-yloxy)-N-methyl-3-(thiophen-3-yl)propan-1-amine;
(R)-3-(isoquinolin-5-yloxy)-N-methyl-3-(thiophen-3-yl) propan-1-amine;
(R)-3-(isoquinolin-8-yloxy)-N-methyl-3-(thiophen-3-yl) propan-1-amine;
(R)—N-methyl-3-((1-methylisoquinolin-8-yl)oxy)-3-(thiophen-2-yl)propan-1-amine;
(S)—N-methyl-3-((1-methylisoquinolin-5-yl)oxy)-3-(thiophen-2-yl)propan-1-amine;
(R)-3-((2,4-dimethylquinolin-5-yl)oxy)-N-methyl-3-(thiophen-2-yl)propan-1-amine;
(S)—N-methyl-3-(quinolin-5-yloxy)-3-(thiophen-3-yl) propan-1-amine;
(S)-3-(isoquinolin-5-yloxy)-N-methyl-3-(thiophen-3-yl) propan-1-amine;
(S)-3-(isoquinolin-8-yloxy)-N-methyl-3-(thiophen-3-yl) propan-1-amine;
3-(Isoquinolin-5-yloxy)-N-methyl-3-(thiazol-2-yl)propan-1-amine;
N-methyl-3-(quinolin-5-yloxy)-3-(thiazol-2-yl)propan-1-amine;
3-(Isoquinolin-7-yloxy)-N-methyl-3-(thiophen-2-yl)propan-1-amine;
(S)-3-(5-chlorothiophen-2-yl)-N-methyl-3-(quinolin-5-yloxy)propan-1-amine;
(R)-3-(5-chlorothiophen-2-yl)-N-methyl-3-(quinolin-5-yloxy)propan-1-amine;
(R)-3-(5-fluorothiophen-2-yl)-3-(isoquinolin-8-yloxy)-N-methylpropan-1-amine;
(S)-3-(3-fluorothiophen-2-yl)-3-(isoquinolin-5-yloxy)-N-methylpropan-1-amine;
(R)-3-(3-fluorothiophen-2-yl)-3-(isoquinolin-5-yloxy)-N-methylpropan-1-amine;
(S)-3-(3-fluorothiophen-2-yl)-N-methyl-3-(quinolin-5-yloxy)propan-1-amine;
(R)-3-(3-fluorothiophen-2-yl)-N-methyl-3-(quinolin-5-yloxy)propan-1-amine;
(S)-3-(3-fluorothiophen-2-yl)-3-(isoquinolin-8-yloxy)-N-methylpropan-1-amine;
(R)-3-(3-fluorothiophen-2-yl)-3-(isoquinolin-8-yloxy)-N-methylpropan-1-amine and
(R)—N-methyl-3-(quinolin-3-yloxy)-3-(thiophen-2-yl) propan-1-amine;
or a pharmaceutically acceptable salt, prodrug or solvate thereof.

10. A process for the preparation of a compound of formula (I):

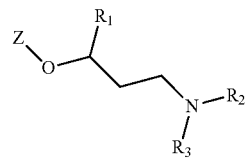

(I)

comprising:
A) reaction of a compound of formula (II):

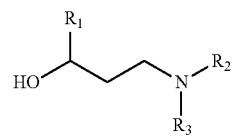

(II)

with a compound of formula (IIIa) or (IIIb):

Z—OH    (IIIa)

or

Z—X    (IIIb)

wherein Z is one of the following moieties:

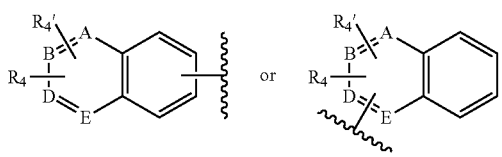

wherein

R$_4$ and R$_{4'}$ independently represent a hydrogen atom; a branched or unbranched C$_{1-6}$ alkyl; —CN; or —C(O)NRR' wherein R and R' independently represent a hydrogen atom or a branched or unbranched C$_{1-6}$ alkyl radical;

A, B, D and E independently from one another represent —N—; or —C—;

with the proviso that at least one of A, B, D or E is —N—;

R$_1$ is an optionally substituted 5 to 9 membered heteroaryl group having at least one heteroatom selected from the group consisting of N, O or S; or from an optionally substituted 5 to 9 membered heterocycloalkyl group having at least one heteroatom selected from the group consisting of N, O or S; R$_2$ and R$_3$ independently represent a hydrogen atom; a branched or unbranched C$_{1-6}$ alkyl or a benzyl; and X represents a halogen, or B) reaction of a compound of formula (V):

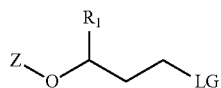 (V)

with a compound of formula (VI):

 (VI)

wherein R$_1$, R$_2$, R$_3$ and Z are as defined above, and LG represents a leaving group, including chloro, bromo, iodo, mesylate, tosylate, nosylate and triflate.

11. A method of treating diseases and/or disorders mediated by the subunit α2δ, including α2δ-1 subunit of voltage-gated calcium channels and/or noradrenaline transporter (NET), in a subject in need thereof, wherein the disease or disorder is selected from the group consisting of pain, depression, anxiety and attention-deficit-/hyperactivity disorder (ADHD), comprising administration of an effective amount of the compound according to claim 1.

12. The method according to claim 11, wherein the pain is selected from the group consisting of medium to severe pain, visceral pain, chronic pain, cancer pain, migraine, inflammatory pain, acute pain neuropathic pain, allodynia and hyperalgesia.

13. A pharmaceutical composition comprising the compound according to claim 1, or a pharmaceutically acceptable salt, isomer, prodrug or solvate thereof, and at least a pharmaceutically acceptable carrier, additive, adjuvant or vehicle.

14. The method according to claim 12, wherein the pain is mechanical allodynia or thermal hyperalgesia.

\* \* \* \* \*